US00RE42461E

(19) United States
(12) Reissued Patent
Rosenblum et al.

(10) Patent Number: US RE42,461 E
(45) Date of Reissued Patent: Jun. 14, 2011

(54) HYDROXY-SUBSTITUTED AZETIDINONE COMPOUNDS USEFUL AS HYPOCHOLESTEROLEMIC AGENTS

(75) Inventors: Stuart B. Rosenblum, West Orange, NJ (US); Sundeep Dugar, San Jose, CA (US); Duane A. Burnett, Bernardsville, NJ (US); John W. Clader, Milton, VT (US); Brian A. McKittrick, New Vernon, NJ (US)

(73) Assignee: Schering Corporation, Kenilworth, NJ (US)

(21) Appl. No.: 12/797,341

(22) PCT Filed: Sep. 14, 1994

(86) PCT No.: PCT/US94/10099

§ 371 (c)(1),
(2), (4) Date: Mar. 18, 1996

(87) PCT Pub. No.: WO95/08532

PCT Pub. Date: Mar. 30, 1995

Related U.S. Patent Documents

Reissue of:
(64) Patent No.: Re. 37,721
Issued: May 28, 2002
Appl. No.: 09/594,996
Filed: Jun. 15, 2000

Which is a Reissue of:
(64) Patent No.: 5,767,115
Issued: Jun. 16, 1998
Appl. No.: 08/617,751
Filed: Mar. 18, 1996

(51) Int. Cl.
*C07D 205/08* (2006.01)
*A61P 9/10* (2006.01)
*A61P 3/06* (2006.01)
*A61K 31/395* (2006.01)

(52) U.S. Cl. ..... 514/210.02; 540/200

(58) Field of Classification Search ..... 540/200; 514/210, 210.02

See application file for complete search history.

(56) References Cited

U.S. PATENT DOCUMENTS

| | | | |
|---|---|---|---|
| 4,144,232 | A | 3/1979 | Koppel et al. |
| 4,375,475 | A | 3/1983 | Willard et al. |
| 4,443,372 | A | 4/1984 | Luo et al. |
| 4,479,900 | A | 10/1984 | Luo |
| 4,500,456 | A | 2/1985 | Spitzer et al. |
| 4,576,749 | A | 3/1986 | Zahler et al. |
| 4,576,753 | A | 3/1986 | Kamiya et al. |
| 4,595,532 | A | 6/1986 | Miller |
| 4,620,867 | A | 11/1986 | Luo |
| 4,633,017 | A | 12/1986 | Mueller et al. |
| 4,659,716 | A | 4/1987 | Villani et al. |
| 4,675,399 | A | 6/1987 | Miller |
| 4,680,391 | A | 7/1987 | Firestone et al. |
| 4,759,923 | A | 7/1988 | Buntin et al. |
| 4,784,734 | A | 11/1988 | Torii et al. |
| 4,794,108 | A | 12/1988 | Kishimoto et al. |
| 4,803,266 | A | 2/1989 | Kawashima et al. |
| 4,806,564 | A | 2/1989 | Chabala et al. |
| 4,816,477 | A | 3/1989 | Girotra et al. |
| 4,834,846 | A | 5/1989 | Abramson et al. |
| 4,847,271 | A | 7/1989 | Chabala et al. |
| 4,876,365 | A | 10/1989 | Kirkup et al. |
| 4,983,597 | A | 1/1991 | Yang et al. |

(Continued)

FOREIGN PATENT DOCUMENTS

| | | |
|---|---|---|
| CA | 1063108 | 9/1979 |

(Continued)

OTHER PUBLICATIONS

Allain et al., Enzymatic Determination of Total Serum Cholesterol, Clinical Chemical 20:470-475 (1974).

(Continued)

*Primary Examiner* — Mark L Berch
(74) *Attorney, Agent, or Firm* — Ropes & Gray LLP; James F. Haley, Jr.; Carl A. Morales

(57) ABSTRACT

Hydroxy-substituted azetidinone hypocholesterolemic agents of the formula or a pharmaceutically acceptable salt thereof, wherein:
$Ar^1$ and $Ar^2$ are aryl or $R^4$-substituted aryl;
$Ar^3$ is aryl or $R^5$-substituted aryl;
X, Y and Z are —$CH_2$—, —CH(lower alkyl)— or —C(dilower alkyl)—;
R and $R^2$ are —$OR^6$, —O(CO)$R^6$, —O(CO)$OR^9$ or —O(CO)$NR^6R^7$;
$R^1$ and $R^3$ are H or lower alkyl;
q is 0 or 1; r is 0 or 1; m, n and p are 0-4; provided that at least one of q and r is 1, and the sum of m, n, p, q and r is 1-6; and provided that when p is O and r is 1, the sum of m, q and n is 1-5;
$R^4$ is selected from lower alkyl, $R_5$, —$CF_3$, —CN, —$NO_2$ and halogen $R^5$ is selected from —$OR^6$, —O(CO)$R^6$, —O(CO)$OR^9$, —$O(CH_2)_{1-5}OR^6$, —O(CO)$NR^6R^7$, —$NR_6R^7$, —$NR^6$(CO)$R^7$, —$NR^6$(CO)$OR^9$, —$NR^6$(CO)$NR^7R^8$, —$NR^6SO_2R^9$, —$COOR^6$, —$CONR^6R^7$, —$COR^6$, —$SO_2NR^6R^7$, $S(O)_{0-2}R^9$, —$O(CH_2)_{1-10}$—$COOR^6$, —$O(CH_2)_{1-10}CON^6R^7$, —(lower alkylene)$COOR^6$ and —CH═CH—$COOR^6$;
$R^6$, $R^7$ and $R^8$ are H, lower alkyl or aryl-substituted Ic
$R^9$ is lower alkyl, aryl or aryl-substituted lower alkyl;
are disclosed, as well as a method of lowering serum cholesterol by administering said compounds, alone or in combination with a cholesterol biosynthesis inhibitor, pharmaceutical compositions containing them; and a process for preparing them.

8 Claims, No Drawings

U.S. PATENT DOCUMENTS

| | | | |
|---|---|---|---|
| 5,030,628 | A | 7/1991 | Joyeau et al. |
| 5,099,034 | A | 3/1992 | Yoshida et al. |
| 5,120,729 | A | 6/1992 | Chabala et al. |
| 5,124,337 | A | 6/1992 | Dugar et al. |
| 5,159,025 | A | 10/1992 | Terada |
| 5,229,381 | A | 7/1993 | Doherty et al. |
| 5,229,510 | A | 7/1993 | Knight et al. |
| 5,238,950 | A | 8/1993 | Clader et al. |
| 5,306,817 | A | 4/1994 | Thiruvengadam et al. |
| 5,348,953 | A | 9/1994 | Doherty et al. |
| 5,350,868 | A | 9/1994 | Yoshida et al. |
| 5,412,092 | A | 5/1995 | Rey et al. |
| 5,550,229 | A | 8/1996 | Iwasaki et al. |
| 5,576,470 | A | 11/1996 | Tuller et al. |
| 5,595,997 | A | 1/1997 | Aberg et al. |
| 5,624,920 | A | 4/1997 | McKittrick et al. |
| 5,631,365 | A | 5/1997 | Rosenblum et al. |
| 5,633,246 | A | 5/1997 | McKittrick et al. |
| 5,661,145 | A | 8/1997 | Davis |
| 5,688,785 | A | 11/1997 | Vaccaro |
| 5,688,787 | A | 11/1997 | Burnette et al. |
| 5,688,990 | A | 11/1997 | Shankar |
| 5,698,548 | A | 12/1997 | Dugar et al. |
| 5,728,827 | A | 3/1998 | Thiruvengadam et al. |
| 5,739,321 | A | 4/1998 | Wu et al. |
| 5,744,467 | A | 4/1998 | McKittrick et al. |
| 5,767,115 | A | 6/1998 | Rosenblum et al. |
| 5,767,126 | A | 6/1998 | Marchbanks |
| 5,817,806 | A | 10/1998 | Rossi et al. |
| 5,846,966 | A | 12/1998 | Rosenblum et al. |
| 5,847,115 | A | 12/1998 | Iwasaki et al. |
| 5,856,473 | A | 1/1999 | Shankar |
| 5,925,668 | A | 7/1999 | Biewenga et al. |
| RE36,481 | E | 1/2000 | Inamine et al. |
| 6,372,756 | B1 | 4/2002 | Christians et al. |
| 6,455,572 | B1 | 9/2002 | Day et al. |
| 6,465,490 | B1 | 10/2002 | Bernotas et al. |
| 6,982,251 | B2 | 1/2006 | Ghosal et al. |

FOREIGN PATENT DOCUMENTS

| | | | |
|---|---|---|---|
| CA | 1173837 | | 9/1984 |
| CA | 1213596 | | 11/1986 |
| CA | 1253146 | | 4/1989 |
| CA | 1262357 | | 10/1989 |
| CA | 1267415 | | 4/1990 |
| CA | 1268780 | | 5/1990 |
| CA | 2004355 | | 6/1990 |
| CA | 2024267 | | 3/1991 |
| CA | 1286304 | | 7/1991 |
| CA | 2052973 | | 4/1992 |
| CA | 2072215 | | 12/1992 |
| CA | 2114007 | | 2/1993 |
| CA | 2152351 | | 7/1994 |
| CA | 1331755 | | 8/1994 |
| CA | 2154257 | | 8/1994 |
| CA | 2172149 | | 11/2000 |
| DE | 2046823 | | 3/1972 |
| EP | 0 199 630 | A1 | 10/1986 |
| EP | 0199630 | | 10/1986 |
| EP | 0 264 231 | A1 | 4/1988 |
| EP | 0264231 | | 4/1988 |
| EP | 0 333 268 | A1 | 9/1989 |
| EP | 0333268 | | 9/1989 |
| EP | 0337 549 | A1 | 10/1989 |
| EP | 0337549 | | 10/1989 |
| EP | 0 365 364 | A2 | 4/1990 |
| EP | 0365364 | | 4/1990 |
| EP | 0 401 705 | A1 | 12/1990 |
| EP | 0 415 487 | A2 | 3/1991 |
| EP | 0415487 | | 3/1991 |
| EP | 0 462 667 | A2 | 12/1991 |
| EP | 0462667 | | 12/1991 |
| EP | 0 481 671 | A1 | 4/1992 |
| EP | 0481671 | | 4/1992 |
| EP | 508 425 | A1 | 10/1992 |
| EP | 0 524 595 | A1 | 1/1993 |
| EP | 524 595 | A1 | 1/1993 |
| EP | 0524595 | | 1/1993 |
| EP | 0720599 | | 7/1996 |
| JP | 8-505141 | | 4/1996 |
| WO | WO87/04429 | | 7/1987 |
| WO | WO93/02048 | | 2/1993 |
| WO | WO 94/06784 | | 3/1994 |
| WO | WO94/17038 | | 4/1994 |
| WO | WO94/14433 | | 7/1994 |
| WO | WO94/17036 | | 8/1994 |
| WO | WO94/17038 | | 8/1994 |
| WO | WO 94/19351 | | 9/1994 |
| WO | WO95/08532 | | 3/1995 |
| WO | WO01/32161 | | 5/2001 |

OTHER PUBLICATIONS

Baxter, Squalestatin 1, a Potent Inhibitor of Squalene Synthase, Which Lowers Serum Cholesterol in vivo, Journal of Biological Chemistry 267:11705-11708 (1992).

Burrier et al., The Effect of Acyl CoA:Cholesterol Acyltransferase Inhibition on the Uptake, Esterification and Secretion of Cholesterol by the Hamster Small Intestine, The Journal of Pharmacology and Experimental Therapeutics 272:156-163 (1994).

Burrier et al., Demonstration of a Direct Effect on Hepatic Acyl CoA:Cholesterol Acyl Transferase (ACAT) Activity By An Orally Administered Enzyme Inhibitor in the Hamster, Biochemical Pharmacology 47:1545-1551 (1994).

Clader et al., Substituted (1,2-Diarylethyl)amide Acy-CoA:Cholesterol Acyltransferase Inhibitors: Effect of Polar Groups in Vitro and in Vivo Activity, Journal of Medicinal Chemistry 38:1600-1607 (1995).

Durst et al., Metallation of N-Substituted β-Lactams, A Method for the Introduction of 3-Substituents into β-Lactams, Canadian Journal of Chemistry, 50:3196-3201 (1971).

Georg et al., 3-(1'-Hydroxyethyl)-2-Azetidinones From 3-Hydroxybutyrates and N-Arylaldimines, Tetrahedron Letters 26(33):3903-3906 (1985).

Hart et al., An Enantioselective Approach to Carbapenen Antibodies: Formal Synthesis of (+)-Thienamycin, Tetrahedron Letters, 26(45):5493-5496 (1985).

Harwood, Pharmacologic consequences of cholesterol absorption inhibition: alteration in cholesterol metabolism and reduction in plasma cholesterol concentration induced by the synthetic saponin β-tigogenin cellobioside (CP-88818; liqueside), Journal of Lipid Research 34:377-395 (1993).

Hoekman et al., Synthesis of Homologues of 4,5-Dihydroxy- and 4-Hydroxy-5-oxohexanoic Add δ-Lactones, J. Agric, Food Chem. 30:920-924 (1982).

Horie et al., Hypolipidemic effects of NB-598 in dogs, Atherosclerosis 88:183-192 (1991).

Illingworth, An Overview of Lipid-Lower Drugs, Drugs 36:63:71 (1988).

International Search Report dated Dec. 8, 1994 in PCT/US94/10099.

Mayrhofer et al., Simple Prep. of 3-Benzylidene-2-azetilidinones, Synthesis 247-8 (1980).

Nobuki et al., Stereoselective syntheses of β-lactam derivatives by ultrasound promoted Reformatskii reaction, Chemical Abstracts No. 106:17 (1977) Abstract 138174y.

Otto et al., Stereochemistry of dehydration and halogenation of αR* and αS* isomeric 3-(α-hydroyxbenzy1-1-4-dipheny1=2-azetidinones, Chemical Abstracts 19:99 (1983) Abstract 18083h.

Panfil et al., Synthesis of α-Lactams from a,α-Unsaturated Sugar δ-Lactones, Heterocycles 24:1009-1617(1986).

Ram et al., Potential hypolipidemic agents:Part V†-Synthesis biological activity of new ethyl 4-(2-oxazetidin-4-yl)phenoxyalkanoatest‡, Indian Journal of Chemistry 29B:1134-1137 (1990).

Salisbury et al., Hypocholesterolemic activity of a novel inhibitor of cholesterol absorption, SCH 48461, Atherosclerosis 115:45-63 (1995).

Schnitzer-Polokoff et al., Effects of Acyl-CoA:Cholesterol O-Acyltransferase Inhibition on Cholesterol Absorption and Plasma Lipoprotein Composition in Hamsters, Comp. Biochem. Physiol. 99A:665-670 (1991).

Simova, Aldol-type addition of hydrocinnamic acid esters to benzylideneaniline, Chemical Abstracts 15:86 (1977) Abstract 106130h.
Summary Factfile, May 1992, "Anti-Atherosclerotic Agents" Current Drugs Ltd., pp. A5-A23.
USAN and the USP dictionary of drug names, U.S. Pharmacopeial Convention, Inc., entries ATEVI-ATRIM, p. 62 (though Jun. 15, 1993).
USP Dictionary of USAN and International Drug Names, U.S. Pharmacopeial Convention, Inc., entries AT-101-ATORV, p. 62 (though Jun. 15, 1994).
Witztum, Current Approaches to Drug Therapy for the Hypercholesterolemic Patient, Circulation 80:1101-1114 (1989).
Written Opinion dated May 16, 1995 in PCT/US94/10099.
U.S. Appl. No. 07/995,488, filed Dec. 12, 1992, Davis.
U.S. Appl. No. 08/102,440, filed Sep. 21, 1993, Rosenblum.
"Heart disease" Statistics http://www.heartandstroke.com/site/c.ikIQLcMWJtE/b.3483991/k.34A8/Statistics.html#heartdiesease © 2010.
Abel et al., Cortisol Metabolism by Human Liver in vitro-IV. Metabolism of 9 α-fluorocortisol by Human Liver Microsomes and Cytosol., J. Steroid. Biochem. Molec. Biol. 46(6):833-839 (1993).
Abel et al., Cortisol Metabolism by Human Liver in vitro-I Metabolite identification and Inter-Individual Variability, J. Steroid. Biochem. Molec. Biol. 43(7):713-719 (1992).
Ajmera et al., Synthesis and Biological Activity of 5-Fluoro-2',3'-dideoxy-3'-Fluorouridine and Its 5'-Phosphate, J. Med. Chem. 27(1):11-14 (1984).
Altmann et al., Niemann-Pick C1 Like 1 Protein Is Critical for Intestinal Cholesterol Absorption, Science 303:1201-1204 (2004).
Altschul et al., Influence of Nicotinic Acid on Serum Cholesterol in Man, Arch Biochem, 54(2):558-559 (1955).
American Heritage Dictionary of the English language, 2nd College ed., Houghton Mifflin Co.—"appy as remedy" (1985).
Angelin et al., Combined treatment with cholestyramine and nicotinic acid in heterozygous familial hypercholesterolaemia: effects on biliary lipid composition, Eur. J. Clin. Invest. 16:391-396 (1986).
Anitschkow and Chalatow, On Experimental Cholesterin Steatosis and Its Significance in the Origin of Some Pathological Processes, Arteriosclerosis 3(2):178-182 (1983).
Augelli-Szafran et al., Inhibitors of acyl-CoA:cholesterol acyltransferase. 5. Identification and structure-activity relationships of novel α-ketoamides as hypocholesterolemic agents, J. Med. Chem. 36(20):2943-2949 (1993).
Austel and Kutter, Quant. Struct. Activity Relationships of Drugs, John G. Toplissm (ed.), Academic Press, pp. 437-496 (1983).
Bannai et al., Synthesis of Chemically Stable Prostacyclin Analogs, Tetrahedron 39(22):3807-3819 (1983).
Barnard et al., The Effect of Fluorine Substitution on the Physicochemical Properties and the Analgesic Activity of Paracetamol, J. Pharm. Pharmacol. 45(8):736-744 (1993).
Bass et al., Effect of Ring Fluorination of Epinephrine on Its Cardiovascular Adrenoceptor Activities, Eur. J. Pharmacol. 187(1):87-95 (1990).
Bergstrom and Shum, Synthesis and Characterization of a New Fluorine Substituted Nonionic Dinucleoside Phosphonate Analogue, P-Deoxy-P-(difluoromethyl)thymidyly1(3'-> 5')thymidine, J. Org. Chem. 53:3953-3958 (1988).
Bergstrom et al., 3',3'-Difluoro-3'-Deoxythymidine:Comparison of Anti-HIV Activity to 3'-Fluoro-3'-Deoxythymidine, J. Med. Chem. 35(18):3369-3372 (1992).
Bergstrom et al., Fluorine Substituted Analogs of Nucleosides and Nucleotides, Nucleos, Nucleot. 6(1 & 2):53-63 (1987).
Bey et al., Further Studies on the Inhibition of Monoamine Synthesis by Monofluoromethyldopa, Br. J. Pharmacol, 70(4):571-576(1980).
Black et al., Modulation of Carcinogenicity in 1,2, 3, 4-Tetrahydro-7,12-Dimethylbenz[a] Anthracene (THDMBA) by Fluorine Substitution: Crystal Structures of the 5- and 6- Fluoro Regioisomers, Carcinogenesis 13(8):1337-1343 (1992).
Blackburn et al., Isopolar vs isosteric Phosphonate Analogues of Nucleotides, Nucleos. Nucleot. 4(1 & 2):165-167 (1985).
Blackburn, Overview: The Seven Countries Study in Brief, http://www.epi.umn.edu/research/7countries/overview/shtm, downloaded on Aug. 10, 2010.
Blankenhorn and Hodis, Treating serum lipid abnormalities in high-priority patients, Postgrad. Med., 89(1):81-96 (1991).
Boersma et al., Role of Cytochromes P-450 and Flavin-Containing Monooxygenase in the Biotransformation of 4-Fluoro-N-Methylaniline, Drug Metab. Dispos. 21(2):218-230 (1993) (Abstract only).
Braun and Galle, A simple stereoselective synthesis of cholestrol absorption inhibitor (--)- SCH 48461, Synthesis 7:819-820 (1996).
Bravo et al., Synthesis and Pharmacological Evaluation of Enantiomerically Pure 4-Deoxy-4-Fluoromuscarines, J. Med. Chem. 35(17):3102-3110 (1992).
Brockman et al., Metabolism and Chemotherapeutic Activity of 9-β-D-Arabinofuranosyl-2-Fluoroadenine against Murine Leukemia L1210 and Evidence for Its Phosphorylation by Deoxycytidine Kinase, Cancer Res. 40(10):3610-3615 (1980).
Brodbeck et al., Fluorinated Aldehydes and Ketones Acting as Quasi-Substrate Inhibitors of Acetylcholinesterase, Biochim. Biophys. Acta. 567(2):357-369 (1979).
Brooks and Wiley, Evolution as Entropy. Towards a Unified Theory of Biology, D.L. Hull (editor) Second Edition (University of Chicago Press), Table of Contents (1968).
Brown and Bowden, New Twists on an Old Theme, Chem. Ind. 5:143-147 (1993).
Brown, Review of Clinical Studies of Fenofibrate in Combination with Currently Approved Lipid-Lowering Drugs, Cardiology 76(1):45-54 (1989).
Buffa and Peters, The in vivo Formation of Citrate Induced by Fluoroacetate and Its Significance, J. Physiol. 110(3-4):488-500 (1950).
Bugrim, "Early Prediction of Drug Metabolism and Toxicity: Systems Biology Approach and Modeling," Drug Discovery Today 9(3):127-135 (2004).
Buhler et al. Metabolism and Tumorigenicity of 7-, 8-,9-, and 10-Fluorobenzo(a) Pyrenes, Cancer Res. 42(11):4779-4783 (1982).
Burger, Progress in Drug Research. Fortschritte der Arneimittelforschung Progres des rescherches pharmaceutiques, Prog. Drug. Res. 37:287-371 (1991).
Burnett and Davis, "Chapter 6. Recent Advances in the Science and Treatment of Atherosclerosis," Annual Reports In Med. Chem., vol. 36, pp. 57-66 (Greenlee, Ed.), Academic Press (2001).
Burnett at al., 2-Azetidinones as Inhibitors of Cholesterol Absorption, J. Med. Chem. 37(12):1733-1736 (1994).
Burnett et al., Synthesis of Iodinated Biochemical Tools Related to the 2-Azetidinone Class of Cholesterol Absorption Inhibitors, Biorg. & Med. Chem. Letters 12:311-314 (2002).
Burnett, Asymmetric synthesis and absolute stereochemistry of cholesterol absorption inhibitor, SCH 48461, Tet. Letters 35(40):7339-7342 (1994).
Burnett, β-Lactam Cholesterol absorption inhibitors, Curr. Med. Chem. 11:1873-1887 (2004).
Burrier et al., The Effect of Acyl CoA: Cholesterol Acyltransferase Inhibition on the Uptake, Esterification and Secretion of Cholesterol by the Hamster Small Intestine. J. Pharmacol. Exp. Ther. 372(1): 156-163 (1995).
Bush and Mahesh Metabolism of 11-Oxygenated Steroids. 2. 2-Methyl Steroids, Biochem. J. 71(4):718-742 (1959).
Bush and Mahesh, Metabolism of 11-Oxygenated Steroids. 3. Some 1-Dehydro and 9 α-fluoro Steroids, Biochem. J. 93(2):236-255 (1964).
Butler and Gray, The Metabolism of Betamethasone, J. Endocrinol. 46(3):379-390 (1970).
Campbell et al., β-Lactamase Activity of Purified and Partially Characterized Human Renal Dipeptidase, J. Biol. Chem. 259(23):14586-14590 (1984).
Carpenter et al., Pharmacokinetics of Inhaled Anesthetics in Humans: Measurements During and After the Simultaneous Administration of Enflurane, Halothane, Isoflurane, Methoxyflurane, and Nitrous Oxide, Anesth. Analg. 65(6):575-582 (1986).

Carrell et al., Fluorocitrate Inhibition of Aconitase: Relative Configuration of Inhibitory Isomer by X-Ray Crystallography Science 170(965):1412-1414 (1970).
Cates, Calculation of drug solubilities by pharmacy students, Am. J. Pharm. Ed., 45:11-13 (1981).
Chen et al., Asymmetric Synthesis of Substituted 2-Azaspiro[3.5]nonan-1-ones: An Enantioselective Synthesis of the Cholesterol Absorption Inhibitor (+)-SCH 54016, J. Org. Chem. 61(23):8341-8343 (1996).
Chiba et al., Oxidative Metabolism of Omeprazole in Human Liver Microsomes: Cosegregation with S-Mephenytoin 4'- Hydroxylation, J. Pharmacol. Exp. Ther. 266(1):52-59 (1993).
Clader et al., 2-Azetidinone Cholesterol Absorption Inhibitors: Structure-Activity Relationships on the Heterocyclic Nucleus, J. Med. Chem. 39:3684-3693 (1996).
Clader, Ezetimibe and other Azetidinone Cholesterol Absorption Inhibitors, Curr. Topics in Med. Chem. 5(3):243-256 (2005).
Clader, Ezetimibe: Chemistry-Driven Drug Discovery in the Absence of a Defined Molecular Target Schering-Plough Research Institute Visio Presentation (slides) (2005).
Clader, The Discovery of Ezetimibe: A View from Outside the Receptor, J. Med. Chem. 47(1):1-9 (2004).
Claudi et al., Synthesis and Dopamine Receptor Affinities of 2-(4-Fluoro-3-Hydroxyphenyl) Ethylamine and N-Substituted Derivatives, J. Med. Chem. 33(9):2408-2412 (1990).
Curtis et al., Double-blind, placebo-controlled cross-over trial of cholestyramine an bezafibrate in the treatment of monogenic familial hypercholesterolaemia (FH), Atherosclerosis 68:271 (1987).
Davidson and Eastham, Acute Liver Necrosis Following Overdose of Paracetamol, Br. Med. J. 2(5512):497-499 (1966).
Davis et al., Species Differences in Hepatic Glutathione. Depletion, Covalent Binding and Hepatic Necrosis After Acetaminophen Life Sci., 14(11):2099-2109 (1974).
Davis et al., The hypercholesterolemic activity of the potent cholesterol absorption inhibitor SCH 58235 alone and in combination with HMG CoA reductase inhibitors, XII Int'l Symposium on Drugs Affecting Lipid Metabolism, Abstract, p. 62 (1995).
Davis et al., The Synergistic Hypocholesterolemic Activity of the Potent Cholesterol Absorption Inhibitor, Ezetimibe, in Combination With 3·Hydroxy-3·Methylglutaryl Coenzyme A Reductase Inhibitors in Dogs, Metabolism 50(10):1234-1241 (2001).
DeBernardis et al., Conformationally Defined Adrenergic Agents. 1. Design and Synthesis of Novel α2 Selective Adrenergic Agents: Electrostatic Repulsion Based Conformational Prototypes, J. Med. Chem. 28(10):1398-1404 (1985).
deGennes et al., Long-term (over 5 years) treatment of primary hyperlipidemia by fenofibrate alone or with cholestyramine, Treatment of Hyperlipoproteinemia, (Carlson and Olsson, eds.), Raven Press, NY, pp. 175-180 (1984).
Dembowski and Davidson, Statin and Ezetimibe Combination Therapy in Cardiovascular Disease. Curr. Opin. Endocrinol. Diabetes Obes. 16(2):183-188 (2009).
Development of new stereoisomeric drugs, May 1, 1992, http://www.fda.gov/Drugs/GuidanceComplianceRegulatoryInformation/Guidance/ucm122883.htm, downloaded Aug. 10, 2010.
Di Giulio, et al., Encapsulation of Ampicillin in Reverse-Phase Evaporation Liposomes: A Direct Evaluation by Derivative Spectrophotometry, Int. J. Pharm. 74:183-188 (1991).
Dodd et al., Metabolism and Pharmacokinetics of Selected Halon Replacement Candidates, Toxicol. Lett. 68(1-2):37-47 (1993).
Doherty et al., Design and Synthesis of Potent, Selective, and Orally Active Fluorine-Containing Renin Inhibitors, J. Med. Chem. 35(1):2-14 (1992).
Dolle et al., ATP-Citrate Lyase as a Target for Hypolipidemic Intervention. Sulfoximine and 3-Hydroxy-β-Lactam Containing Analogues of Citric Acid as Potential Tight-Binding Inhibitors, J. Med. Chem. 35(26):4875-4884 (1992).
Dorland's Illustrated Medical Dictionary, 30th Ed., W.B. Saunders & Co., Canada, p. 1513 (2003)—"prodrug".
Drazen et al., Cholesterol Lowering and Ezetimibe, N. Eng. J. Med. 358(14):1507-1508 (2008).
Drug Information, Baycol Information, Center for Drug Evaluation and Research, 2001, http://www.fda.gov/cder/drug/infopagelbaycol/default.htm, downloaded Apr. 15, 2009.
Dugar et al., Amides of Piperidine, Morpholine and Piperazine Substituted 1-Phenylethylamines: Inhibitors of AcylCoA:cholesterol Acyltransferase (ACAT) Activity in vitro and in vivo, Bioorg. Med. Chem., 3(9):1231-1236 (1995).
Dugar et al., Gamma-lactams and related compounds as cholesterol absorption inhibitors: homologs of the beta-lactam cholesterol absorption inhibitor SCH 48461, Bioorg. Med. Chem. Lett. 5(24)2947-2952 (1995).
Dugar et al., Metabolism and structure activity data based drug design; discovery of (-) SCH 53079 an analog of the potent cholesterol absorption inhibitor (-) SCH 48461, Bioorg. Med. Chem. Lett. 6(11):1271-1271 (1996).
Dugar et al., N-Oleayl-l,2,3,4-Tetrahydroisoquinolines as Conformationally Restricted Inhibitors of Acyl-CoA:Cholesterol Acyl Transferase (ACAT), Bioorg. Med. Chem. Lett., 3(4):571-576 (1993).
Dugar et al., Substituted 2-Azaspiro[5.3]nonan-1-ones as Potent Cholesterol Absorption Inhibitors: Defining a Binding Conformation for SCH 48461, J. Med. Chem. 38(25):4875-4877 (1995).
DuJovne et al., Probucol with colestipol in the teatment of hypercholesteolemia, Ann. Intern. Med. 100:477-482 (1984).
Dujovne et al., Reduction of LDL Cholesterol in Patients with Primary Hypercholesterolemia by SCH 48461: Results of a Multicenter Dose-Ranging Study, J. Clin Pharmacology 41:70-78 (2001) (Abstract only).
Duschinsky et al., The Synthesis of 5-Fluoropyrimidines, J. Am. Chem. Soc. 79:4559-4560 (1957).
Dysken et al., Fluphenazine Pharmacokinetics and Therapeutic Response, Psychooharmacology 73:205-210 (1981).
East et al., Combination drug therapy for treatment of patients with familial combined hyperlipidemia resulting in combined hypertriglyceridemia and hypercholesterolemia, Arteriosclerosis 6:544A (1986).
Eger et al., Is Enfiurane Hepatotoxic? Anesth. Analg. 65(1)21-30 (1986).
El Masry, Studies in Detoxication. 69. The metabolism of alkylbenzenes: n-propylbenzene and n-butylbenzene with further observations of ethylbenzene, Biochem J. 64(1):50-56 (1956).
Elliott, The Role of Fluorine in the Development of Central Nervous System Agents in Biomedicinal Aspects of Fluorine Chemistry (R. Fuller and Y. Kobayashi, eds.), Elsevier Biomedical Press, New York, pp. 55-74, (1982).
Erlenmeye et al., Justus Liebigs Annalen der Chemie, Liepzig, C.F. Wintersche Verladshandluna, pp. 51-123 (1907), vol. 356.
Filler, Organofluorine Chemicals and their Industrial Applications (Banks, R. E, ed.), Ellis Horwood Ltd. Publishers, Chichester, Ch. 6 Fluorine-containing Drugs (1979).
Frey and Frey, Urinary 6 β-Hydroxyprednisolone Excretion Indicates Enhanced Prednisolone Catabolism, J. Lab. Clin. Med. 101(4):593-604 (1983).
Fried and Sabo, 9α-Fluoro Derivatives of Cortisone and Hydrocortisone, J. Am. Chem. Soc. 76:1455-1456 (1954).
Fried et al., 10,10-Difluoro-13-Dehydroprostacyclin: A Chemically and Metabolically Stabilized Potent Prostacyclin, J. Med. Chem. 23(3):234-237 (1980).
Fried et al., Synthesis and Properties of 7,7-Difluoro Derivatives of the 2,6-Dioxa[3.1.1] bicycloheptane Ring System Present in Thromboxane $A_2$, J. Am. Chem. Soc. 106:3871-3872 (1984).
Garcia-Calvo et al., The target of ezetimibe is Niemann-Pick C1-like 1 (NPC1L1), Proc. Natl. Acad. Sci. USA 102(23):8132-8137 (2005).
Gazi et al., Effect of Ezetimibe in Patients Who Cannot Tolerate Statins or Cannot Get to the Low Density Lipoprotein Cholesterol Target Despite Taking a Statin, Curr. Med. Res. Opin. 23(9):2183-92 (2007).
Generic Pharmaceutical Association. Facts at a Glance. http://www.gphaonline.org/about-gpha/about-generics/facts © 2010.
Georg and Gill, Stereo—and Enantio-controlled synthesis of chiral intermediates for the total synthesis of thienaycin and related β-Lactam antibiotics from 3-hydroxybutyrates, J. Chem. Soc., Chem. Comm. pp. 1433-1435 (1985).

Georg et al., An Impoved Mehod For The Stereoselective Synthesis Of B-Lactams From Carboxylic Acids And Imines, Tet. Lett. 32(5):581-584(1991).
Goldstein and Brown, Cholesterol: A Century of Research. HHMI Bulletin, vol. 16, No. 3, Sep. 2003.
Gootz et al., "Pharmacokinetic Studies in Animals of a New Parenteral Penem CP-65,207 and its Oral Prodrug Ester," J. Antibiot. 43(4):422-432 (1990).
Gotto, Over-The-Counter Statins Are Worth Considering in Primary Prevention of Cardiovascular Disease, Circulation 114:1310-1314 (2006).
Grundy et al., Influence of combined therapy with mevinolin and interruption of bile-acid reabsorption on low density lipoproteins in Heterozygous familial hypercholesterolemia, Ann. Intern. Med., 103:339-343 (1985).
Guengerich and MacDonald, Chemical Mechanism of Catalysis by Cytochromes P-450: A Unified View, Acc. Chem. Res. 17:9-16 (1984).
Halloran et al., An Examination of the Importance of 24-Hydroxylation to the Function of Vitamin D During Early Development, Endocrinology 108(6):2067-2071 (1981).
Hansch and Leo, Cluster Analysis and the Design of Congener Sets, in Substituent Constants for Correlation Analysis in Chemistry and Biology, John Wiley & Sons, NY, Ch. 6, 48-54 (1979).
Harris and Anders, Metabolism of the Hydrochlorofluorocarbon 1,2-Dichloro-1,1-Difluoroethane, Chem. Res. Toxicol. 4(2):180-186 (1991).
Harris et al., Pentahaloethane-Based Chlorofluorocarbon Substitutes and Halothane: Correlation of In Vivo Hepatic Protein Trifluoroacetylation and Urinary Trifluoroacetic Acid Excretion with Calculated Enthalpies of Activation, Chem. Res. Toxicol. 5(5):720-725 (1992).
Harris et al., Tissue Acylation by the Chlorofluorocarbon Substitute 2,2-Dichloro-1,1,1-Trifluoroethane, Proc. Natl. Acad. Sci. USA 88(4):1407-1410 (1991).
Harrison et al., Metabolic Defluorination of 5-Fluoro-Amodiaquine in the Rat, Br. J. Clin. Pharmacol. 34:148P-149P (1992).
Hart and Ha, The Ester Enoiate-Imine Condensation Route to β-Lactams, Chem. Rev. 89(7):1447-1465 (1989).
Hecht et al., Comparative Mutagenicity, Tumor-Initiating Activity, Carcinogenicity, and In Vitro Metabolisrn of Fluorinated 5-Methylchrysenes, J. Natl. Cancer Inst. 63(3):855-861 (1979).
Hecht et al., Reduction of Tumorigenicity and of Dihydrodiol Formation by Fluorine Substitution in the Angular Rings of Dibenzo(a,i) Pyrene, Cancer Res. 41(11 Pt. 1):4341-4345 (1981).
Heidelberger et al., Fluorinated Pyrimidines, a New Class of Tumour-Inhibitory Compounds, Nature 179(4561):663-666 (1957).
Heidelberger, The Nucleotides of Fluorinated Pyrimidines and Their Biological Activities, in Carbon-Fluorine Compounds: Chemistry, Biochemistry and Biological Activities, (K. Elliot, ed.), Associated Scientific Publishers, Amsterdam, pp. 125-140 (1972).
Herper, Behind Zetia's curtain, http://www.forbes.com/2002/10/31/cx, downloaded Apr. 29, 2010.
High Blood Cholesterol: What you need to know, http://www.nhlbi.nih.gov/health/public/heart/chol/wyntk.htm—downloaded Aug. 10, 2010.
Hitt et al., Metabolism of Isoflurane in Fischer 344 Rats and Man, Anesthesiology 40(1):62-67(1974).
Hobbs et al., Pharmacokinetics of prazosin in man, J. Clin. Pharmacol. 18(8):402-6 (1978) Abstract only.
Hodgkins and Megarity, A Study of Benzyl Free Radical and Substituted Benzyl Free Radicals, J. Amer. Chem. Soc. 87(23):5322-5326 (1965).
Hoeg et al., The Effects of Mevinolin and Neomycin Alone and in Combination on Plasma Lipid and Lipoprotein Concentrations in Type II Hyperlipoproteinemia, Atherosclerosis 60:209-214 (1986).
Hoeg, Combination Drug Therapy, in Drug Treatment of Hyperlipidemia, Ch. 10, (Rifkind, Ed.), Marcel Dekker, Inc., pp. 215-231 (1991).
Huberman and Slaga, Mutagenicity and Tumor-Initiating Activity of Fluorinated Derivatives of 7,12-Dimethylbenz(a)Anthracene, Cancer Res. 39(2 Pt. 1):411-414 (1979).
Hughes and Saunders, Enzymatic Rupture of a C-F Bond, Chem. Ind. (London) 1265 (1954).
Humphrey and Smith, Role of metabolism ad pharmacokinetic studies in the discovery of new drugs—present and future perspectives, Xenobiotica 22(7):743-755 (1992).
Husain et al., Fluoride Elimination from Substrates in Hydroxylation Reactions Catalyzed by p-Hydroxybenzoate Hydroxylase, J. Biol. Chem. 255(9):4189-4197 (1980).
Illingworth and Bacon, Hypolipidemic Effects of HMG-CoA Reductase Inhibitors in Patients with Hypercholesterolemia, Am. J. Cardiol. 60(12):33g-42g (1987).
Illingworth et al., Colestipol plus nicotinic acid in treatment of heterozygous familial hypercholesterolaemia, Lancet 1(8215):296-298 (1981).
Illingworth et al., Long-Term Experience with HMG-CoA Reductase Inhibitors in the Therapy of Hypercholesterolemia, Atherosclerosis Revs. 18:161-187 (1988).
Illingworth, Mevinolin Plus Colestipol in Therapy for Severe Heterozygous Familial Hypercholesterolemia, Ann. Intern. Med. 101:598-604 (1984).
Intelligence.360, Global Pharmaceutical Perspectives, Making sense of the year—and what lies ahead—in a time of unprecedented challenge and opportunity, 2006.
Jamali, Stereochemically Pure Drugs—An Overview, Drug Stereochemistry, in Analytical Methods and Pharmacology. Ch. 14, pp. 375-384 (1993).
Jerina et al., Carcinogenicity of Benzo[a]Pyrene, in Drug Design and Adverse Reactions (II. Bundgaard, P. Juul, and H. Kafod, eds.), Academic Press, New York, pp. 261-275 (1977).
Jeu and Cheng, Pharmacology and Therapeutics of Ezetimibe (SCH 58235), a Cholesterol-Absorption Inhibitor, Clin. Ther. 25(9):2352-2387 (2003).
Jones et al. Biotransformation and Hepato-Renal Function in Volunteers After Exposure to Desflurane (1-653), Br. J. Anaesth. 64(4):482-487 (1990).
Kane et al., Normalization of low-density-lipoprotein levels in heterozygous familial hypercholesterolemia with a combined drug regimen, New Engl. J. Med. 304(5):251-258 (1981).
Kastelein et al., Simvastatin with or without ezetimibe in Familial Hypercholesterolemia, New Eng. J. Med. 358(14):1431-43 (2008).
Kastelein, Statin Therapy with Ezetimibe or Niacin in High-Risk Patients, New Eng. J. Med., 361:2180-2183 (2009).
Kaufman, The enzymic conversion of 4-fluorophenylalanine to tyrosine, Biochim, Biophys. Acta 51:619-621 (1961).
Kawase et al., Mechanism of Autoxidation of 5,7-Dihydroxytryptamine: Effect of Fluorine Substitution at Positions 4 and/or 6, Chem. Pharm, Bull 38(11):2939-2946 (1990).
Kenna et al., Metabolic Basis for a Drug Hypersensitivity: Antibodies in Sera From Patients With Halothane Hepatitis Recognize Liver Neoantigens that Contain the Trifluoroacetyl Group Derived from Halothane, J. Pharmacol. Exp. Ther. 245(3):1103-1109 (1988).
Kimura et al., Structure-activity relationship of a series of phenylureas linked to 4-phenylimidazole. Novel potent inhibitors of acyl-CoA:cholesterol O-acyltransferase with antiatherosclerotic activity. 2., J. Med. Chem. 36(11):1641-1653 (1993).
Kimura et al., Structure-Activity Relationship of N-[2-(Dimethylamino)-6-[3-(5-Methy1-4- Phenyl-1H-Imidazol-1-yl)Propoxy]Phenyl]-N'-Pentylurea and Analogues. Novel Potent Inhibitors of Acyl-CoA: Cholesterol O-Acyltransferase with Antiatherosclerotic Activity, J. Med. Chem. 36(11):1630-1640 (1993).
Kirk et al., Syntheses and adrenergic agonist poperies of ring-fluorinated isoproterenols, J. Med. Chem. 25(6):680-684 (1982).
Kirk et al., Synthesis and adrenergic activity of ring-fluorinated phenylepherines, J. Med. Chem. 29(10):1982-1988 (1986).
Kirkup et al., (-)-SCH 57939: Synthesis and pharmacological properties of a potent, metabolically stable cholesterol absorption inhibitor, Bioorg. Med. Chem. Lett. 6(17):2069-2072 (1996).
Kitteringham et al., Conjugation of dinitrofluorobenzene to plasma proteins in vivo in the rat, Drug Metab. Dispos. 20(5):625-631 (1992).

Kobayashi and Taguchi, Fluorinated Vitamin $D_3$ Analogs Syntheses and Biological Activites, in Biomedical Aspects of Fluorine Chemistry (R. Filler and Y. Kobayashi, eds.), Associated Scientific Publishers, Amsterdam, pp, 33 (1982).
Koblin et al., I-653 Resists Degradation in Rats, Anesth. Analg. 67(6):534-538 (1988).
Kollonitsch et al., Selective Inhibitors of biosynthesis of Aminergic Neurotransmitters, Nature 274(5674):906-908 (1978).
Kong et al., Comparisons of Anti-Human Immunodeficiency Virus Activites, Cellular Transport, and Plasma and Intracellular Pharmacokinetics of 3'-Fluoro-3'-Deoxythymidine and 3'-Azido-3'-Deoxythymidine, Antimicrob. Agents Chernother, 36(4):808-818 (1992).
Kripalani et al., Metabolism of Triamcinolone Acetonide-21-Phosphate in Dogs, Monkeys, and Rats, J. Pharm. Sci. 64(8):1351-1359 (1975).
Kroemer HK, Mikus G, Kronbach T, Meyer UA, Eichelbaum M. In vitro characterization of the human cytochrome P-450 involved in polymorphic oxidation of propafenone. Clin Pharmacol Ther. 1989;45:28-33.
Kropp et al., Meabolism of Thienamycin and Related Carbapenem Antibiotics by the Renal Dipeptidase, Dehydropeptidase-I Antimicrob. Agents Chemother. 22(1):62-70 (1982).
Kuo et al., Effects of Combined Probucol-Colestipol Treatment for Familial Hypercholesterolemia and Coronary Artery Disease, Am. J. Cardiol. 57:43H-48H (1986).
Landsberg, Can Entropy and "Order" Increase Together? Physics Letters 102A(4):171-173 (1984).
Landsberg, Is Equilibrium Always an Entropy Maximum? J. Stat. Physics 35(1/2):159-169 (1984).
Lees et al., Therapy of Hypercholesterolemia with Mevinolin and Other Lipid-Lowering Drugs, Arteriosclerosis 6:544 (1986).
Lehninger et al., Principles of Biochemistry, Second Edition (Worth Publishers, NY), Table of Contents (1993).
Li et al., Catechol Formation of Fluoro—and Bromo-Substituted Estradiols by Hamster Liver Microsomes. Evidence for Dehalogenation, Mol. Pharmacol. 27(5):559-565 (1985).
Liehr, 2-Fluoroestradiol, Separation of Estrogenicity from Carcinogenicity, Mol. Pharmacol. 23(2)278-281 (1983).
Lien, Structure-Absorption-Distribution Relationships: Significance for Drug Design, in Drug Design, vol. V, (Ariëns, Ed.) Academic Press, NY, pp. 81-132 (1975).
Lloyd-Jones et al., Heart Disease and Stroke Statistics—2009 Update. A Report from the American Heart Association Statistics Committee and Stroke Statistics Subcommittee, Circulation, pp. e22-e181 (Jan. 27, 2009) (downloaded from circ.ahajournals.org on Apr 14, 2009).
Low and Castagnoli, Drug Biotransformations, in Burger's Medicinal Chemistry, 4th Ed., Part I, The Basis of Medicinal Chemistry, (Wolff, ed.), John Wiley & Sons, NY, pp. 108-226 (1980).
Low and Castagnoli, Metabolic Changes of Drugs and Related Organic Compounds, in Wilson and Gisvolds Textbook of Organic Medicinal and Pharmaceutical Chemistry, 9th Ed., Ch. 3, (Delgado and Remers, Eds.), pp. 45-127 (1991).
Mabuchi et al., Reduction of serum cholesterol in heterozygous patients with familial hyperchalesterolemia, New Eng. J. Med, 308:609-613 (1983).
Malloy et al., Complementarity of Colestipol, Niacin, and Lovastatin in Treatment of Severe Familial Hypercholesterolemia, Ann. Intern. Med., 107:616-623 (1987).
Mann et al., Probucol in patients resistant to the lipid lowering effects of cholestyramine, Lancet Feb. 21;1(8217):450-451 (1981).
Mann, Modern Methods for the Introduction of Fluorine into Organic Molecules: An Approach to Compounds with Altered Chemical and Biological Activities, Chem. Soc. Rev. 16:381-436 (1987).
Manuel et al., Burden of cardiovascular disease in Canada, Can J. Cardiol. 19(9):997-1004.
March, *Advanced Organic Chemistry, Reactions, Mechanisms, and Structure, Fourth Edition* (Wiley 1992) University of Michigan, Table of Contents.
Masood et al., 2'-Fluoro-2,3'-Dideoxyarabinosyladenine: A Metabolically Stable Analogue of the Antiretroviral Agent 2',3'-Dideoxyadenosine, Mol. Pharmacol, 37(4):590-596 (1990).
Matthes et al., Phosphorylation, Anti-HIV Activity and Cytotoxicity of 3'-Fluorothymidine, Biochem. Biophys. Res. Commun. 153(2):825-831 (1988).
Mauro and Tuckerman, Ezetimibe for Management of Hypercholesterolemia, Ann. of Phormacother. 37:839-848 (2003).
Mazze et al., Inorganic Fluoride Nephrotoxicity: Prolonged Enflurane and Halothane Anesthesia in Volunteers, Anesthesiology 46(4):265-271 (1977).
Mazze et al., Methoxyflurane Metabolism and Renal Dysfunction: Clinical Correlation in Man, Anesthesiology 35(3):247-252 (1971).
Mazze et al., Renal Effects and Metabolism of Isoflurane in Man, Anesthesiology 40(6):536-542 (1974).
McCarthy et al., 4',5'-Unsaturated 5'-Fluoroadenosine Nucleosides: Potent Mechanism-Based Inhibitors of S-Adenosyl-L-Homocysteine Hydrolase, J. Am. Chem. Soc. 111:1127-1128 (1989).
McCarthy, New Approaches to Atherosclerosis: An Overview, Med. Res. Rev. 13(2):139-159 (1993).
McGill et al., Natural History of Human Atherosclerotic Lesions, Atherosclerosis and its Origin, (Sandler and Bourne, eds.), pp. 39-65 (1963).
McKittrick et al., Stereoselective synthesis and biological activity of cis azetidinones as cholesterol absorption inhibitors, Bioorg. & Med. Chem Lett. 6(16):1947-1950 (1996).
McKittrick et al., Synthesis of C3 Heteroatom-Substituted Azetidinones that display potent cholesterol absorption inihibitory activity, J. Med. Chem. 41(5):752-759 (1998).
Merck Manual of Diagnosis & Therapy, 25th Ed., Berkow (ed.), Merck & Co., Inc., at p. 2430.—"pharmacokinetics" (1987).
Merriam-Webster's New Collegiate Dictionary, 8th ed., Merriam-Webster, Inc.—"administering" (1981).
Michalek et al., Pharmacokinetics of TCDD in veterans of Operation Ranch Hand; 10-year-follow-up, Journal of Toxicology and Environmental Health 52(6):557-558 (1997).
Miller and Miller, The Carcinogenicity of Fluoro Derivatives of 10-Methyl-1,2-Benzanthracene. I. 3- and 4'-Monofluoro Derivatives, Cancer Res. 20:133-137 (1960).
Minagawa et al., Identification and Quantification of 6 β-Hydroxydexamethasone as a Major Urinary Metabolite of Dexamethasone in Man, Steroids 47(2-3):175-188 (1986).
Molgaard et al., Long-term Efficacy and Safety of Simvastatin Alone and in Combination Therapy in Treatment of Hypercholesterolaemia, Atherosclerosis 91:S21-S28 (1991).
Montgomery et al., Synthesis and Biological Evaluation of 2-Fluoro-8-Azaadenosine and Related Compounds, J. Med. Chem. 26(10):1483-1489 (1983).
Morgan et al., Oxidative Dehalogenation of 2-Fluoro-17 α-Ethynyloestradiol in vivo. A Distal Structure-Metabolism Relationship of 17 α-Ethynylation, Biochem. Pharmacol. 44(9):1717-1724 (1992).
Morgan et al., The Metabolism of 2- and 4-Fluoro-17 β-Oestradiol in the Rat and its Implications for Oestrogen Carcinogenesis, Biochem. Pharmacol. 43(5):985-993 (1992).
Morinelli et al., Difluorothromboxane $A_2$ and Stereoisomers: Stable Derivatives of Thromboxane $A_2$ with Differential Effects on Platelets and Blood Vessels, Proc. Natl. Acad. Sci. U.S.A. 86(14):5600-5604 (1989).
Murphy et al., Some Aspects of the Metabolism and Disposition of Betamethasone, Acta. Endocrinol. 45:498-508 (1964).
Murray-Rust, Intermolecular Interactions of the C-F Bond: The Crystallographic Environment of Fluorinated Carboxylic Acids and Related Structures, J. Am. Chem. Soc. 105:3206-3214 (1993).
Nagabhushan, T. L., Kandasamy, D., Tsai, H., Turner, W. N. & Miller, G. H. (1980). Novel class of chloramphenicol analogs with activity against chloramphenicol-resistant and chloramphenicol-susceptible organisms. In *Current Chemotherapy and Infectious Disease, vol. 1, Proceedings of the 11th International Congress of Chemotherapy and the 19th* Interscience Conference on Antimicrobial Agents and Chemotherapy, Boston, MA, 1979 (Nelson, J. D. & Grassi, C, Eds), pp. 442-443. American Society for Microbiology, Washington, DC.
Napoli et al., 1 α-hydroxy-25-fluorovitamin $D_3$: a potent analogue of 1 α,25-dihydroxyvitamin $D_3$, Biochemistry 17(12):2387-2392 (1978).

Napoli et al., 1-Fluorovitamin D3, a vitamin D3 analogue more active on bone-calcium mobilization than on intestinal-calcium transport, Biochemistry 18(9):1641-1646 (1979).
Negishi et al., Palladium-Catalyzed Acylation of Oganozincs and Other Organometalics as a Convenien Route to Ketones,Tetrahedron Lett. 24(47):5181-5184 (1983).
Nelson et al., Does Ammonia Hydrogen Bond? Science 238(4834): 1670-1674 (1987).
Nikkari et al., The hyperlipidemic hamster as an atherosclerosis model, Artery 18(6)285-290 (1991).
Oguni et al., Stereoselective Synthesis of β-Lactam Derivatives by Ultrasound Promoted Reformatskii Reaction, Chem. Abstracts No. 17, vol. 106:138174y (1987).
Packard et al., Combined drug therapy for familial hypercholesterolemia, Artery 7(4):281-289 (1980).
Park and Kitteringham, Effects of fluorine substitution on drug metabolism: pharmacological and toxicological implications, Drug Metab. Reviews 26(3):605-643 (1994).
Patani and LaVoie, Bioisosterism: A Rational Approach in Drug Design, Chem. Rev. 96(8):3147-3176 (1996).
Peters et al., Biochemistry of Fluoroacetate Poisoning: The Isolation and Some Properties of the Fluoroticarboxylic Acid Inhibitor of Citrate Metabolism, Proc. Roy. Soc. B140:497-507 (1952).
Peters, Some Metabolic Aspects of Fluoroacetate Especially Related to Fluorocitrate, in Carbon Fluorine Compounds: Chemistry, Biochemistry & Biological Activies, A Ciba Foundation Symposium, (Elsevier Excerpta Medica North-Holland), Associated Scientific Publishers, Amsterdam, london, New York, pp. 55-76 (1972).
Pinedo and Petes, Fluorouracil: Biochemistry and Pharmacology, J. Clin. Oncol. 6(10):1653-1664 (1988).
Pohl et al., Neoantigens associated with halothane hepatitis, Drug Metab. Rev. 20(2-4):203-217 (1989).
Poston and Foreyt, Scientific and Legal Issues Fenfluramine/Dexfenfluramine Litigation, Tex. Med. 96(2):48-56 (2000).
Regårdh et al., Plasma Levels and β-Blocking Effect of Hydroxymetoprolol—Metabolite of Metopropol in the Dog, J. Pharm. and Biopharm. 7(5):471-479 (1979) (Abstract only).
Reifenrath et al., Synthesis and Biological Activity of Fluoroalkylamine Derivatives of Narcotic Analgesics, J. Med. Chem. 23(9):985-990 (1980).
Rekker and Mannhold, Calculation of Drug Lipophilicity—The Hydrophobic Fragmental Constant Approach (Jointly by VCH Verlagsgesellschaft, Weinhehn (Federal Republic of Germany) and VCH Publishers Inc., New York (USA)), Table of Contents (1992).
Report of the National Cholesterol Education Program Expert Panel on Detection, Evaluation, and Treatment of High Blood Cholesterol in Adults, Arch. Intern. Med. 148:36-69 (1988).
Resnati, Aspects of the Medicinal Chemistry of Fluoroorganic Compounds. Part I, II Farmaco. 45(10):1043-1066 (1990).
Resnati, Aspects of the Medicinal Chemistry of Fluoroorganic Compounds. Part II, II Farmaco. 45(11):1137-1167 (1990).
Rice et al., Fluorine Probes for Investigating the Mechanism of Activation of Indeno[1,2,3-cd] Pyrene to a Tumorigenic Agent, Carcinogenesis 11(11):1971-1974 (1990).
Ridker et al., Reduction in C-reactive protein and LDL cholesterol and cardiovascular event rates after initiation of Rosuvastatin: a prospective study of the JUPITER trial, Lancet 373(9670):1175-82 (2009).
Ridker et al., Rosuvastatin to Prevent Vascular Events in Men and Women with Elevated C-Reactive Protein, New Eng. J. Med., 359(21):2195-2207 (2008).
Rietjens and Vervoort, Bioactivation of 4-Fluorinated Anilines to Benzoquinoneimines as Primary Reaction Products, Chem. Biol. Interact. 77(3):263-281 (1991).
Rifai et al., Clinical Chemistry Journal Has Contributed to Progress in Lipid and Lipoprotein Testing for Fifty Years, Clin. Chem. 50:10:1861-1870 (2004).
Roman et al., Renal Tubular Site of Action of Fluoride in Fischer 344 Rats, Anesthesiology 46(4):260-264 (1977).
Rosenblum et al., Discovery of 1-(4- Fluorophenyl)-(3R)43-(4-Fluorophenyl)-(3S)-Hydroxypropylk-(4S)-(4- Hydroxyphenyl)-2-Azetidinone (SCH 58235), A Designed, Potent, Orally Active Inhibitor of Cholesterol Absorption, J. Med. Chem. 41(6):973-980 (1998).
Rosenblum et al., Discovery of SCH 58235, a potent orally active inhibitor of cholesterol absorption, XII International Symposium on Drugs Affecting Lipid Metabolism, Abstract, p. 61 (1995).
Roth et al., Inhibitors of Acyl-CoA: Cholesterol Acyltransferase. I. Identification and Structure-Activity Relationships of a Novel Series of Fatty Acid Anilide Hypocholesterolemic Agents, J. Med. Chem. 35(9):1609-1617 (1992).
Sandberg and Slaunwhite, Differences in Metabolism of Prednisolone-$C^{14}$ and Cortisol-$C^{14}$, J. Clin. Endocrinol. Metab. 17(9):1040-1050 (1957).
Scandinavian Simvastatin Survival Study Group, Randomised Trial of Cholesterol Lowering in 4444 Patients with Coronary Heart Disease: The Scandinavian Simvastatin Survival Study (4S), Lancet 344(8934):1383-1389 (1994).
Secrist et al., 2-Fluoroformycin and 2-Aminoformycin, Synthesis and Biological Activity, J. Med. Chem. 28(11):1740-1742 (1985).
Serway, Physics For Scientists & Engineers, Third Edition, (Updated Version), vol. 1, Saunders Golden Sunburst Series (Saunders College Publishing and Harcourt Brace College Publishers, Philadelphia), Table of Contents (1992).
Shankar et al., Synthesis of an Optically Pure 3-Unsubstituted β-Lactam Using an Asymmetric Reformatsky Reaction and its Conversion to Cholesterol Absorption Inhibitors, Tet. Lett. 37(24),4095-4098 (1996).
Shetty and Nelson, Chemical Aspects of Metoprolol Metabolism. Asymmetric Synthesis and Absolute Configuration of the 3-[4-(1-Hydroxy-2-methoxyethyl)phenoxy]-1-(isopropylamino)-2-propanols, the Diastereomeric Benzylic Hydroxylation Metabolites, J. Med. Chem. 31(1):55-59 (1988).
Silverman, Lead Modification: Drug Design and Development, in The Organic Chemistry of Drug Design and Drug Action, 2nd Ed., Sec. 2.2, pp. 29-32 (2004).
Sliskovic and White, Therapeutic Potential of ACAT Inhibitors as Lipid Lowering and Anti-Atherosclerotic Agents, Trends Pharmacol. Sci. 12:194-199 (1991).
Sommariva et al., Probucol and cholestyramine combination in the treatment of severe hypercholesterolemia, Int. J. Clin. Pharmacol, Ther. Taxicol., 24(9):505-510 (1986).
Ståhle and Ljungdahl-Ståhle, Pharmacokinetics and Extracellular Distribution to Blood, Brain, and Muscle of Alovudine (3'-Fluorothymidine) and Zidovudine in the Rat Studied by Microdialysis, J. Acquir. Immune. Defic. Syndr. 6(5):435-439 (1993).
Stary et al., A Definition of Initial, Fatty Streak, and Intermediate Lesions of Atherosclerosis. A Report From the Committee on Vascular Lesions of the Council on Arteriosclerosis, American Heart Association, Arterioscler. Thromb. Vasc. Biol. 14:840-856 (1994).
Stedman's Medical Dictionary, www.medilexicon.comimedicaldictionary.php. Lippincott Williams & Wilkins (2006)—"prodrug".
Stein et al., Achieving Lipoprotein Goals in Patients at High Risk with Severe Hypercholesterolemia: Efficacy and Safety of Ezetimibe Co-administered with Atorvastatin. Am Heart J 2004; 148(3),447-55.
Stein et al., Lavastatis alone and in combination with resin in severe primary hypercholesterolemia, Arteriosclerosis 7:513A (1985).
Stein et al., Treatment of severe familial hypercholesterolemia with Lovastatin, resin and niacin, Arteriosclerosis 7:517A (1987).
Steinberg, An interpretive history of the cholesterol controversy: part 1, J. Lipid Res. 45:1583-1593 (1994).
Subcommittee on the National Halothane Study, "Summary of the National Halothane Study" J. Am. Med. Assoc. 197(10):121-134 (1966).
Sybertz et al., SCH 48461, a novel inhibitor of cholesterol absorption, Atherosclerosis X, Workshop Abstracts, p. 89, Montreal, Oct. 10, 1994.
Tagg et al., Metabolic studies of tolbutamide in the rat, Biochemical Pharmacology 16(1):143-53 (1967).
Takahashi et al., Crystal structure of the covalent complex formed by a peptidyl-α-α-difluoro-β-keto amide with porcine pancreatic elastase at 1.78Å resolution, J. Am. Chem. Soc. 111:3368-3374 (1989).

Tanaka et al., 26,26,26,27,27,27-Hexafluoro-1,25-Dihydroxyvitarnin $D_3$: A Highly Potent, Long-Lasting Analog of 1,25- Dihydroxyvitamin $D_3$, Arch. Biochem. Biophys. 229(1):348-354 (1984).
Taylor et al., The metabolic fate of prazosin, Xenobiotica 7(6):357-64 (1977).
Taylor, Allen J. et al., Extended Release Niacin or Ezetimibe and Carotid Intima-Media Thickness, New Engl. J. Med. 361(22)2113-2122 (2009).
Thornber, Isosterism and molecular modification in drug design, Chem. Soc. Review, 18(4),563-580 (1979).
Thummel et al., Human Liver Microsomal Enflurane Defluorination Catalyzed by Cytochrome P-450 2E1 Drug Metab. Dispos. 21:350-357 (1993).
Tidwell, Thomas T., Schiff Bases, and a Century of β-Lactam Synthesis, Angew. Chem. Int. Ed. 47:1016-1020 (2008).
Tingle et al., Influence of Glutathione Conjugation on the Immunogenicity of Dinitrophenyl Derivatives in the Rat, Int. Arch. Allergy Appl. Immunol. 91(2):160-165 (1990).
Tocco et al., Physiological Disposition and Metabolism of 5-(2',4' -Difluorophenyl)Salicyclic Acid, a New Salicylate, Drug Metab. Dispos. 3(6):453-466 (1975).
Topliss and Martin, Utilization of Operational Schemes for Analog Synthesis in Drug Design, in Drug Design (Ariens, ed.), ch. 1, pp. 1-21 (1975).
Topliss, Utilization of operational schemes for analog synthesis in drug design, J. Med. Chem. 15(10):1006-1011 (1972).
Trivedi et al., Inhibitors of Acyl-CoA: Cholesterol Acyltransferase (ACAT). 7. Development of a Series of Substituted N-Phenyl-N-[(1-Phenylcyclopentyl) Methyl]Ureas with Enhanced Hypocholesterolemic Activity, J. Med. Chem. 37(11):1652-1659 (1994).
Tsushima et al., Fluorine-Containing Amino Acids and Their Derivatives, 4. Synthesis and Antibacterial Activity of Threo and Erythro 1-Fluorodehydroxylated Chloramphenicol Analogues, J. Med. Chem. 28(2):253-256 (1985).
van Heek et al., Comparison of the activity and disposition of the novel cholesterol absorption inhibitor, SCH58235, and its glucuronide, SCH60663, British J. Pharm, 129:1748-1754 (2000).
van Heek et al., Ezetimibe potently inhibits cholesterol absorption but does not affect acute hepatic or intestinal cholesterol synthesis in rats, British J. Pharm. 138:1459-1464 (2003).
van Heek et al., In Vivo Metabolism-Based Discovery of a Potent Cholesterol Absorption Inhibitor, SCH58235, in the Rat and Rhesus Monkey through the Identification of the Active Metabolites of SCH4846I, J. Pharm. and Exp. Ther. 283(1):157-163 (1997).
van Heek et al., Isolation and identification of the active metabolite(s) of SCH48461 and possible in vivo mechanism of action for their inhibition of cholesterol absorption, XII Int'l Symp. ON Drugs Affecting Lipid Metabolism, Nov. 7. 1995, Houston, TX.
van Heek et al., The cholesterol absorption inhibitor, ezetimibe, decreases diet-induced hypercholesterolemia in monkeys, Eur. J. Pharmacol. 415(1):79-84 (2001).
Velican and Velican, Coronary arteries in children up to the age of ten years, II. Intimal thickening and its role in atherosclerotic involvement, Med. Intern, 14:7-24 (1976).
Villines et al., The Arbiter 6-Halts Trial (Arterial Biology for the Investigation of the Treatment Effects of Reducing Cholesterol 6 HDL and LDL Treatment Strategies in Atherosclerosis): Final Results and the Impact of Medication Adherence, Dose, and Treatment Duration, J. Am. Coll. Cardiol. 55(24)1-6(2010).
Waters et al., Effects of High-Dose Atorvastatin on Cerebrovascular Events in Patients with Stable Coronary Disease in the TNT (Treating to New Targets) Study, J. Am Coll Card, 48(9)1793-1799 (2006).
Weeks et al., A Comparison of the Molecular Structures of Six Corticosteroids, J. Am. Chem. Soc. 95(9):2865-2868 (1973).
Weisweiler and Schwandt, Colestipol plus fenofibrate versus synvinolin in familial hypercholesterolaemia, Lancet 1212-1213 (Nov. 22, 1986).
Welch and Eswarakrishnan, Fluorine in Bioorganic Chemistry, John Wiley & Sons, NY, pp. 1-261 (1991).
Welch, Advances in the Preparation of Biologically Active Organofluorine Compounds, Tetrahedron 43(14):3123-3197 (1987).
Wermuth, Chemical modifications of medications with a view to the improvement of their action, Agressologie 7(3):213-219 (1966).
Wilhelm et al., 6-Fluoro-Vitamin $D_3$: A New Antagonist of the Biological Actions of Vitamin $D_3$ and its Metabolites which Interacts with the Intestinal Receptor for 1 $\alpha$,25$(OH)_2$-Vitamin $D_3$, Arch. Biochem. Biophys. 233(1):127-132 (1984).
Williams, Drug Metabolism, in Principles of Medicinal Chemistry, Third Ed., Ch. 5, pp. 79-117 (Foye, ed.), Lea & Febinger, Philadelphia (1989).
Wirebaugh et al., A Retrospective Review of the Use of Lipid-Lowering Agents in Combination, Specifically, Gemfibrozil and Lovastatin, Pharmacotherapy 12(6):445-450 (1992).
Wolff et al., Substrate Specificity of Human Liver Cytochrome P-450 Debrisoquine 4-Hydroxylase Probed Using Immunochemical Inhibition and Chemical Modeling, Cancer Res. 45:2116-2122 (1985).
Wood et al., The Effect of Cimetidine on Anesthetic Metabolism and Toxicity, (1986) Anesth. Analg. 65(5):481488.
Woodrow, Essentials Of Pharmacology For Health Occupations, 4th Ed., Delmar, Thomson Learning, Ch. 7, pp. 87-139—"right amount" (2002).
Wu et al., A Novel One-Step Diastereo—and Enantioselective Formation of Trans-Azetidinones and its Application to the Total Synthesis of Cholesterol Absorption Inhibitors, J. Org. Chem. 64(10):3714-3718 (1999).
Yumibe et al., Identification of human liver cytochrome P450 enzymes that metabolize the nonsedating antihistamine loratadine. Formation of descarboethoxyoratadine by CYP3A4 and CYP2D6, Biochem. Pharm. 51:165-172 (1996).
Zia-Amirhosseini, Bioactivation by Glucuronide-Conjugate Formation, Adv. Pharma, 27:385-397 (1994).
Complaint against Glenmark Pharmaceuticals, Inc. USA, Glenmark Pharmaceuticals Ltd., filed by Schering Corporation, MSP Singapore Company LLC. (Attachments: # 1 Statement 7.1 disclosure# 2 Civil Cover Sheet # 3 Summons Glenmark, USA# 4 Summons Glenmark Ltd.)(mn, ) (Entered: Mar. 23, 2007), U.S. District Court for the District of New Jersey (Civil Action No. 07-cv-1334 (JLL/ES)).
Answer to Complaint, Counterclaim against all plaintiffs by Glenmark Pharmaceuticals, Inc. USA. (Attachments: # 1 Corporate Disclosure Statement)(Walsh, Liza) (Entered: May 23, 2007), U.S. District Court for the District of New Jersey (Civil Action No. 07-cv-1334 (JLL/ES)).
*Corrected* Answer to Complaint, Counterclaim against Schering Corporation, MSP Singapore Company LLC by Glenmark Pharmaceuticals Ltd..(Walsh, Liza) (Entered: Jun. 7, 2007), U.S. District Court for the District of New Jersey (Civil Action No. 07-cv-1334 (JLL/ES)).
*Corrected* Answer to Complaint, Counterclaim against Schering Corporation, MSP Singapore Company LLC by Glenmark Pharmaceuticals, Inc. USA Ltd..(Walsh, Liza) (Entered: Jun. 7, 2007), U.S. District Court for the District of New Jersey (Civil Action No. 07-cv-1334 (JLL/ES)).
Answer to Counterclaim of *Glenmark Pharmaceuticals, Ltd.* by Schering Corporation, MSP Singapore Company LLC. (Attachments: # 1 Certificate of Service)(Halper, Jason) (Entered: Jul. 3, 2007), U.S. District Court for the District of New Jersey (Civil Action No. 07-cv-1334 (JLL/ES)).
Answer to Counterclaim of Glenmark Pharmaceuticals, Inc. USA. by Schering Corporation, MSP Singapore Company LLC. (Attachments: # 1 Certificate of Service)(Halper, Jason) (Entered: Jul. 3, 2007), U.S. District Court for the District of New Jersey (Civil Action No. 07-cv-1334 (JLL/ES)).
Letter from Liza M. Walsh to the Honorable Jose L. Linares. (Attachments: # 1 Brief in Support of Proposed Claim Interpretations# 2 Declaration of Agnes Antonian # 3 Text of Proposed Order # 4 Certificate of Service)(Walsh, Liza) (Entered: Jan. 14, 2008), U.S. District Court for the District of New Jersey (Civil Action No. 07-cv-1334 (JLL/ES)).

Letter from Plaintiffs Enclosing Plaintiffs' Opening Claim Construction Brief. (Attachments: # 1 Brief# 2 Proposed Order# 'Certification of Service# 4 Krause Declaration, Ex. A# 5 Krause Declaration, Ex. B# 6 Krause Declaration, Ex. C Part 1# 7 Krause Declaration, Ex. C Part 2# 8 Krause Declaration, Ex. C Part 3# 9 Krause Declaration, Ex. D Part 1# 10 Krause Declaration, Ex. D Part 2# 11 Krause Declaration, Ex. D Part 3# 12 Krause Declaration, Ex. D Part 4# 13 Krause Declaration, Ex. E Part 1# 14 Krause Declaration, Ex. E Part 2# 15 Krause Declaration, Ex. E Part 3# 16 Krause Declaration, Ex. E Part 4# 17 Krause Declaration, Ex. E Part 5# 18 Krause Declaration, Ex. E Part 6# 19 Krause Declaration, Exs. F-G# 20 Krause Declaration, Exs. H-O# 21 Krause Declaration, Exs. P-Q)(Halper, Jason) (Entered: Jan. 14, 2008), U.S. District Court for the District of New Jersey (Civil Action No. 07-cv-1334 (JLL/ES)).

Brief *In Response To Plaintiffs' Proposed Claim Interpretations* filed by Glenmark Pharmaceuticals Ltd., Glenmark Pharmaceuticals, Inc. USA. (Attachments: # 1 Certification of Service)(Walsh, Liza) (Entered: Feb. 12, 2008), U.S. District Court for the District of New Jersey (Civil Action No. 07-cv-1334 (JLL/ES)).

Brief *in Opposition to Defendants' Opening Markman Brief* filed by Schering Corporation, MSP Singapore Company LLC. (Attachments: # 1 Supplemental Krause Declaration, # 2 Supp. Krause Declaration, Exs. R-V, # 3 Supp. Krause Declaration, Exs. W-Y, # 4 Certification of Service)(Halper, Jason) (Entered: Feb. 12, 2008), U.S. District Court for the District of New Jersey (Civil Action No. 07-cv-1334 (JLL/ES)).

*First Amended* Answer to Complaint by Glenmark Pharmaceuticals, Inc.USA.(Walsh, Liza) (Entered: Mar. 10, 2008), U.S. District Court for the District of New Jersey (Civil Action No. 07-cv-1334 (JLL/ES)).

*First Amended* Answer to Complaint by Glenmark Pharmaceuticals Ltd. (Walsh, Liza) (Entered: Mar. 10, 2008), U.S. District Court for the District of New Jersey (Civil Action No. 07-cv-1334 (JLL/ES).

Answer to Counterclaim *Amended Counterclaim of Glenmark Pharmaceuticals, Inc.* USA by Schering Corporation, MSP Singapore Company LLC. (Attachments: # 1 Certification of Service)(Halper, Jason) (Entered: Apr. 9, 2008), U.S. District Court for the District of New Jersey (Civil Action No. 07-cv-1334 (JLL/ES)).

Answer to *Counterclaim Amended Counterclaim of Glenmark Pharmaceuticals Ltd.* by Schering Corporation, MSP Singapore Company LLC. (Attachments: # 1 Certification of Service)(Halper, Jason) (Entered: Apr. 9, 2008), U.S. District Court for the District of New Jersey (Civil Action No. 07-cv-1334 (JLL/ES)).

Letter from Plaintiffs regarding July 29 Markman Hearing re Letter from Plaintiffs Enclosing Plaintiffs' Opening Claim Construction Brief, (Halper, Jason) (Entered: Aug. 1, 2008), U.S. District Court for the District of New Jersey (Civil Action No. 07-cv-1334 (JLL/ES)).

Letter from Defendants In Response to Plaintiffs' Aug. 1 Suppl Briefing On Claim Construction. (Ruiz, Hector) (Entered: Aug. 7, 2008), U.S. District Court for the District of New Jersey (Civil Action No. 07-cv-1334 (JLL/ES)).

Letter from Plaintiffs in Reply to Glenmark's Aug. 6, 2008 Letter re Letter from Plaintiffs Enclosing Plaintiffs' Opening Claim Construction Brief, (Halper, Jason) (Entered: Aug. 8, 2008), U.S. District Court for the District of New Jersey (Civil Action No. 07-cv-1334 (JLL/ES)).

Letter from Defendants in Response to Plaintiffs' Aug. 8, 2008 Letter On Claim Construction Issues. (Ruiz, Hector) (Entered: Aug. 12, 2008), U.S. District Court for the District of New Jersey (Civil Action No. 07-cv-1334 (JLL/ES)).

Opinion. Signed by Judge Jose L. Linares on Sep. 15, 2008. (DD,) (Entered: Sep. 16, 2008), U.S. District Court for the District of New Jersey (Civil Action No. 07-cv-1334 (JLL/ES)).

Order granting Plaintiff's appl. For claims construction.. Signed by Judge Jose L. Linares on Sep. 15, 2008. (DD, ) (Entered: Sep. 16, 2008), U.S. District Court for the District of New Jersey (Civil Action No. 07-cv-1334 (JLL/ES)).

Motion for Partial Summary Judgment of Invalidity of Claims 10-13 (Improper Reissue) by Glenmark Pharmaceuticals, Inc. USA. (Attachments: # 1 Statement of Undisputed Material Facts, # 2 Confidential Memorandum of Law [Redacted], # 3 Confidential Declaration of Robert L. Jacobson [Redacted], # 4 Confidential Exhibits A-E [Redacted], # 5 Confidential Exhibits F-K [Redacted], # 6 Proposed Order, # 7 Certificate of Service)(Walsh, Liza) Modified on Apr. 12, 2010 (DD,). (Entered: Jul. 1, 2009), U.S. District Court for the District of New Jersey (Civil Action No. 07-cv-1334 (JLL/ES)).

Motion for Summary Judgment of Invalidity of Claims 1-5 and 7-13 (Double Patenting) by Glenmark Pharmaceuticals, Inc. USA, Glenmark Pharmaceuticals Ltd. (Attachments: #1 Statement of Material Facts Not in Dispute, # 2 Memorandum of Law In Support of Summary Judgment, # 3 Declaration of George Hykal, # 4 Exhibits A through B to George Hykal Declaration, # 5 Exhibits C through E to George Hykal Declaration, # 6 Exhibits F through H to George Hykal Declaration, # 7 Proposed Order, # 8 Certificate of Service)(Walsh, Liza) Modified on Apr. 12, 2010 (DD, ). (Entered: Jul. 8, 2009), U.S. District Court for the District of New Jersey (Civil Action No. 07-cv-1334 (JLL/ES)).

Brief in Opposition re Motion for Partial Summary Judgment of Invalidity of Claims 10-13 (Improper Reissue) filed by Schering Corporation, MSP Singapore Company LLC. (Attachments: # 1 Rule 56.1 Responsive Statement of Material Facts, # 2 Suh Declaration, # 3 Suh Declaration Exhibits (Redacted), # 4 Proposed Order, # 5 Certification of Service)(Halper, Jason) (Entered: Jul. 22, 2009), U.S. District Court for the District of New Jersey (Civil Action No. 07-cv-1334 (JLL/ES)).

Brief in Opposition re Motion for Summary Judgment of Invalidity of Claims 1-5 and 7-13 (Double Patenting) filed by Schering Corporation, MSP Singapore Company LLC. (Attachments: # 1 Local Rule 56.1 Statement of Facts, # 2 Proposed Order, # 3 Certification of Service)(Halper, Jason) (Entered: Aug. 5, 2009), U.S. District Court for the District of New Jersey (Civil Action No. 07-cv-1334 (JLL/ES)).

Certification in Opposition re Motion for Summary Judgment of Invalidity of Claims 1-5 and 7-13 (Double Patenting) Declaration of James Suh filed by Schering Corporation, MSP Singapore Company LLC. (Attachments: # 1 Exibits 1-4, # 2 Exhibits 5-16, # 3 Exhibits 17, # 4 Exhibit 18 (Part 1), # 5 Exhibit 18 (Part 2) # 6 Exhibits 19-21, # 7 Exhibit 22, # 8 Exhibits 23-25, # 9 Exhibit 26 (Part 1), # 10 Exhibit 26 (Part 2), # 11 Exhibit 26 (Part 3), #12 Exhibit 26 (Part 4), # 13 Exhibits 27-29, # 14 Exhibits 30-32, # 15 Exhibit 33, # 16 Exhibit 34, # 17 Exhibits 35-40, # 18 Exhibits 41-46, # 19 Exhibit 47 (Part 1), # 20 Exhibit 47 (Part 2), # 21 Exhibits 48-52, # 22 Exhibit 53 (Part 1), # 23 Exhibit 53 (Part 2), #24 Exhibit 53 (Part 3), # 25 Exhibits 54-60, # 26 Exhibit 61 (Part 1), # 27 Exhibit 61 (Part 2), # 28 Exhibits 62-63, # 29 Exhibit 64, # 30 Exhibits 65-69)(Halper, Jason) (Entered: Aug. 5, 2009), U.S. District Court for the District of New Jersey (Civil Action No. 07-cv-1334 (JLL/ES)).

Reply Brief to Opposition to Motion re Motion for Partial Summary Judgment of Invalidity of Claims 10-13 (Improper Reissue) filed by Glenmark Pharmaceuticals Ltd.. (Attachments: # 1 Resp. To Suppl. Stmn. of Disputed Facts (Redacted), # 2 Decl. of Jay Lessler, # 3 Exhibit A pp. 1-29, # 4 Exhibit A pp. 30-59, # 3 : Exhibit A pp. 60-89, # 6 Exhibit A pp. 90-112, # 7 Exhibit B, # D, Exhibit C)(Walsh, Liza) (Entered: Aug. 10, 2009), U.S. District Court for the District of New Jersey (Civil Action No. 07-cv-1334 (JLL/ES)).

Reply Brief to Opposition to Motion re Motion for Partial Summary Judgment of Invalidity of Claims 10-13 (Improper Reissue) Amended Reply Brief filed by Glenmark Pharmaceuticals Ltd.. (Attachments: # 1 Revised Declaration of Jay P. Lessler, # 2 Lttr. to Judge Linares Encl. Amended Reply and Revised Decl.)(Walsh, Liza) (Entered: Aug. 14, 2009), U.S. District Court for the District of New Jersey (Civil Action No. 07-cv-1334 (JLL/ES)).

Reply Brief to Opposition to Motion re Motion for Summary Judgment of Invalidity of Claims 1-5 and 7-13 (Double Patenting) filed by Glenmark Pharmaceuticals Ltd.. (Attachments: # 1 Resp. to Pltffs.' Stmn. of Disputed Facts (Redacted))(Walsh, Liza) (Entered: Aug. 21, 2009), U.S. District Court for the District of New Jersey (Civil Action No. 07-cv-1334 (JLL/ES)).

Pretrial Memorandum by MSP Singapore Company LLC, Schering Corporation. (Attachments: # 1 Certificate of Service)(Halper, Jason) (Entered: Dec. 14, 2009), U.S. District Court for the District of New Jersey (Civil Action No. 07-cv-1334 (JLL/ES)).

Notice by Glenmark Pharmaceuticals Ltd., Glenmark Pharmaceuticals, Inc.USA re MOTION for Partial Summary Judgment of Invalidity of Claims 10-13 (Improper Reissue) of Supplemental Authority in Support of Glenmark's Motion for Partial Summary Judgment of Invalidity of Claims 10-13 (Improper Reissue) (Attachments: # 1 Appendix A)(Lessler, Jay) (Entered: Jan. 12, 2010), U.S. District Court for the District of New Jersey (Civil Action No. 07-cv-1334 (JLL/ES)).
Letter from Plaintiffs in Response to Defendants' Notice of Supplemental Authority re Notice by Glenmark Pharmaceuticals Ltd., Glenmark Pharmaceuticals, Inc.USA re Motion for Partial Summary Judgment of Invalidity of Claims 10-13 (Improper Reissue) of Supplemental Authority in Support of Glenmark's Motion for Partial Summary Judgment of Invalidity of Claims 10-13 (Improper Reissue). (Halper, Jason) (Entered: Jan. 14, 2010), U.S. District Court for the District of New Jersey (Civil Action No. 07-cv-1334 (JLL/ES)).
Order withdrawing Motion for Partial Summary Judgment of Invalidity of Claims 10-13 (Improper Reissue); withdrawing Motion for Summary Judgment of Invalidity of Claims 1-5 and 7-13 (Double Patenting); Signed by Judge Jose L. Linares on Mar. 30, 2010. (DD, ) (Entered: Mar. 31, 2010), U.S. District Court for the District of New Jersey (Civil Action No. 07-cv-1334 (JLL/ES)).
Order Reinstating re Motion for Partial Summary Judgment of Invalidity of Claims 10-13 (Improper Reissue) filed by Glenmark Pharmaceuticals, Inc. USA, Motion for Summary Judgment of Invalidity of Claims 1-5 and 7-13 (Double Patenting) filed by Glenmark Pharmaceuticals Ltd., Glenmark Pharmaceuticals, Inc. USA. Signed by Judge Jose L. Linares on Apr. 9, 2010. (DD, ) (Entered: Apr. 12, 2010), U.S. District Court for the District of New Jersey (Civil Action No. 07-cv-1334 (JLL/ES)).
Opinion. Signed by Judge Jose L. Linares on Apr. 19, 2010. (jd, ) (Entered: Apr. 19, 2010), U.S. District Court for the District of New Jersey (Civil Action No. 07-cv-1334 (JLL/ES)).
Order granting Motion for Partial Summary Judgment of Invalidity of Claims 10-13 (Improper Reissue); denying Motion for Summary Judgment of Invalidity of Claims 1-5 and 7-13 (Double Patenting). Signed by Judge Jose L. Linares on Apr. 19, 2010. (jd, ) (Entered: Apr. 19, 2010), U.S. District Court for the District of New Jersey (Civil Action No. 07-cv-1334 (JLL/ES)).
Motion for Reconsideration of the Court's Order Granting Defendants' Motion for Summary Judgment of Invalidity of Claims 10 through 13 by MSP Singapore Company LLC, Schering Corporation. (Attachments: # 1 Brief in Support of Plaintiffs' Motion for Reconsideration of the Court's Order Granting Defendants' Motion for Summary Judgment of Invalidity of Claims 10 through 13, # 2 Text of Proposed Order, # 3 Certificate of Service)(Halper, Jason) (Entered: Apr. 30, 2010), U.S. District Court for the District of New Jersey (Civil Action No. 07-cv-1334 (JLL/ES)).
Brief in Opposition re Motion for Reconsideration of the Court's Order Granting Defendants' Motion for Summary Judgment of Invalidity of Claims 10 through 13 filed by Glenmark Pharmaceuticals Ltd., Glenmark Pharmaceuticals, Inc. USA. (Attachments: # 1 Proposed Order, # 2 Certification of Service)(Walsh, Liza) (Entered: May 4, 2010), U.S. District Court for the District of New Jersey (Civil Action No. 07-cv-1334 (JLL/ES)).
Letter from Glenmark Pharmaceuticals Inc., USA and Glenmark Pharmaceuticals Ltd. regarding Plaintiffs' Motion for Reconsideration of the Court's Order Granting Defendants' Motion for Summary Judgment of Invalidity of Claims 10 through 13.. (Walsh, Liza) (Entered: May 4, 2010), U.S. District Court for the District of New Jersey (Civil Action No. 07-cv-1334 (JLL/ES)).
Order Vacating re Order granting on Motion for Partial Summary Judgment of Invalidity of Claims 10-13 (Improper Reissue), Order on denying Motion for Summary Judgment of Invalidity of Claims 1-5 and 7-13 (Double Patenting), Apr. 19, 2010 Opinion. Signed by Judge Jose L. Linares on May 10, 2010. (DD, ) (Entered: May 10, 2010), U.S. District Court for the District of New Jersey (Civil Action No. 07-cv-1334 (JLL/ES)).
Consent Judgment. Signed by Judge Jose L. Linares on May 10, 2010. (DD) (Entered: May 10, 2010), U.S. District Court for the District of New Jersey (Civil Action No. 07-cv-1334 (JLL/ES)).
Complaint against Mylan Inc., Mylan Pharmaceuticals Inc., filed by Schering Corporation, MSP Singapore Company LLC. (Attachments: #1 Summons1, # 2 Summons2, # 3 Civil Cover Sheet)(Id) (Entered: Dec. 22, 2009), U.S. District Court for the District of New Jersey (Civil Action No. 09-cv-06383 (JLL/ES)).
Motion to Dismiss for Failure to State a Claim Upon Which Relief May Be Granted and/or for Lack of Subject Matter Jurisdiction by Mylan Inc. (Attachments: #1 Brief in support of Mylan, Inc.'s Motion to Dismiss, # 2 Declaration of Andrew Kozusko in support of Mylan, Inc.'s Motion to Dismiss, # 3 Text of Proposed Order, # 4 Certificate of Service)(Calmann, Arnold) (Entered: Feb. 12, 2010), U.S. District Court for the District of New Jersey (Civil Action No. 09-cv-06383 (JLL/ES)).
Answer to Complaint, Separate Defenses, Counterclaim against MSP Singapore Company LLC, Schering Corporation by Mylan Pharmaceuticals Inc.. (Attachments: # 1 Certificate of Service)(Calmann, Arnold) (Entered: Feb. 12, 2010), U.S. District Court for ihe District of New Jersey (Civil Action No. 09-cv-06383 (JLL/ES)).
Amended Answer to Complaint, Separate Defenses, Amended Counterclaim and Jury Demand against MSP Singapore Company LLC, Schering Corporation by Mylan Pharmaceuticals Inc.. (Attachments: # 1 Certificate of Service)(Calmann, Arnold) (Entered: Mar. 2, 2010), U.S. District Court for the District of New Jersey (Civil Action No. 09-cv-06383 (JLL/ES)).
Stipulation of Dismissal as to Defendant Mylan Inc. by MSP Singapore Company LLC, Schering Corporation. (Attachments: # 1 Letter)(Halper, Jason) (Entered: Mar. 11, 2010), U.S. District Court for the District of New Jersey (Civil Action No. 09-cv-06383 (JLL/ES)).
Stipulation and Order terminating Deft. Mylan Inc., etc., Signed by Judge Jose L. Linares on Mar. 16, 2010. (dc, ) (Entered: Mar. 18, 2010), U.S. District Court for the District of New Jersey (Civil Action No. 09-cv-06383 (JLL/ES)).
Answer to Counterclaim by MSP Singapore Company LLC, Schering Corporation.(Halper, Jason) (Entered: Apr. 7, 2010), U.S. District Court for the District of New Jersey (Civil Action No. 09-cv-06383 (JLL/ES)).
Complaint against Teva Pharmaceutical Industries Ltd., Teva Pharmaceuticals USA, Inc., filed by Schering Corporation, MSP Singapore Company LLC. (Attachments: # 1 Civil Cover Sheet)(dr) (Entered: Mar. 4, 2010), U.S. District Court for the District of New Jersey (Civil Action No. 2:10-cv-01058 (JLL/ES)).
Stipulation of Dismissal as to Defendant Teva Pharmaceutical Industries Ltd. by MSP Singapore Company LLC, Schering Corporation. (Halper, Jason) (Entered: Mar. 30, 2010), U.S. District Court for the District of New Jersey (Civil Action No. 2:10-cv-01058 (JLL/ES)).
Stipulation and Order dismissing action as to deft. Teva Pharmaceutical Industries, Ltd. Signed by Judge Jose L. Linares on Mar. 31, 2010. (nr) (Entered: Apr. 5, 2010), U.S. District Court for the District of New Jersey (Civil Action No. 2:10-cv-01058 (JLL/ES)).
Answer to Complaint by Teva Pharmaceuticals USA, Inc. (Patunas, Michael) (Entered: Apr. 12, 2010), U.S. District Court for the District of New Jersey (Civil Action No. 2:10-cv-01058 (JLL/ES)).
Corrected Answer to Complaint by Teva Pharmaceuticals USA, Inc. (Patunas, Michael) (Entered: Apr. 12, 2010), U.S. District Court for the District of New Jersey (Civil Action No. 2:10-cv-01058 (JLL/ES)).
Amended Answer to Complaint by Teva Pharmaceuticals USA, Inc. (Patunas, Michael) (Entered: May 3, 2010), U.S. District Court for the District of New Jersey (Civil Action No. 2:10-cv-01058 (JLL/ES)).
Complaint against Mylan Pharmaceuticals, Inc. and Mylan Inc. filed by Schering Corporation and MSP Singapore Company LLC., (filed Jun. 16, 2010), U.S. District Court for the District of New Jersey (Civil Action No. 2:10-cv-03085-JLL-CCC).
Answer to Complaint with Jury Demand , Separate Defenses, Counterclaim against MSP Singapore Company LLC, Schering Corporation by Mylan Pharmaceuticals Inc.. (Attachments: # 1 Certificate of Service)(Calmann, Arnold) (Entered: Jul. 28, 2010), U.S. District Court for the District of New Jersey (Civil Action No. 2:10-cv-03085-JLL-CCC).

Complaint against Impax Laboratories, Inc., filed by Schering Corporation, MSP Singapore Company, LLC. (Attachments: # 1 EXH A, # 2 EXH B, # 3 EXH C, # 4 Civil Cover Sheet, # 5 Summons)(dr, ) (Entered: Aug. 24, 2010), U.S. District Court for the District of New Jersey (Civil Action No. 2:10-cv-04270-JLL-CCC).
Complaint against Teva Pharmaceutical Industries Ltd., Teva Pharmaceuticals USA, Inc., filed by Schering Corporation, MSP Singapore Company LLC. (Attachments: # 1 Exhibit A to Complaint, # 2 Exhibit B to Complaint, # 3 Exhibit C to Complaint, # 4 Summonsl, # 5 Summons2, # 6 Civil Cover Sheet)(Id, ) (Entered: Sep. 2, 2010), U.S. District Court for the District of New Jersey (Civil Action No. 2:10-cv-04473-JLL-CCC).
Complaint against Mylan Inc., Mylan Pharmaceuticals Inc., filed by Schering Corporation, MSP Singapore Company LLC. (Attachments: # 1 Exhibit A, # 2 Exhibit B, # 3 Civil Cover Sheet, # 4 Cover letter)(kd) (Entered: Dec. 18, 2009), U.S. District Court for the Northern District of West Virginia (Civil Action No. 1:09-cv-00167-IMK).
Notice of Voluntary Dismissal by MSP Singapore Company LLC, Schering Corporation (Attachments: # 1, Attachment Exhibit 1)(Simmerman, Frank) (Entered: Apr. 15, 2010), U.S. District Court for the Northern District of West Virginia (Civil Action No. 1:09-cv-00167-IMK).
Complaint against Mylan Pharmaceuticals, Inc. and Mylan Inc. filed by Schering Corporation and MSP Singapore Company LLC., (filed Jun. 29, 2010), U.S. District Court for the Northern District of West Virginia (Civil Action No. 1:10-cv-99-IMK).
Notice of Voluntary Dismissal by MSP Singapore Company, LLC, Schering Corporation (Attachments: # 1 Exhibit, Exhibit One)(Simmerman, Frank) (Entered: Aug. 19, 2010), U.S. District Court for the Northern District of West Virginia (Civil Action No. 1:10-cv-99-IMK).
Complaint; summons issued against Impax Laboratories, Inc., Filed by Schering Corporation, MSP Singapore Company LLC. (slh) (Filed on Aug. 20, 2010) (Entered: Aug. 23, 2010), U.S. District Court for the Northern District of California (Civil Action No. 3:10-cv-03719-JSW).
Deposition Transcript of Sundeep Dugar, Ph.D., dated May 2, 2008, U.S. District Court for the District of New Jersey (Civil Action No. 07-cv-1334 (JLL/ES)).
Deposition Transcript of Nathan Yumibe, dated May 9, 2008, U.S. District Court for the District of New Jersey (Civil Action No. 07-cv-1334 (JLL/ES)).
Deposition Transcript of Dr. Wayne Vaccaro, dated Jun. 11, 2008, U.S. District Court for the District of New Jersey (Civil Action No. 07-cv-1334 (JLL/ES)).
Hearing Transcript before the Honorable Jose L. Linares (Markman Hearing), dated Jul. 29, 2008, U.S. District Court for the District of New Jersey (Civil Action No. 07-cv-1334 (JLL/ES)).
Deposition Transcript of Kevin Alton, dated Sep. 9, 2008, U.S. District Court for the District of New Jersey (Civil Action no. 07-cv-1334 {JLL/ES)).
Deposition Transcript of Margaret Van Heek, dated Sep. 11, 2008, U.S. District Court for the District of New Jersey (Civil Action No. 07-cv-1334 (JLL/ES)).
Deposition Transcript of Duane Burnett, dated Sep. 25, 2008, U.S. District Court for the District of New Jersey (Civil Action No. 07-cv-1334 (JLL/ES)).
Plaintiffs' Responses to Glenmark's Second Set of Interrogatories (Nos. 17-21), dated Sep. 25, 2008, U.S, District Court for the District of New Jersey (Civil Action No. 07-cv-1334 (JLL/ES)).
Deposition 'Transcript of Harry Davis, dated Oct. 14, 2008, U.S. District Court for the District of New Jersey (Civil Action No. 07-cv-1334 (JLL/ES)).
Deposition Transcript of Adriano Afonso, dated Oct. 21, 2008, U.S. District Court for the District of New Jersey (Civil Action No. 07-cv-1334 (JLL/ES)).
Deposition Transcript of James Nelson, dated Oct. 29, 2008, U.S. District Court for the District of New Jersey (Civil Action No. 07-cv-1334 (JLL/ES)).
Deposition Transcript of James Nelson, dated Oct. 30, 2008, U.S. District Court for the District of New Jersey (Civil Action No. 07-cv-1334 (JLL/ES)).
Deposition Transcript of Cecil B. Pickett, dated Nov. 14, 2008. U.S. District Court for the District of New Jersey (Civil Action No. 07-cv-1334 (JLL/ES)).
Deposition Transcript of Stuart B. Rosenblum, dated Dec. 4, 2008, U.S. District Court for the District of New Jersey (Civil Action No. 07-cv-1334 (JLL/ES)).
Deposition Transcript of Stuart B. Rosenblum, dated Dec. 5, 2008, U.S. District Court for the District of New Jersey (Civil Action No. 07-cv-1334 (JLL/ES)).
Deposition Transcript of John Clader, Ph.D, dated Dec. 11, 2008, U.S. District Court for the District of New Jersey (Civil Action No. 07-cv-1334 (JLL/ES)).
Deposition Transcript of Anita Magatti, dated Jan. 7, 2009, U.S. District Court for the District of New Jersey (Civil Action No. 07-cv-1334 (JLL/ES)).
Deposition Transcript of Dorothy Auth, dated Jan. 9, 2009, U.S. District Court for the District of New Jersey (Civil Action No. 07-cv-1334 (JLL/ES)).
Deposition Transcript of Stuart Rosenbaum, dated Feb. 10, 2009, U.S. District Court for the District of New Jersey (Civil Action No. 07-cv-1334 (JLL/ES)).
Expert Report of Clayton Heathcock, Ph.D., dated Feb. 25, 2009, U.S, District Court for the District of New Jersey (Civil Action No. 07-cv-1334 (JLL/ES)).
Expert Report of Dr. Ronald Hines, dated Feb. 27, 2009, U.S. District Court for the District of New Jersey (Civil Action No. 07-cv-1334 (JLL/ES)).
Expert Report of Richard Bruce van Breernen, Ph.D., dated Mar. 2, 2009, U.S District Court for the District of New Jersey (Civil Action No. 07-cv-1337 (JLL/ES)).
Expert Report of Paul Ortiz de Montellano, Ph.D., dated Mar. 2, 2009, U.S. District Court for the District of New Jersey (Civil Action No. 07-cv-1334 (JLL/ES)).
Glenmark Pharmaceuticals Inc., USA and Glenmark Pharmaceuticals Ltd.'s Amended Responses to Plaintiffs' Interrogatories (Nos. 1-17), dated Mar. 6, 2009, U.S. District Court for the District of New Jersey (Civil Action No. 07-cv-1334 (JLL/ES)).
Expert Report of F. Peter Guengerich, dated Apr. 16, 2009, U.S. District Court for the District of New Jersey (Civil Action No. 07-cv-1334 (JLL/ES)).
Expert Report of Christopher A. Vellturo. Ph.D., dated Apr. 17, 2009, U.S. District Court for the District of New Jersey (Civil Action No. 07-cv-1334 (JLL/ES)).
Expert Report of Stephen G. Kunin, Esq. , dated Apr. 17, 2009, U.S. District Court for the District of New Jersey (Civil Action No. 07-cv-1334 (JLL/Es)).
Expert Report of Ronald G. Brisbois, Ph.D., dated Apr. 20, 2009, U.S. District Court for the District of New Jersey (Civil Action No. 07-cv-1334 (JLL/ES)).
Expert Report of W. Virgil Brown, M.D., dated Apr. 20, 2009, U.S. District Court for the District of New Jersey (Civil Action No. 07-cv-1334 (JLL/ES)).
Expert Report of William R. Roush, Ph.D., dated Apr. 20, 2009, U.S. District Court for the District of New Jersey (Civil Action No. 07-cv-1334 (JLL/ES)).
Rebuttal Expert Report of Clayton Heathcock, dated May 8, 2009, U.S. District Court for the District of New Jersey (Civil Action No. 07-cv-1334 (JLL/ES)).
Rebuttal Expert Report of Ronald N. Hines, dated May 8, 2009, U.S. District Court for the District of New Jersey (Civil Action No. 07-cv-1334 (JLL/ES)).
Rebuttal Expert Report of Paul Ortiz de Montellano, dated May 8, 2009, U.S. District Court for the District of New Jersey (Civil Action No. 07-cv-1334 (JLL/ES)).
Rebuttal Expert Report of Jesse David, dated May 8, 2009. U.S. District Court for the District of New Jersey (Civil Action No. 07-cv-1334 (JLL/ES)).
Glenmark Pharmaceuticals Inc., USA and Glenmark Pharmaceuticals Ltd.'s Supplemental Response To Plaintiffs' Interrogatory No. 1, dated May 11, 2009, U.S. District Court for the District of New Jersey (Civil Action No. 07-cv-1334 (JLL/ES)).

Supplemental Expert Report of Ronald G. Brisbois, Ph.D., dated May 22, 2009, U.S. District Court for the District of New Jersey (Civil Action No. 07-cv-1334 (JLL/ES)).
Statement of Material Fact in Support re Motion for Partial Summary Judgment of Invalidity of Claims 10-13 (Improper Reissue) Resp. to Plaintiffs' Stmnt. of Disputed Material Facts (Confidential) filed by Glenmark Pharmaceuticals Ltd.. (Walsh, Liza) (Entered: Aug. 10, 2009), U.S. District Court for the District of New Jersey (Civil Action No. 07- cv-1334 (JLL/ES)).
Statement of Material Fact in Support re Motion for Summary Judgment of Invalidity of Claims 1-5 and 7-13 (Double Patenting) Resp. to Plaintiffs' Stmnt. of Disputed Material Facts (Confidential) filed by Glenmark Pharmaceuticals Ltd.. (Walsh, Liza) (Entered: Aug. 21, 2009), U.S. District Court for the District of New Jersey (Civil Action No. 07-cv-1334 (JLL/ES)).
Glenmark Pharmaceuticals Inc., USA and Glenmark Pharmaceuticals Ltd.'s Supplemental Response To Plaintiffs' Interrogatory No. 4, dated Nov. 6, 2009, U.S. District Court for the District of New Jersey (Civil Action No. 07-cv-1334 (JLL/ES)).
Trial Brief Defendants' (Filed Under Seal) by Glenmark Pharmaceuticals Ltd., Glenmark Pharmaceuticals, Inc.USA. (Attachments: # 1 Certificate of Service)(Lessler, Jay) (Entered: Dec. 14, 2009), U.S. District Court for the District of New Jersey (Civil Action No. 07-cv-1334 (JLL/ES)).
Final Pretrial Order, U.S. District Court for the District of New Jersey (redacted for Glenmark confidential information and personal information of witnesses), signed Mar. 11, 2010 (Civil Action No. 07-cv-1334 (JLL/ES)).
Joint Claim Construction and PreHearing Statement, dated Jul. 23, 2010, U.S. District Court for the District of New Jersey (Civil Action No. 09-0v-06383 (JLL/ES)).
Defendant Mylan Pharmaceuticals Inc.'s Objections and Responses to Plaintiffs' First Set of Interrogatories (Nos. 1-3), dated Jul. 30, 2010, U.S. District Court for the District of New Jersey (Civil Action No. 09-cv-06383 (JLL/ES)).
Plaintiffs' Response and Objections to Defendant Mylan Pharmaceuticals Inc.'s First Set of Interrogatories to Plaintiffs (Nos. 1-11), dated Jul. 30, 2010, U.S. District Court for the District of new Jersey (Civil Action No. 09-cv-06383 (JLL/ES)).
Transcript of Proceedings held on Aug. 12, 2010, before Judge Esther Salas, U.S. District Court for the District of New Jersey (Civil Action No. 09-cv-06383 (JLL/ES)).
Transcript of Proceedings held on Sep. 8, 2010, before Judge Esther Salas, U.S. District Court for the District of New Jersey (Civil Action No. 09-cv-06383 (JLL/ES)).
Defendant Mylan Pharmaceuticals Inc.'s Amended Invalidity and Non-Infringement Contentions Pursuant to Local Patent Rules 3.3 and 3.6 (redacted for Mylan confidential information), dated Sep. 9, 2010, U.S. District Court for the District of New Jersey (Civil Action No. 09-cv-06383 (JLL/ES)).
Letter from Plaintiffs Schering Corporation and MSP Singapore Company LLC to Judge Esther Salas seeking Modification of Proposed Claim Constructions Provided inJoint Claim Construction and Prehearing Statement (Proposed Order attached), dated Sep. 14, 2010, U.S. District Court for the District of New Jersey (Civil Action No. 09-cv-06383 (JLL/ES)).
Transcript of Proceedings held on Sep. 15, 2010, before Judge Esther Salas, U.S. District Court for the District of New Jersey (Civil Action No. 09-cv-06383 (JLL/ES)).
Plaintiffs' Opening Claim Construction Brief, dated Sep. 29, 2010, U.S. District Court for the District of New Jersey (Civil Action No. 09-cv-06383 (JLL/ES)).
Declaration of Antonio M. Gotto, dated Sep. 29, 2010, U.S. District Court cm the District of New Jersey (Civil Action No. 09-cv-06383 (JLL/ES)).
Declaration of Gerald S. Brenner, dated Sep. 29, 2010, U.S. District Court for the District of New Jersey (Civil Action No. 09-cv-06383 (JLL/ES).
Declaration of James Suh in Support of Plaintiffs' Opening Claim Construction Brief, dated Sep. 29, 2010, U.S District Court for the District of New Jersey (Civil Action No. 09-cv-06383 (JLL/ES)).
Declaration of Srilakshmi M. Ravi, dated Sep. 29, 2010, U.S. District Court for the District of New Jersey (Civil Action No. 09-cv-06383 (JLL/ES)).
Mylan's Opening Claim Construction Brief (Redacted), dated Sep. 30, 2010, U.S. District Court for the District of New Jersey (Civil Action No. 09-cv-06383 (JLL/ES)).
Brief in Response to Defendant's Opening Markman Brief filed by MSP Singapore Company LLC, Schering Corporation (Redacted) (Attachments: # 1 Supplemental Declaration of James Suh, # 2 Supp. Suh Declaration, Exhibit 38, # 3 Supp. Suh Declaration, Exhibit 39, # 4 Supp. Suh Declaration, Exhibit 40, # 5 Supp. Suh Declaration, Exhibit 41 (Redacted)), dated Nov. 19, 2010, U.S. District Court for the District of New Jersey (Civil Action No. 09-cv-06383 (JLL/ES)).
Declaration of Srilakshmi M. Ravi (Supplemental) by Mylan Pharmaceuticals Inc., (Attachments: # 1 Exhibit 36 to the Declaration (Supplemental) of Srilakshmi M. Ravi, # 2 Exhibit 37 to the Declaration (Supplemental) of Srilakshmi M. Ravi, # 3 Exhibit 38 to the Declaration (Supplemental) of Srilakshmi M. Ravi, # 4 Exhibit 39 to the Declaration (Supplemental) of Srilakshmi M. Ravi), dated Nov. 19, 2010, U.S. District Court for the District of New Jersey (Civil Action No. 09-cv-06383 (JLL/ES)).
Brief—Mylan's Responsive Claim Construction Brief filed by Mylan Pharmaceuticals Inc.. (Attachments: # 1 Exhibit 40 to the Declaration (Supplemental) of Srilakshmi M. Ravi), dated Nov. 19, 2010, U.S. District Court for the District of New Jersey (Civil Action No. 09-cv-06383 (JLL/ES)).
Defendant Mylan Pharmaceuticals Inc.'s Answer To Plaintiffs' Complaint, Separate Defenses and Counterclaims, dated Jul. 28, 2010, U.S. District Court for the District of New Jersey (Civil Action No. 10-cv-03085 (JLL-ES)).
Defendant Impax Laboratories, Inc.'s Answer, Affirmative Defenses, Counterclaims and Jury Demand, dated Sep. 24, 2010, U.S. District Court for the District of New Jersey (Civil Action No. 10-cv-04270 (JLL-CCC)).
Plaintiffs' Answer to Impax Laboratories, Inc.'s Counterclaims, dated Oct. 15, 2010, U.S. District Court for the District of New Jersey (Civil Action No. 10-cv-04270 (JLL-CCC)).
Teva Pharmaceuticals USA, Inc.'s Answer to Complaint (Attachments: Certification Pursuant to Local Civile Rule 11.2), dated Oct. 7, 2010, U.S. District Court for the District of New Jersey (Civil Action No. 10-cv-04473 (JLL/ES)).
Plaintiffs' Answer to Teva Pharmaceuticals USA, Inc.'s Counterclaims, dated Nov. 15, 2010, U.S. District Court for the District of New Jersey (Civil Action No. 10-cv-04473 (JLL/ES)).
Stipulation regarding Teva Pharmaceutical Industries Ltd. And Order, dated Nov. 15, 2010, U.S. District Court for the District of New Jersey (Civil Action No. 10-cv-04473 (JLL/ES)).
Consent Judgment on Counterclaim, dated Nov. 15, 2010, U.S. District Court for the District of New Jersey (Civil Action No. 10-cv-04473 (JLL/ES)).
Schering Notice of Application for Application Under Section 55.2 of the Patent Act and Section 6 of the Patented Medicines (Notice of Compliance) Regulations, SOR/93-133, as am. SOR/98-166; SOR/99-379; SOR/06-242; SOR/2008-211, dated Oct. 17, 2008, Federal Court of Canada (Court File No. T-1610-08).
Deposition Transcript of Leslie Z. Benet, Ph.D., dated Oct. 1, 2009, Federal Court of Canada (Court File No. T-1610-08).
Statement for the Record in re Deposition of Leslie Z. Benet, Ph.D., dated Oct. 1, 2009, Federal Court of Canada (Court File No. T-1610-08).
Deposition of Neal Castagnoli, Ph.D., dated Nov. 6, 2009, Federal Court of Canada (Court File No. T-1610-08).
Deposition of Antonio M. Gotto, Jr., M.D., D. Phil., dated Nov. 23, 2009, Federal Court of Canada (Court File No. T-1610-08).
Cross Examination Transcript of Gary Thiessen, dated Sep. 15, 2009, Federal Court of Canada (Court File No. T-1610-08).
Cross-Examination transcript of Mark Wentland, dated Dec. 4, 2009, Federal Court of Canada (Court File No. T-1610-08).
Cross-Examination transcript of John W. Clader, dated Dec. 9, 2009, Federal Court of Canada (Court File No. T-1610-08).
Affidavit of John D. Sutherland, dated Apr. 6, 2009, Federal Court of Canada (Court File No. T-1610-08).

Affidavit of A. Louise McLean, dated Apr. 9, 2009, Federal Court of Canada (Court File No. T-1610-08).
Affidavit of Glenn Ikeda, dated Apr. 13, 2009, Federal Court of Canada (Court File No. T-1610-08).
Affidavit of Dr. John Clader (Inventor) re: Application Under Section 55.2 of the Patent Act and Section 6 of the Patented Medicines (Notice of Compliance) Regulations, SOR/93-133, as am. SOR/98-166; SOR/99-379; SOR/06-242; SOR/2008-211, dated Jun. 26, 2009, Federal Court of Canada (Court File No. T-1610-08).
Affidavit of Gary Thiessen re: Application Under Section 55.2 of the Patent Act and Section 6 of the Patented Medicines (Notice of Compliance) Regulations, SOR/93-133, as am. SOR/98-166; SOR199-379; SSR/06-242; SOR/2008-211, dated Jun. 30, 2009, Federal Court of Canada (Court File No. T-1610-08).
Affidavit of Neal Castagnoli, Ph.D. re: Application Under Section 55.2 of the Patent Act and Section 6 of the Patented Medicines (Notice of Compliance) Regulations. SOR/93-133, as am. SOR/98-166; SOR/99-379; SOR/06-242; SOR/2008-211, dated Jul. 2, 2009, Federal Court of Canada (Court File No. T-1610-08).
Affidavit of Leslie Z. Benet re: Application Under Section 55.2 of the Patent Act and Section 6 of the Patented Medicines (Notice of Compliance) Regulations, SOR/93-133, as am. SOR/98-166; SOR199-379; SOR/06-242; SOR/2008-211, dated Jul. 2, 2009, Federal Court of Canada (Court File No. T-1610-08).
Affidavit of Sonia Atwell re: Application Under Section 55.2 of the Patent Act and Section 6 of the Patented Medicines (Notice of Compliance) Regulations, SOR/93-133, as am. SSR/98-66; SOR199-379; SOR/06-242; SOR/2008-211, dated Jul. 3, 2009, Federal Court of Canada (Court File No. T-1610-08).
Affidavit of Mark Wentland re: Application Under Section 55.2 of the Patent Act and Section 6 of the Patented Medicines (Notice of Compliance) Regulations, SOR/93-133, as am. SOR/98-166; SOR199-379; SOR/06-242; SOR/2008-211, dated Jul. 3, 2009, Federal Court of Canada (Court File No. T-1610-08).
Affidavit of Antonio M. Gotta Jr., M.D., D.Phil. re: Application Under Section 55.2 of the Patent Act and Section 6 of the Patented Medicines (Notice of Compliance) Regulations, SOR/93-133, as am. SOR/98-166; SOR/99-379; SOR/06-242; SOR/2008-211, dated Jul. 6, 2009, Federal Court of Canada (Court File No. T-1610-08).
Reply Affidavit of John D. Sutherland, dated Oct. 1, 2009, Federal Court of Canada (Court File No. T-1610-08).
Deposition Transcript of Dr. John Sutherland (Cross-examination), dated Oct. 20, 2009, Federal Court of Canada (Cout File No. T.1610-08).
Memorandum of Fact and Law of the Respondent NovoPharm Limited ("TEVA"), dated Mar. 29, 2010, Federal Court of Canada (Court File No. T-1610-08).
Letter from counsel for Mylan Pharmaceuticals Inc. to MSP Singapore Co., Schering Corp,, and Merck & Co., Inc. re: Notification of Certification of Noninfringement and/or Invalidity for U.S. Patent Nos. 5,846,966 and RE37,712 Pursuant to §505(j)(2)(B)(ii) of the U.S Federal Food, Drug and Cosmetic Act. dated Nov. 5, 2009.
Letter from Teva Pharmaceuticals USA, Inc. to Merck & Co, Inc., MSP Singapore Company, LLC and Schering Corporation re: Notice of ANDA No. 200909 Concerning Ezetimibe/Simvastatin Tablets, 10 mg/80 mg with Paragraph IV Certification Concerning U.S. Patent Nos. 5,846,966 and RE37,721, dated Feb. 19, 2010.
Letter from counsel for Mylan Pharmaceuticals Inc. to MSP Singapore Co., Schering Corp., and Merck & Co., Inc. re: Notification of Certification of Noninfringement and/or Invalidity for U.S. Patent Nos. 5,846,966 and RE37,712 Pursuant to §505(j)(2)(B)(ii) of the U.S Federal Food, Drug and Cosmetic Act, dated May 25, 2010.
Letter from Impax Laboratories, Inc. to MSP Singapore Co. LLC, Merck & Co., Inc. and Schering Corporation. re: Paragraph IV Patent Certification Notice for U.S. Patent Nos. RE37,712 and 5,846,966, dated Jul. 9, 2010.
Letter from Teva Pharmaceuticals USA, Inc, to Merck & Co, Inc., MSP Singapore Company, LLC and Schering Corporation re: Notice of ANDA No. 078724 Concerning Ezetimibe Tablets, 10 mg with Paragraph IV Certification Concerning U.S. Patent Nos. 5,846,966 and RE37,721 and 7,612,058, dated Jul. 20, 2010.
Arnerican Heart Association/American Stroke Association Report Dec. 2009, "Facts: Breaking Our Hearts: Still America's No. 1 Killer," formerly accessible at http://www.americanheart.org/presenter.jhdml?identifierequal3049018 (cited as document C32 in the Information Disclosure Statement dated Aug. 13, 2010 in U.S. Appl. No. 12/797,341).
Boersma et al., Role of Cytochromes P-450 and Flavin-Containing Monooxygenase in the Biotransformation of 4-Fluoro-N-Methylaniline, Drug Metab. Dispos. 21(2):218-230 (1993) (full copy) (cited in abstract form as document C52 in the Information Disclosure Statement dated Aug. 13, 2010 in U.S. Appl. No. 12/797,341).
Davis, Harry R.; Declaration of Harry R. Davis under 37 C.F.R, 1.132 dated May 8, 1996 from file history of U.S. Appl. No. 08/257,593.
Davis, Harry R.; Declaration of Harry R. Davis under 37 C.F.R, 1.132 dated Jan. 27, 1997 from file history of U.S. Appl. No. 08/449,978.
Dollery et al., (eds) Therapeutic Drugs, vol. 1, Churchill Livingstone, Edinburgh (1991).
Dujovne et al., Reduction of LDL Cholesterol in Patients with Primary Hypercholesterolemia by SCH 48461: Results of a Multicenter Dose-Ranging Study, J. Clin Pharmacology 41:70-78 (2001) (full copy) (cited in abstract form as document C106 in the Information Disclosure Statement dated Aug. 13, 2010 in U.S. Appl. No. 12/797,341).
Grundy et al., Implications of Recent Clinical Trials for the National Cholesterol Education Program Adult Treatment Panel III Guidelines, Circulation 110(2):227-239 (2004).
Hobbs et al., Pharmacokinetics of prazosin in man, J. Clin. Pharmacol. 18(8):402-6 (1978) (full copy) (cited in abstract form as document C143 in the Information Disclosure Statement dated Aug. 13, 2010 in U.S. Appl. No. 12/797,3741).
Jackevicius, C. A. et al., "Long-term Trends in Use of and Expenditures for Cardiovascular Medications in Canada," Canadian Medical Association Journal, 181(1-2):E19-E28, Jul. 7, 2009 (cited as document C156 in the Information Disclosure Statement dated Aug. 13, 2010 in U.S. Appl. No. 12/797,341).
Low and Castagnoli, "Metabolic changes of drugs and related organic compounds," In *Wilson and Gisvold's textbook of organic medicinal and pharmaceutical chemistry*, Robert F. Doerge, Ed., 8$^{th}$ Ed., J.B. Lippincott Company, pp. 55-127 (1982).
Low and Castagnoli, "Metabolic changes of drugs and related organic compounds," In *Wilson and Gisvold's textbook of organic medicinal and pharmaceutical chemistry*, Jaime N. Delgado and William A. Remers, Eds., 9$^{th}$ Ed., J.B. Lippincott Company, pp. 45-127 (1991).
Ortiz de Montellano, ed., Cytochrome P-450. Structure, Mechanism, and Biochemistry, Ch. 7, Part 3.5, Heteroaton Oxidation and Dealkylation, Plenum Press (1986).
Otto et al., Darstellung und Stereochemie von 3-α-Hydroxybenzyl)-1,4-diphenyl-2-azetidononen, Liebigs Ann. Chem., vol. 1983, issue 7, pp. 1152-1161 (Aug. 15, 1983) (cited as document C16 in the Information Disclosure Statement dated Jul. 7, 2010 in U.S. Appl. No. 12/797,341).
Physician's Desk Reference, 46$^{th}$ Ed., pp. 1538, 1559-1560 (1992).
Regårdh et al., Plasma Levels and β-Blocking Effect of Hydroxymetoprolol—Metabolite of Metopropol in the Dog, J. Pharm. and Biopharm. 7(5)471-479 (1979) (full copy) (cited in abstract from as document C235 in the Information Disclosure Statement dated Aug. 13, 2010 in U.S. Appl. No. 12/797,341).
Sybertz, E. J., et al., "SCH 48461, a novel inhibitor of cholesterol absorption,"Atherosclerosis X (proceedings of the 10th International Symposium on Atherosclerosis, Montreal, Quebec, Oct. 9-14, 1994), Pub. Elsevier; pp. 311-315, eds. Woodford, F.P. Davington, J. & Sniderman A. (cited as document C24 in the Information Disclosure Statement dated Jul. 7, 2010 in U.S. Appl. No. 12/797,341).
Simova, E. "Aldol-type addition of hydrocinnamic acid esters to benzylideneaniline", Chemical Abstracts No. 15, vol. 86, Apr. 11, 1977, Abstract 106130h.
Otto et al., Stereochemistry of dehydration and halogenation of αR* and αS* isomeric 3-(α-hydroxybenzyl)-1,4-diphenyl=2-azetidinones, Chemical Abstracts No. 19, vol. 99, Nov. 7, 1983 abstract 158083h.
Nobuki, O. et al. "Stereoselective syntheses of β-lactam derivatives by ultrasound promoted Reformatskii reaction" Chemical Abstracts No. 106, vol. 17, Apr. 27, 1977 abstract 138174y.

T. Durst et al., 1971, "Metallation of N-Substituted β-Lactams. A Method for the Introduction of 3-Substituents into β-Lactams" *Canadian Journal of Chemistry*, 50:3196-3201.
C. Allain et al., 1974, "Enzymatic Determination of Total Serum Cholesterol" *Clinical Chemical*, 20:470-475.
R. Mayrhofer et al. 1980. "Simple Preparation of 3-Benzylidene-2-azetilidinones" *Synthesis*, 247-248.
M. Hoekman et al., 1982, "Synthesis of Homologues of 4.5-Dihydroxy- and 4-Hydroxy-5-oxohexanoic Acid-Lactones", *J. Agric. Food Chem.,* 30:920-924.
H. Otto et al., 1983, "Darstellung und Stereochemic von 3-(α-Hydroxybenzyl)-1,4-diphenyl-azetidononen", *Liebigs Ann. Chem.* 1152-1161.
G. George et al., 1985 "3-(T-Hydroxyethyl)-2-Azetidinones From 3-Hdyroxy-butyrates and N-Arylaldimines" *Tetrahedron Letters*, vol. 26, No. 33 pp. 3903-3906.
Hart et al., 1985 "An Enantioselective Approach to Carhapenen Antibodies: Formal Synthesis of (+)-Thienamycin" *Tetrahedron Letters*, vol. 26, No. 45 pp. 5493-5496.
Pantil. I. et al., 1986, "Synthesis of β-Lactams from α, β-Unsaturated Sugar δ-Lactones" *Heterocycles* 34:1609-1617.
D. Roger Hlingworth, 1988, "An Overview of Lipid-Lower Drugs" *Drugs* 36:63:71.
Joseph L. Witztum, M.D., 1989, "CUrrent Approaches to Drug Therapy for the Hyercholesterolemic Patient" *Circulation* 80:1101-1114.
B. Ram et al., 1990, "Potential hypolipidemic agents:Part V†-Synthesis biological activity of new ethyl 4-(2-oxoazetidin-4-yl)phenoxyalkanoates‡" *Indian Journal of Chemistry* 29B:1134-1137.
Schnitzer-Polokoff, R. et al. 1991, "Effects of Acyl-CoA: Cholesterol O-Acyltransferase Inhibition on Cholesterol Absorption and Plasma lipoprotein Composition in Hamsters" *Comp. Biochem. Physiol.* 99A:665-670.
Horie, M. et al. 1991, "Hypolipidemic effects of NB-598 in dogs" *Atherosclerosis* 88:183-192.
Baxter, A., 1992, "Squalestatin 1, a Potent Inhibitor of Squalene Synthase, Which Lowers Serum Cholesterol in Vivo," *The Journal of Biological Chemistry* 267:11705-11708.
Summary Factile, May 1992, "Anti-Antherosclerotic Agents" Current Drugs Ltd. pp. A5-A23.
Harwood, H. James, 1993, "Pharmacologic consequences of cholesterol absorption inhibition: alteration in cholesterol metabolism and reduction in plasma cholesterol concentration induced by the synthetic saponin β-tigogenin cellobioside (CP-88818;tiqueside)[1] " *Journal of Lipid Research* 34:377-395.
Salisbury, B. et al., 1995, "Hypocholesterolemic activity of a novel inhibitor of cholesterol absorption, SCH 48461" *Atherosclerosis* 115:45-63.
Burrier, R.E. et al., 1994, "Demonstration of a Direct Effect on Hepatic Acyl CoA:Cholesterol Acyl Transferase (ACAT) Activity By An Orally Administered Enzyme Inhibitor in the Hamster", *Biochemical Pharmacology* 47:1545-1551.
Burrier, R.E. et al., 1994, "The Effect of Acyl CoA:Cholesterol Acyltransferase Inhibition on the Uptake, Esterification and Secretion of Cholesterol by the Hamster Small Intestine", *The Journal of Pharmacology and Experimental Therapeutics* 272:156-163.
Clader, J.W. et al., 1995, "Substituted (1,2-Diarylethyl)amide Acyl-CoA:Cholesterol Acyltransferase Inhibitors: Effect of Polar Groups in Vitro and in Vivo Activity" *Journal of Medicinal Chemistry* 38:1600-1607.
Sybertz, E. 1995, "SCH 48461, a novel inhibitor of cholesterol absorption" *Atherosclerosis* pp. 311-315.

HYDROXY-SUBSTITUTED AZETIDINONE COMPOUNDS USEFUL AS HYPOCHOLESTEROLEMIC AGENTS

Matter enclosed in heavy brackets [ ] appears in the original patent but forms no part of the first and this reissue specification; matter printed in italics indicates the additions made by the first reissue. Matter enclosed in double heavy brackets [[ ]] appears in the first reissue patent but forms no part of this reissue specification; matter printed in bold face indicates the additions made by this reissue.

The present application is the United States national application corresponding to International Application No. PCT/US94/10099, filed Sep. 14, 1994 and designating the United States, which PCT application is in turn a continuation-in-part of U.S. application Ser. No. 08/257593, filed Jun. 9, 1994, U.S. Pat. No. 5,631,365, which is a continuation-in-part of U.S. application Ser. No. 08/102,440, filed Sep. 21, 1993, abandoned.

BACKGROUND OF THE INVENTION

The present invention rotates to hydroxy-substituted azetidinones useful as hypocholesterolemic agents in the treatment prevention of atherosclerosis, and to the combination of a hydroxy-substituted azetidinone of this invention and a cholesterol bioxynthesis inhibitor for the treatment and prevention of atherosclerosis. The invention also relates to a process for preparing hydroxy-substituted azetidinones.

Atherosclerotic coronary heart disease (CHD) represents the major cause for death and cardiovascular morbidity in the western world. Risk factors for atherosclerotic coronary heart disease include hypertension, diabetes mellitus, family history, male gender, cigar smoke and serum cholesterol. A total cholesterol level in excess of 225-250 mg/dl is associated with significant elevation of risk of CHD.

Cholesteryl esters are a major component of atherosclerotic lesions and the major storage form of cholesterol in arterial wall cells. Formation of cholesteryl esters is also a key step in the intestinal absorption of dietary cholesterol. Thus, inhibition of cholesteryl ester formation and reduction of serum cholesterol is likely to inhibit the progression of atherosclerotic lesion formation, decrease the accumulation of cholesterol esters in the arterial wall, and block the intestinal absorption of dietary cholesterol.

A few azetidinones have been reported as being useful lowering cholesterol and/or in inhibiting the formation of cholesterol-containing lesions in mammalian arterial walls. U.S. Pat. No. 4,983,597 discloses N-sulfonyl-2-azetichnones as anticholesterolemic agents and Ram, et al., in Indian J. Chem., Sect. B. 29B, 12 (1990), p. 1134-7, disclose ethyl 4-(2-oxoazetidin-4-yl)phenoxy-alkanoates as hypolipidemic agents. European Patent Publication 264,231 discloses 1-substituted-4-phenyl-3-(2-oxo-alkylidene)-2-azetidinones as blood platelet aggregation inhibitors. European Patent 199,630 and European Patent Application 337,549 disclose elastase inhibitory substituted azetidinones said to be useful treating inflammatory conditions resulting in tissue destruction which are associated with various disease states, e.g. atherosclerosis.

WO93/102048, published Feb. 4, 1993, discloses substituted β-lactams useful as hypocholesterolemic agents.

The regulation of whole-body cholesterol homeostasis in humans and animals involves the regulation of dietary cholesterol and modulation of cholesterol biosynthesis, bile acid biosynthesis and the catabolism of the cholesterol-containing plasma lipoproteins. The liver is the major organ responsible for cholesterol biosynthesis and catabolism and for this reason, it is a prime determinant of plasma cholesterol levels. The liver is the site of synthesis and secretion of very low density lipoproteins (VLDL) which are subsequently metabolized to low density lipoproteins (LDL) in the circulation. LDL are the predominant cholesterol-carrying lipoproteins in the plasma and an increase in their concentration is correlated with increased atherosclerosis.

When intestinal cholesterol absorption is reduced, by whatever means, less cholesterol is delivered to the liver. The consequence of this action is decreased hepatic lipoprotein (VLDL), production and an increase in the hepatic clearance of plasma cholesterol, mostly as LDL. Thus, the net effect of inhibiting intestinal cholesterol absorption is a decrease in plasma cholesterol levels.

The inhibition of cholesterol biosynthesis by 3-hydroxy-3-methylglutaryl coenzyme A (HMG CoA) reductase (EC1.1.1.34) inhibitors has been shown to be an effective way to reduce plasma cholesterol (Witzum, Circulation, 80, 5 (1989), p. 1101-1114) and reduce atherosclerosis. Combination therapy of an HMG CoA reductase inhibitor and a bile acid sequestrant has been demonstrated to be more effective in human hyperlipidemic patients than either agent in monotherapy (Illingworth, Drugs, 36 (Suppl. 3) (1988), p. 63-71).

SUMMARY OF THE INVENTION

Novel hypocholesterolemic compounds of the present invention are represented by the formula I

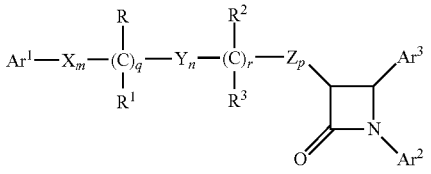

I or a pharmaceutically acceptable salt thereof, wherein:

$Ar^1$ and $Ar^2$ are independently selected from the group consisting of aryl and $R^4$-substituted aryl;

$Ar^3$ is aryl or $R^5$-substituted aryl;

X, Y and Z are independently selected from the group consisting of —$CH_2$—, —CH(lower alkyl)— and —C(dilower alkyl)—;

R and $R^2$ are independently selected from the group consisting of —$OR^6$, —O(CO)$R^6$, —O(CO)$OR^9$ and —O(CO)$NR^6R^7$;

$R^1$ and $R^3$ are independently selected from the group consisting of hydrogen, lower alkyl and aryl;

q is 0 or 1; r is 0 or 1; m, n and p are independently 0, 1, 2, 3 or 4; provided that at least One of q and r is 1, and the sum of m, n, p, q are r is 1, 2, 3, 4, 5 or 6; and provided that when p is 0 and r is 1, the sum of m, q and n is 1, 2, 3, 4, or 5;

$R^4$ is 1-5 substituents independently selected from the group consisting of lower alkyl, —$OR^6$, —O(CO)[$R_6$,]$R^6$, —O(CO)$OR^9$, —O$(CH_2)_{1-5}OR^6$, —O(CO)$NR^6R^7$, —$NR^6R^7$, —$NR^6$(CO)$R^7$, —$NR^6$(CO)$OR^9$, —$NR^6$(CO)$NR^7R^8$, —$NR^6SO_2R^9$, —$COOR^6$, —$CONR^6R^7$, —$COR^6$, —$SO_2NR^6R^7$, S$(O)_{0-2}R^9$, —O$(CH_2)_{1-10}$—$COOR^6$, —O$(CH_2)_{1-10}CONR^6R^7$, —(lower alkylene)$COOR^6$, —CH═CH—$COOR^6$, —$CF_3$, —CN, —$NO_2$ and halogen;

$R^5$ is 1-5 substituents independently selected from the group consisting of —$OR^6$, —$O(CO)R^6$, —$O(CO)OR^9$, —$O(CH_2)_{1-5}OR^6$, —$O(CO)NR^6R^7$, —$NR^6R^7$, —$NR^6(CO)R^7$, —$NR^6(CO)OR^9$, —$NR^6(CO)NR^7R^8$, —$NR^6SO_2R^9$, —$COOR^6$, —$CONR^6R^7$, —$COR^6$, —$SO_2NR^6R^7$, $S(O)_{0-2}R^9$, —$O(CH_2)_{1-10}$—$COOR^6$, —$O(CH_2)_{1-10}CONR^6R^7$, —(lower alkylene)$COOR^6$ and —CH═CH—$COOR^6$;

$R^6$, $R^7$ and $R^8$ are independently selected from the group consisting of hydrogen, lower alkyl, aryl and aryl-substituted lower alkyl; and $R^9$ is lower alkyl, aryl or aryl-substituted lower alkyl.

$R^4$ is preferably 1-3 independently selected substituents, and $R^5$ is preferably 1-3 independently selected substituents. Preferred are compounds of formula I wherein $Ar^1$ is phenyl or $R^4$-substituted phenyl, especially (4-$R^4$)-substituted phenyl, $Ar^2$ is preferably phenyl or $R^4$-substituted phenyl, especially (4-$R^4$)-substituted phenyl. $Ar^3$ is preferably $R^5$-substituted phenyl, especially (4-$R^5$)-substituted phenyl. When $Ar^1$ is (4-$R^4$)-substituted phenyl, $R^4$ is preferably a halogen. When $Ar^2$ and $Ar^3$ are $R^4$- and $R^5$-substituted phenyl, respectively, $R^4$ is preferably halogen or —$OR^6$ and $R^5$ is preferably —$OR^6$, wherein $R_6$ is lower alkyl or hydrogen. Especially preferred are compounds wherein each of $Ar^1$ and $Ar^2$ is 4-fluorophenyl and $Ar^3$ is 4-hydroxyphenyl or 4-methoxyphenyl.

X, Y and Z are each preferably —$CH_2$—.$R^1$ and $R^3$ are each preferably hydrogen. R and $R^2$ are preferably —$OR^6$ wherein $R^6$ is hydrogen, or a group readily metabolizable to a hydroxyl (such as —$O(CO)R^6$, [—$O(CO)OR^9$ and] —*$OR^6$*, especially —$O(CO)NR^6R^7$, defined above).

The sum of m, n, p, q and r is preferably 2, 3 or 4, more preferably 3. Preferred are compounds wherein m, n and r are each zero, q is 1 and p is 2. Also preferred are compounds wherein p, q and n are each zero, r is 1 and m is 2 or 3. More preferred are compounds wherein m, n and r are each zero, q is 1, p is 2, Z is —$CH_2$ and R is —$OR^6OR_6$, especially when $R^6$ is hydrogen. Also more preferred are compounds wherein p, q and n are each zero, r is 1, m is 2, X is —$CH_2$— and $R^2$ is —$OR^6$, especially when $R^6$ is hydrogen.

Another group of preferred compounds is that wherein $Ar^1$ is phenyl or $R^4$-substituted phenyl, $Ar^2$ is phenyl or $R^4$-substituted phenyl and $Ar^3$ is $R^5$-substituted phenyl. Also preferred are compounds wherein $Ar^1$ is phenyl or $R^4$-substituted phenyl, $Ar^2$ is phenyl or $R^4$-substituted phenyl, $Ar^3$is $R^5$-substituted phenyl, and the sum of m, n, p, q and r is 2, 3 or 4, more especially 3. More preferred are compounds wherein $Ar^1$ is phenyl or $R^4$-substituted phenyl, $Ar^2$ is phenyl or $R^4$-substituted phenyl $Ar^3$ is $R^5$-substituted phenyl, and wherein m, n and r are each zero, q is 1 and p is 2, or wherein p, q and n are each zero, r is 1 and m is 2 or 3.

This invention also relates to a method of lowering the serum cholesterol level in a mammal in need of such treatment comprising administering an effective amount of a compound of formula I. That is, the use of a compound of the present invention as an hypocholesterolemic agent is also claimed.

In still another aspect, the present invention relates to a pharmaceutical composition comprising a serum cholesterol-lowering effective amount of a compound of formula I in a pharmaceutically acceptable carrier.

The present invention also relates to a method of reducing plasma cholesterol levels, and to a method of treating or preventing atherosclerosis, comprising administering to a mammal in need of such treatment an effective amount of a combination of a hydroxy-substituted azetidinone cholesterol absorption inhibitor of formula I and a cholesterol biosynthesis inhibitor. That is, the present invention relates to the use of a hydroxy-substituted azetidinone cholesterol absorption inhibitor of formula I for combined use with a cholesterol biosynthesis inhibitor (and, similarly, use of a cholesterol biosynthesis inhibitor for combined use with a hydroxy-substituted azetidinone cholesterol absorption inhibitor of formula I) to treat or prevent atherosclerosis or to reduce plasma cholesterol levels.

In yet another aspect, the invention relates to a pharmaceutical composition comprising an effective amount of a hydroxy-substituted azetidinone cholesterol absorption inhibitor of formula I, a cholesterol biosynthesis inhibitor, and a pharmaceutically acceptable carrier. In a final aspect, the invention relates to a kit comprising in one container an effective amount of a hydroxy-substituted azetidinone cholesterol absorption inhibitor of formula I in a pharmaceutically acceptable carrier, and in a separate container, an effective amount of a cholesterol biosynthesis inhibitor in a pharmaceutically acceptable carrier.

In yet another aspect, the invention relates to a process for preparing certain compounds of formula I comprising the steps:

(a) treating with a strong base a lactone of the formula

A

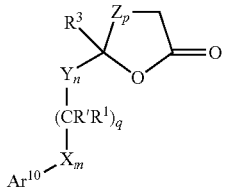

or

B

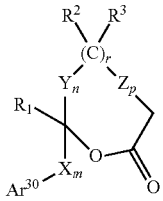

wherein R' and $R^{2'}$ are R and $R^2$, respectively, or are suitably protected hydroxy groups; $Ar^{10}$ is $Ar^1$, a suitably protected hydroxy substituted aryl or a suitably protected amino-substituted aryl; and the remaining variables are as defined above, provided that in lactone of formula B when n and r are each zero, p is 1-4;

(b) reacting the product of step (a) with an imine of the formula

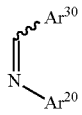

wherein $Ar^{20}$ is $Ar^2$, a suitably protected hydroxy-substituted aryl or a suitably protected amino-substituted aryl; and $Ar^{30}$ is $Ar^3$, a suitably protected hydroxy-substituted aryl or a suitably protected amino-substituted aryl;

c) quenching the reaction with an acid;

d) optionally removing the protecting groups from R', $R^{2'}$, $Ar^{10}$, $Ar^{20}$ and $Ar^{30}$, when present; and c) optionally functionalizing hydroxy or amino substituents at R, $R^2$, $Ar^1$, $Ar^2$ and $Ar^3$.

Using the lactones shown above, compounds of formula IA and IB are obtained as follows:

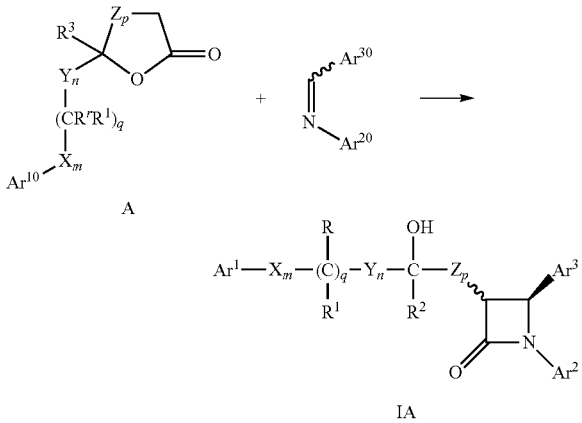

wherein the variables are as defined above; and

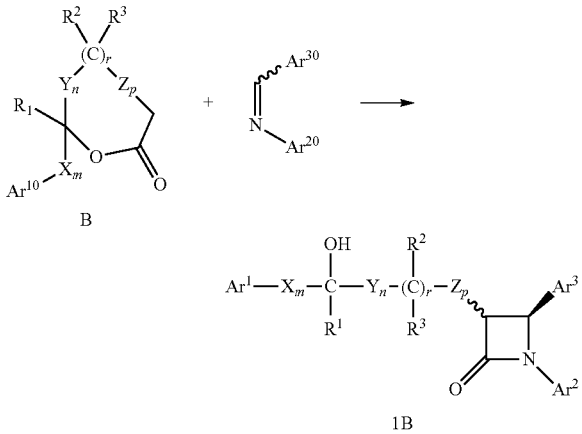

wherein the variables are as defined above.

DETAILED DESCRIPTION

As used herein, the term "lower alkyl" means straight or branched alkyl chains of 1 to 6 carbon atoms.

"Aryl" means phenyl, naphthyl, indenyl, tetrahydronaphthyl or indanyl.

"Halogen" refers to fluorine, chlorine, bromine or iodine atoms.

The above statement, wherein $R^6$, $R^7$ and $R^8$ are said to be independently selected from a group of substituents, means that $R^6$, $R^7$ and $R^8$ are independently selected, but also that where an [$R_6$], $R^6$ or $R^8$ variable occurs more than once in a molecule, those occurrences are independently selected (e.g., if R is —$OR^6$ wherein $R^6$ is hydrogen, $R^4$ can be —$OR^6$ wherein $R^6$ is lower alkyl).

Compounds of the invention have at least one asymmetric carbon atom and therefore all isomers, including enantiomers and diastereomers are contemplated as being part of this invention. The invention includes d and [l] *l* isomers in both pure form and in admixture including racemic mixtures. Isomers can be prepared using conventional techniques, either by reacting chiral starting materials or by separating isomers of a compound of formula I. Isomers may also include geometric isomers, e.g. when a double bond is present. All such geometric isomers are contemplated for this invention.

Those skilled in the art will appreciate that for some compounds of formula I, one isomer will show greater pharmacological activity than another isomer.

Compounds of the invention with an amino group can form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salt is prepared by contacting the free base form with a sufficient amount of the desired acid to produce a salt. The free base form may be regenerated by treating the salt with a suitable dilute aqueous base solution such as dilute aqueous sodium bicarbonate. The free base form differs front its respective salt form somewhat in certain physical properties, such as solubility in polar solvents, but the salt is otherwise equivalent to its respective free base form for purposes of the invention.

Certain compounds of the invention are acidic (e.g., those compounds which possess a carboxyl group). These compounds form pharmaceutically acceptable salts with inorganic and organic bases. Examples of such salts are the sodium, potassium, calcium, aluminum, gold and silver salts. Also included are salts formed with pharmaceutically acceptable amines such as ammonia, alkyl amines, hydroxyalkylamines, N-methylglucamine and the like.

Cholesterol biosynthesis inhibitors for use in the combination or the present invention include HMG CoA reductase inhibitors such as lovastatin, pravastatin, fluvastatin, simvastatin, and Cl-981; HMG CoA synthetase inhibitors, for example L-659,699 ((E,E)-11-[3'-R-(hydroxy-methyl)-4'-oxo-2'-R-oxetanyl]-3,5,7R-trimethyl-2,4-undecadienoic (acid); squalene synthesis inhibitors, for example squalestatin 1; and squalene epoxidase inhibitors, for example, NB-598 ((E)-N-ethyl-N-(6,6-dimethyl-2-hepten-4-ynyl)-3-[(3,3'-bithiophen-5-yl)methoxy]benzene-methanamine hydrochloride) and other cholesterol biosynthesis inhibitors such as DMP-565. Preferred HMG CoA reductase inhibitors are lovastatin, pravastatin and simvastatin.

Compounds of formula I can be prepared by known methods, for example those described below and in WO93/02048.

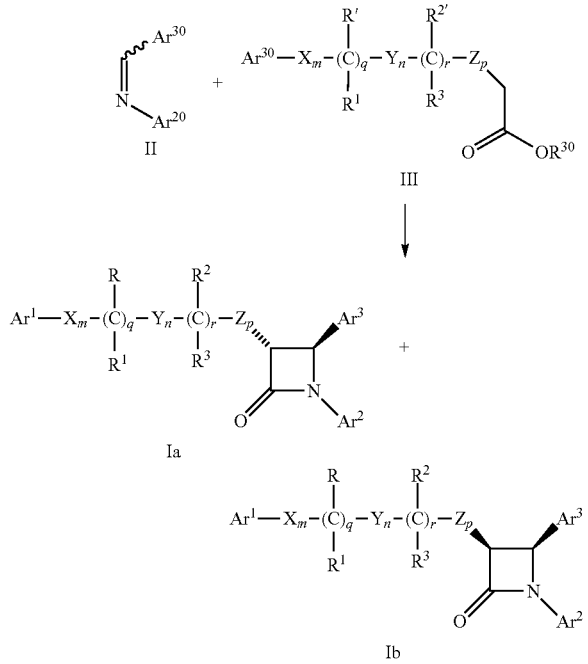

Compounds of formula Ia and Ib, wherein $Ar^1$, $Ar^2$, [Ar3,] $Ar^3$ X, Y, Z, $R^1$, $R^2$, $R^3$, m, n, p, q and r are as defined above, can be prepared by treatment of an ester of formula III, wherein $R^{10}$ is lower alkyl such as ethyl or a chiral moiety such as menthyl or 10-(diisopropylsulfonamido)isobornyl, and the remaining variables are as defined above, with a strong base such as lithium diisopropylamide (LDA) in a suitable solvent such as tetrrahydrolithium (THF) at −78° C. A solubilizing agent such as hexamethylphosphoric triamide (HMPA) may optionally be added as a cosolvent. An imine of formula 11, wherein $Ar^{20}$ and $Ar^{30}$ are as defined above, is added, the reaction mixture is either warmed to room temperature or maintained at a suitable low temperature such as −78° C. for the appropriate time, followed by quenching with a suitable acid such as 1N HCl. The product is isolated using conventional purification techniques. When a protecting group as defined in Table 1 (below) is present on one or more of the optionally protected groups, an additional step comprising removal of the protecting group by conventional techniques is needed. However, for compounds of formula Ia, Ib, or any compound of formula I wherein a protected hydroxy group $Ar^{10}$, $Ar^{20}$, $Ar^{30}$, R' or $R^{2'}$ is an alkoxy or benzyloxy group, such a protecting group need not be removed to obtain a compound of formula I. When a chiral ester of formula III is used, the resulting compound of formula Ia or Ib is not racemic.

Imines of formula II ($Ar^{30}$—CH═N—$Ar^{20}$) can be prepared from aldehydes of the formula $Ar^{30}$—CHO and amines of the formula [$Ar^{+}$—CHO and] $Ar^{20}$—$NH_2$ by procedures well known in the art. Aldehydes of formula [$Ar^{+}$] $Ar^{30}$—CHO and amines of formula $Ar^{20}$—$NH_2$ are commercially available or can be prepared via known procedures.

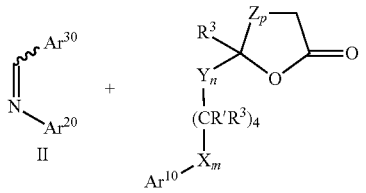

II IV

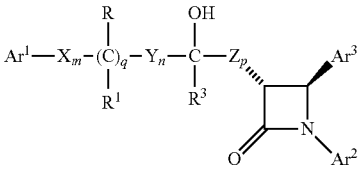

Ic

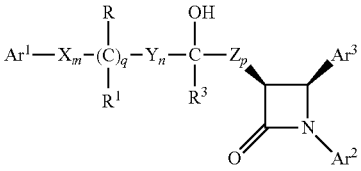

Id

Compounds of formula Ic and Id, wherein the variables are as defined above, can be prepared by a process comprising the following steps:

(a) Treat a lactone of formula IV, wherein the variables are as defined above, with a strong base such as an alkyllithium (e.g., n-butyl-lithium), a metal hydride (e.g., sodium hydride), a metal alkoxide (e.g., sodium methoxide), a metal halide (e.g., $TiCl_4$), metal exchange of the lithium enolate with a metal halide (e.g., zinc chloride), metal exchange of the lithium enolate with a metal alkyl (e.g., 9-borabicyclononyl triflate), or, preferably, a metalamide (e.g., LDA), in a suitable anhydrous organic solvent such as dry THF, ether or benzene, in a dry, inert atmosphere, e.g., under nitrogen. The reaction is carried out at about 0° C. to about −85° C., preferably about −78° C., over a period of about 5 to 60 minutes, preferably about 30 minutes. 1-50% of solubilizing cosolvents may optionally be added, preferably about 10% HMPA.

(b) Add an imine of formula 11, wherein $Ar^{20}$ and $Ar^{30}$ are as defined above, to the product of step (a) over a period of 5 to 60 minutes, preferably 30 minutes, maintaining the reaction mixture at about 0° C. to about −85° C., preferably about −78° C., for 1 to 12 hours, preferably about 3 hours, or warming the reaction mixture over that time period at a rate of about 10° C. per hour to about 70° C. per hour, preferably about 30° C. per hour, to a temperature of about 20° C.

(c) Quench the reaction with a suitable acid such as HCl (1N).

(d) The protecting groups on R', $R^{2'}$, $Ar^{10}$, $Ar^{20}$ and $Ar^{30}$, when present, are removed, if desired, by methods well known in the art, for example silyl protecting groups are removed by treatment with fluoride.

e) Compounds of formula I wherein any of R and $R^2$, when present, are $OR^6$ wherein $R^6$ is hydrogen, can be converted by well known methods to other compounds of formula I wherein R and $R^2$ are functionalized, i.e., are independently selected from the group consisting of $OR^{6a}$, —O(CO)$R^6$, —O(CO)$OR^9$ and —O(CO)$NR^6R^7$, wherein $R^6$, $R^7$ and $R^9$ are as defined above and $R^{6a}$ is lower alkyl, aryl, or aryl-lower alkyl. For example, treatment of the alcohol with an alkyl halide in the presence of a suitable base such as NaH will afford alkoxy-substituted compounds (i.e., R or $R^2$ is $OR^6$, wherein $R^6$ is lower alkyl); treatment of the alcohol with an acylating agent such as acetylchloride will result in compounds wherein R or $R^2$ is —OC(O)$R^6$; treatment of the alcohol with phosgene followed *by an* alcohol of the formula $HOR^9$ affords compounds substituted with a —OC (O)$OR^9$ group; and treatment of the alcohol with phosgene followed by an amine of the formula $HNR^6R^7$ affords compounds wherein R or $R^2$ is —OC(O)$NR^6R^7$. Compounds of formula I wherein any $Ar^1$, $Ar^2$ or $Ar^3$ has a hydroxy or amino group can be similarly functionalized to obtain other compounds of formula 1, i.e., wherein $R^4$ and $R^5$ are independently —$OR^{6a}$, —O(CO)$R^6$, —O(CO)$OR^9$, —O$(CH_2)_{1-5}OR^6$, —O(CO)$NR^6R^7$, —$NR^6R^7$, —$NR^6$(CO)$R^7$, —$NR^6$(CO)$OR^9$, —$NR^6$(CO)$NR^7R^8$ or —$NR^6SO_2R^9$.

The product of step c, d or e is isolated using conventional purification techniques such as extraction, crystallization or, preferably, silica gel 60 chromatography. When a chiral lactone is used, the resulting compound of formula Ic or Id is not racemic.

Using the procedure described in steps (a)-(e), lactones of formula IVa can be used to prepare compounds of formula Ig and Ih, provided that when n and r are each zero, p is 1-4:

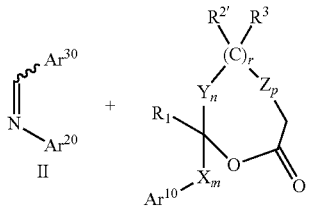

II IVa

-continued

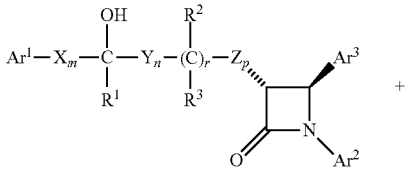

Ig

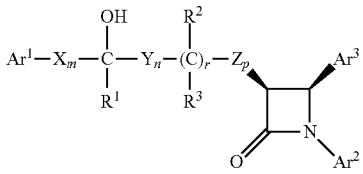

Ih

Lactones of formulae IV and IVa are known in the art or can be prepared by methods well known in the art. See, for example, U.S. Pat. No. 4,375,475 and J. Agric. Food Chem., 30 (5) (1982) p. 920-4.

Azetidinones of formula V, wherein $Ar^{20}$ and $Ar^{30}$ are as defined above, can be reacted to form compounds of formula Ie and If i.e., compounds of formula I wherein r is 1, $R^2$ is hydroxy, and p is zero) by treatment of azetidinone V with a strong base such as lithium [iosoproptylcyclohexylamide] *isopropylcyclohexylamide* in a suitable solvent such as THF in the presence or [absent] *absence* of HMPA at −78° C., followed by the addition of an aldehyde or ketone of VI, wherein $Ar^{10}$, X, Y, R', $R^1$, $R^3$, m, n and q are as defined above. As in the case of Method A, protecting groups at $Ar^{10}$, $Ar^{20}$, $Ar^{30}$, R' and $R^{2'}$ are removed as necessary.

This process provides several of the possible diasteromers which can be separated by a combination of crystallization, silica gel chromatography and HPLC, using techniques well known in the art. The remaining diastereomers can be obtained by inversion reactions such as the Mitsunobu reaction sequence outlined below, wherein partial structures of formula If are shown:

Method B:

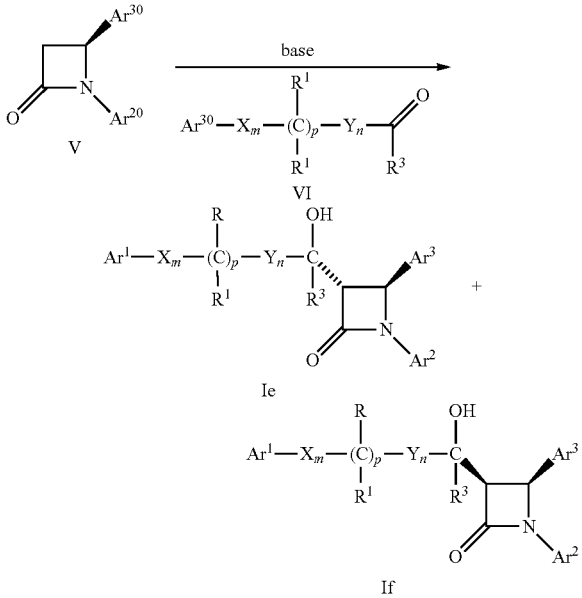

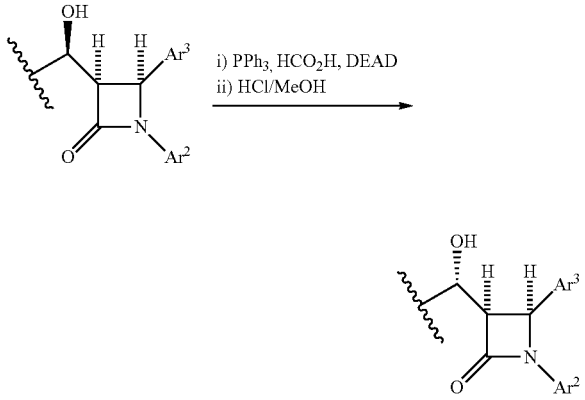

In the above known process, DEAD is diethylazodicarboxylate and $PPh_3$ is triphenylphosphine. The reactants are stirred at room temperature overnight and the resultant formate ester is converted to the corresponding hydroxy compound with the desired stereochemistry.

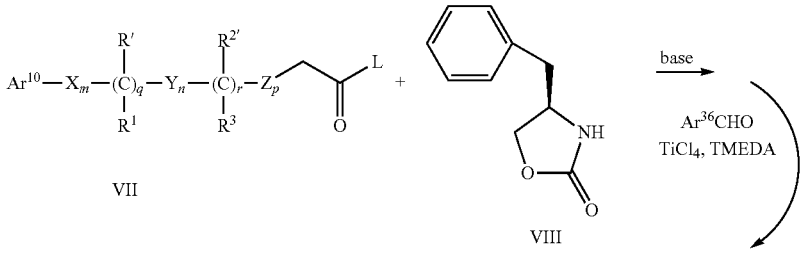

-continued

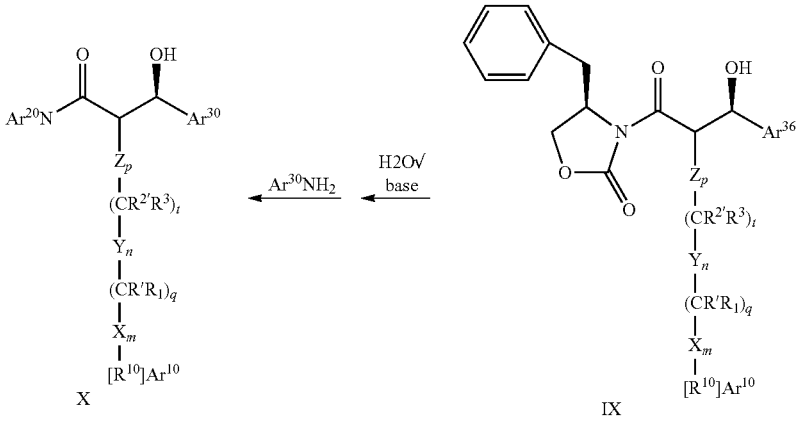

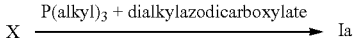

Compounds of formula Ia as defined above can be prepared by reacting a chiral auxiliary such as the compound of formula VIII with an activated carboxylic acid derivative of formula VII, for example an acid chloride (L═Cl), a mixed anhydride formed with phenyl phosphorodichloridate (L═OP(O)(Cl)OPh), an N-methyl-pyridinium ester formed from the reaction of an acid with N-methyl-2-chloropyridinium iodide (L=2-oxy-N-methylpyridinium iodide), and a 2-thiopyridyl ester formed from the reaction of an acid chloride and 2-thiopyridine, wherein the remaining variables are as defined above; enolizing the resultant product, for example with $TiCl_4$ and tetramethylethylenediamine (TMEDA); condensing with an aldehyde, $Ar^{30}CHO$; hydrolyzing to the corresponding acid, then reacting the compound of the formula IX with an amine, $Ar^{20}NH_2$; and cyclizing the resultant compound of formula X, with, for example a trialkylphosphine and a dialkylazodicarbo)ylate. As in the case of Method A, protecting groups at $Ar^{10}$, $Ar^{20}$, $Ar^{30}$, R' and $R^{2'}$ are removed as necessary. This procedure is described in detail in [WO93/102048] *WO93/02048*.

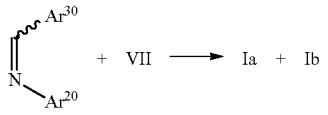

II

Compounds of formula Ia as defined above can also be prepared treatment of an imine of formula [11,] *II*, wherein $Ar^{20}$ and $Ar^{30}$ are as defined above, with an activated carboxylic acid derivative of formula VII as defined above in the presence of a tertiary amine base such as triethylamine, tributylamine or diethylisopropylamine in an inert solvent such as $CH_2Cl_2$. Again, as in the case of Method A, protecting groups at $Ar^{10}$, $Ar^{20}$, $Ar^{30}$, R' and $R^{2'}$ are removed as necessary. Use of other bases, e.g., pyridine, favors formation of compounds of formula Ib.

Method E:

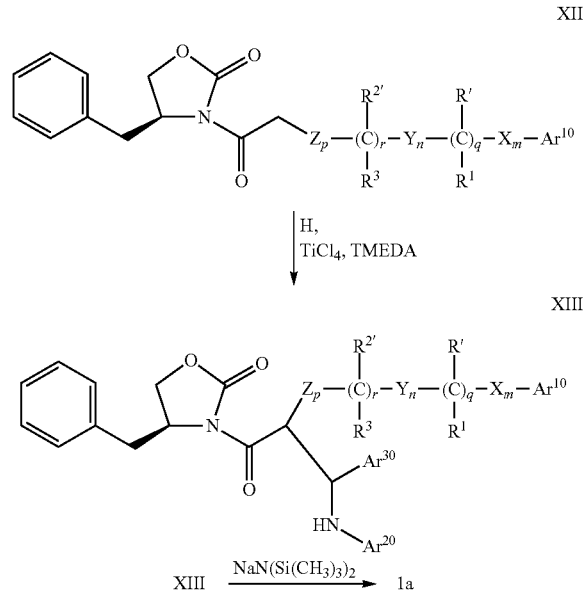

In the first step, compound XII is dissolved in a suitable solvent, e.g., anhydrous $CH_2Cl_2$, and treated with a Lewis acid, e.g., $TiCl_4$ at about −60° C. to 0° C., preferably at about −25° C., under a dry, inert atmosphere, e.g., argon. A tertiary amine base such as TMEDA is added and the mixture stirred at about −60° C. to 0° C., preferably at about −25° C. to −15° C., for a period of about 1 h. An imine of formula $Ar^{30}CH{=}NAr^{20}$ is added neat or optionally as a solution in a suitable solvent, e.g. anhydrous $CH_2Cl_2$, over a period of about 5 min, and the reaction is stirred vigorously at about −60° C. to 0° C., preferably at about −25° C. to −15° C., for about 3 to 6 h, preferably about 4 h or until the reaction is complete by TLC. An acid, e.g. acetic acid, is added to reaction at the reaction temperature and the mixture is allowed to warm to room temperature slowly with stirring for about 1-3 hours, preferably about 2 hours. The compound of formula XII is isolated by extraction with a suitable solvent, e.g. $CH_2Cl_2$, then purified by crystallization or silica gel chromatography.

In the second step, the product is treated with a strong non-nucleophilic base, such as sodium or lithium bistrimethylsilylamide at about −78° C. to 100° C. After reaction, the mixture is poured into aqueous tartaric acid and the product isolated from the organic layer. As in the case of Method A, protecting groups at $Ar^{10}$, $Ar^{20}$, $Ar^{30}$, R' and $R^{2'}$ are removed as necessary. This process, including the preparation of the starting material of formula XII, is also described in greater detail in WO93/02048.

Method F:

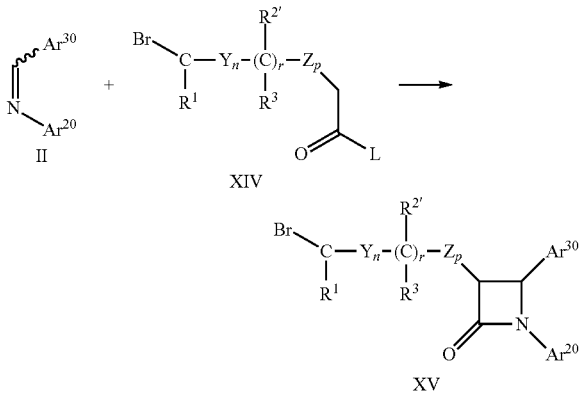

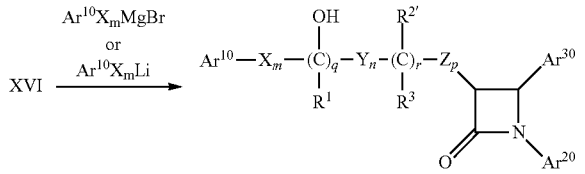

Compound of formula Ig' and Ih' (i.e., compounds of formula I wherein R is OH), wherein $R^{2'}$ is a protected hydroxy group as defined above, and the remaining variables are as defined above, can be prepared by reacting an imine of formula [11] *II* and a carboxylic acid derivative of formula XIV, wherein the variables are as defined above, according to method D, followed by oxidation of the resultant halide of formula XV by treatment with an oxidizing agent such as trimethylamine oxide, $CrO_3$ or ozone in a solvent such as DMSO. The resultant aldehyde or ketone of formula XVI is then reacted with an aryl organometallic reagent (e.g., $Ar^{10}X_mMgBr$, $Ar^{10}X_mLi$, $Ar^{10}X_mMgCl$ or $Ar^{10}X_mCeCl_2$) to obtain a compound of formula Ig' or Ih'. As described above, the $Ar^{10}$, $Ar^{20}$, $Ar^{30}$ and $R^{2'}$ substituents can be converted to the desired $Ar^1$, $Ar^2$, $Ar^3$ and $R^2$ substituents by procedures well known in the art.

Method G:

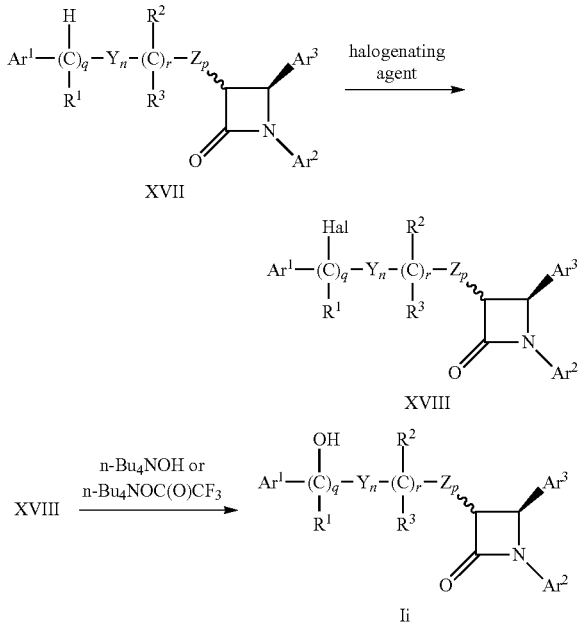

Compounds of formula Ii having a hydroxy substituent on the side chain adjacent to the $Ar^1$ group (i.e., compounds of formula I wherein m is 0) can be prepared by heating a compound of formula XVII, prepared by Method D, above, wherein the variables are as defined above, for about 1-6 hours at about 60° C. to 100° C. with a halogenating agent such as N-bromosuccinimide (NBS) in a suitable solvent such as $CCl_4$ in the presence of an initiating agent such as benzoyl peroxide. The resultant compound of formula XVIII, wherein Hal is Cl, Br or I and the remaining variables are as defined above, is then heated in a suitable solvent such as $CH_2Cl_2$ with a tetraalkyl-ammonium salt such as tetra n-butyl-ammonium hydroxide (n-$Bu_4NOH$) to obtain the compound of formula Ia. Alternatively, compound XVIII can be heated in a suitable solvent such as $CH_2Cl_2$ with tetra n-butylammonium trifluoroacetate (n-$Bu_4NOC(O)CF_3$) followed by treatment with a mild base such as ethanol saturated with [NH3] $NH_3$ to obtain compound Ii, Method H:

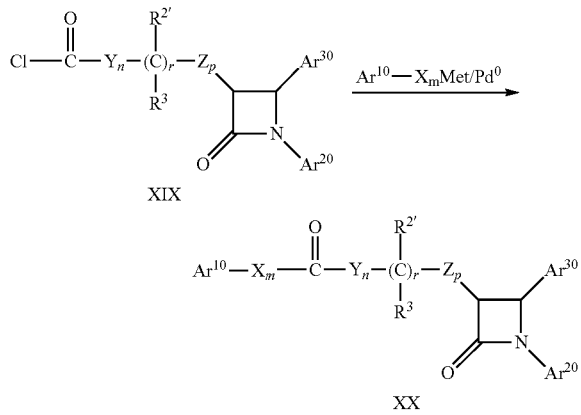

-continued

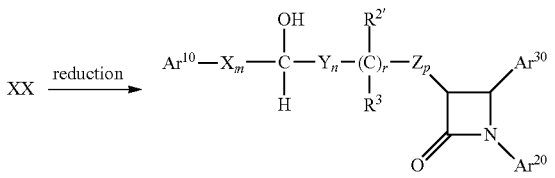

Ij

Compounds of formula Ij (i.e., compounds of formula I wherein R is OH, $R^1$ is H and q is 1) are prepared from compound XIX in 2 steps. First, a compound of formula XIX, wherein the variables are a defined above, is dissolved in a suitable anhydrous solvent, e.g. THF, at about −20° C. to about 22° C., preferably at about 0° C. under a dry inert atmosphere, e.g. argon and adding a transition metal source, e.g. tetrakis(triphenylphosphine)-palladium or palladium acetate/triphenyl phosphine. An organometallic of formula $Ar^{10}$-X[m]$_m$-Met, wherein in $Ar^{10}$, X and m are as defined above and Met is, for example, ZnCl or $B(OH)_2$, is added to the reaction mixture at about −20° C. to about 22° C., preferably at about 0° C., the reaction mixture is stirred for about 15 min to 4 h, preferably about 1 h, and is then allowed to warm to about 22° C. Addition of dilute acid, e.g. 1N HCl, followed by extraction with a suitable organic solvent, e.g. ethyl acetate (EtOAc), produces compound XX.

The ketone of-formula XX is dissolved in a suitable *solvent* e.g. $CH_3OH$ a hydrogenation catalyst is added, e.g. Pd on carbon, and the mixture is exposed to $H_2$ gas under a pressure of about 14 psi to 100 psi, preferably about 60 psi for about 1 to 24 h, preferably, about 16 h. The hydrogenation catalyst is removed by filtration and the solvent is removed in vacuo to produce a compound Ij as a mixture of alcohol diastereomers which can be separated by conventional means.

Alternatively, a ketone of formula XX is dissolved in a suitable solvent, e.g. THF, about −40° C. to about 22° C., preferably at about 0° C., and a suitable reducing agent such as $NaBH_4$, a substituted borohydride (e.g., [cbz-proline]$_3$ BHNa) or a borane is added, optionally in the presence of a suitable chiral promotor present either in catalytic or stoichiometric amounts, e.g., chiral borane of structures:

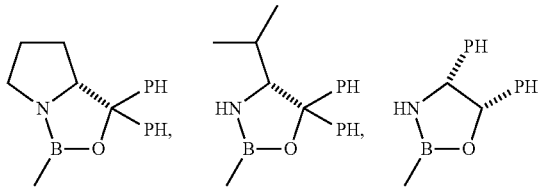

Addition of dilute acid, e.g., 1N HCl, followed by extraction with a suitable solvent produces compounds of formula Ij. As above, protecting groups at $Ar^{10}$, $Ar^{20}$, $Ar^{30}$ and $R^{2'}$ are removed as necessary. When either a chiral reagent or a chiral promotor is used, the resulting product is non-racemic.

Compounds of formula XIX can be prepared by a multistep procedure as represented below:

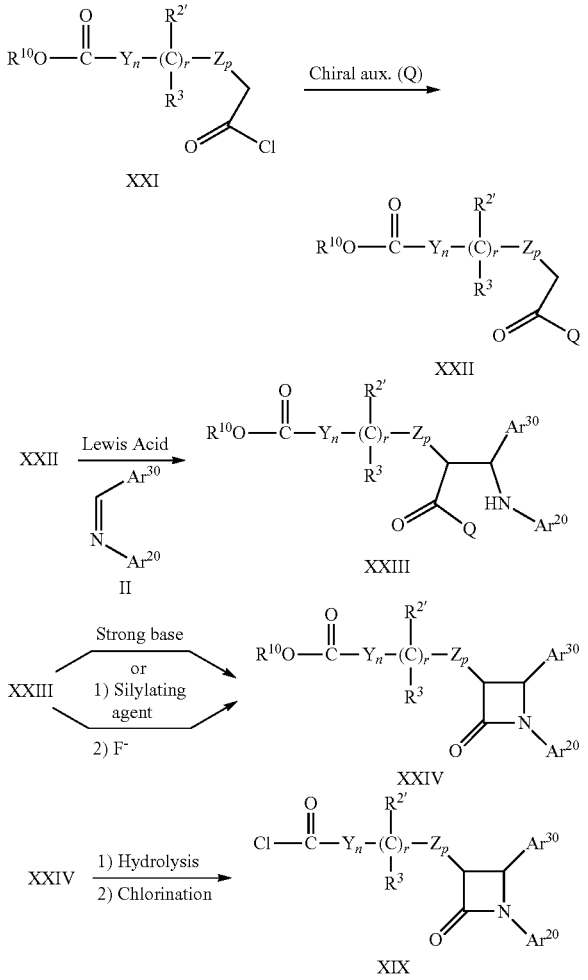

Compounds of formula XXI, wherein $R^{10}$ is lower alkyl and the remaining *variables are as defined above, are commercially available or can be prepared by treating the corresponding carboxylic acid (i.e., compounds wherein the Cl is replaced by a hydroxy group) with a chlorinating agent, e.g. $SOCl_2$ or oxalyl chloride, under a dry atmosphere, neat or in a suitable inert organic solvent, e.g. toluene at about 40° C. to 110° C., preferably about 70° C.; alternatively, a catalyst made be added, e.g. dimethylformamide (DMF), the reaction is conducted at about 22° C., and the solvent and excess reagents are removed in vacuo. The compound XXI is reacted with a chiral auxiliary such as (S)-4-phenyl-2-oxazolidinone according to the following procedure; a chiral auxiliary is treated with a strong base such as an alkyllithium, a metal hydride or a tertiary amine base such as triethylamine, in a suitable anhydrous organic solvent, e.g., dry THF, under a dry, inert atmosphere, e.g. argon at about −85° C., to 22° C., preferably about 0° C., for about 10 min to 60 min, preferably about 30 minutes. The resulting anion is reacted, without isolation, with compound XXI in a suitable anhydrous organic solvent, e.g. dry THF, under a dry, inert atmosphere, e.g. argon at about −85° C. to about 22° C., preferably 0° C., for about 30 min to 60 min, preferably 30 min. The reaction is warmed to about 220° C. and continued for 1 to 12 h, preferably 6 h. Water is added and compound XXII is isolated by extraction and purified by crystallization.*

*The compound of formula XXII is treated in the same manner as described in step 1 of Method E to obtain a compound XXIII.*

Azetidinone ring closure can be accomplished by alternative procedures. By one method, a compound of formula XXIII is treated with a strong non-nucleophilic base, such as sodium or lithium-bistrimethylsilylamide, in a suitable inert organic solvent, e.g. $CH_2Cl_2$, at about −78° C. to about 10° C., preferably about 0° C. The mixture is stirred for about 1 to 2 hours while gradually warming to about 22° C. Compound XXIV is isolated by conventional extraction with $CH_2Cl_2$. In another, two-step method, a compound of formula XXIII is first treated with mild silylating agent, e.g. N,O-bis(trimethylsilyl)acetamide at about 0° C. to about 100° C., preferably about 40° C. for about 10 min to 60 min, preferably 30 min, then treated with a fluoride anion source, e.g., tetrabutylammonium fluoride (TBAF), at about 0° C. to about 100° C., preferably 40° C., and allowed to stir for about 0.5 to about 4 hours, preferably about 2 hours. Compound XXIV is isolated by conventional extraction methods.

The compounds of formula XXIV is hydrolysed by a suitable base, e.g. LiOH, in a suitable solvent, e.g. 66% $CH_3OH$/water at about 0° C. to about 50° C., preferably 22° C., for about 1 to 4 hours, preferably 2 hours, then extracted with a suitable solvent, e.g. EtOAc. The resulting acid is converted to the acid chloride as described above by treatment with a chlorination agent, e.g. oxalyl chloride, to afford compound

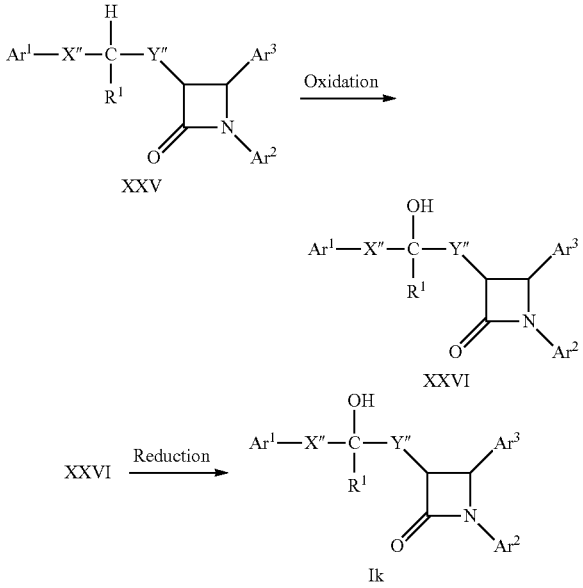

Compounds of formula Ik, wherein $Ar^1$, $Ar^2$, $Ar^3$ and $R^1$ are as defined above, one of X" and Y" is —$CH_2CH_2$— and the other is selected from the group consisting of —$CH_2CH_2$—, —$CH_2$—, —CH(lower alkyl)-, —CH(dilower alkyl) and a bond, are prepared by oxidation of an alkene of formula XXV, wherein one of X' and Y' is —CH═CH— and the other is —CH═CH—, —$CH_2$—, —$CH_2CH_2$—, —CH(lower alkyl)-, —CH(dilower alkyl) or a bond, and the remaining variables are as defined above, can be prepared by the following two step procedure.

A compound of formula XXV, which can be prepared by Method D, above, is treated with an oxidizing agent such as $SeO_2$, phenylselenic anhydride or $CrO_3$ in a suitable solvent such as dioxane at about 22° to 100° C. for about 0.5 to 12 hours. After the starting material is consumed as determined by TLC, or 12 hours, the reaction is cooled to about 22° C. and the product XXVI is isolated by extraction.

In the second step, an allylic alcohol of formula XXVI is dissolved in a suitable solvent, e.g., EtOAc, a hydrogenation catalyst added, e.g., Pd on carbon, and the mixture is exposed to $H_2$ gas under a pressure of about 14 psi to 60 psi for about 1 to 12 hours. The hydrogenation catalyst is removed in vacuo to obtain a compound of formula Ik.

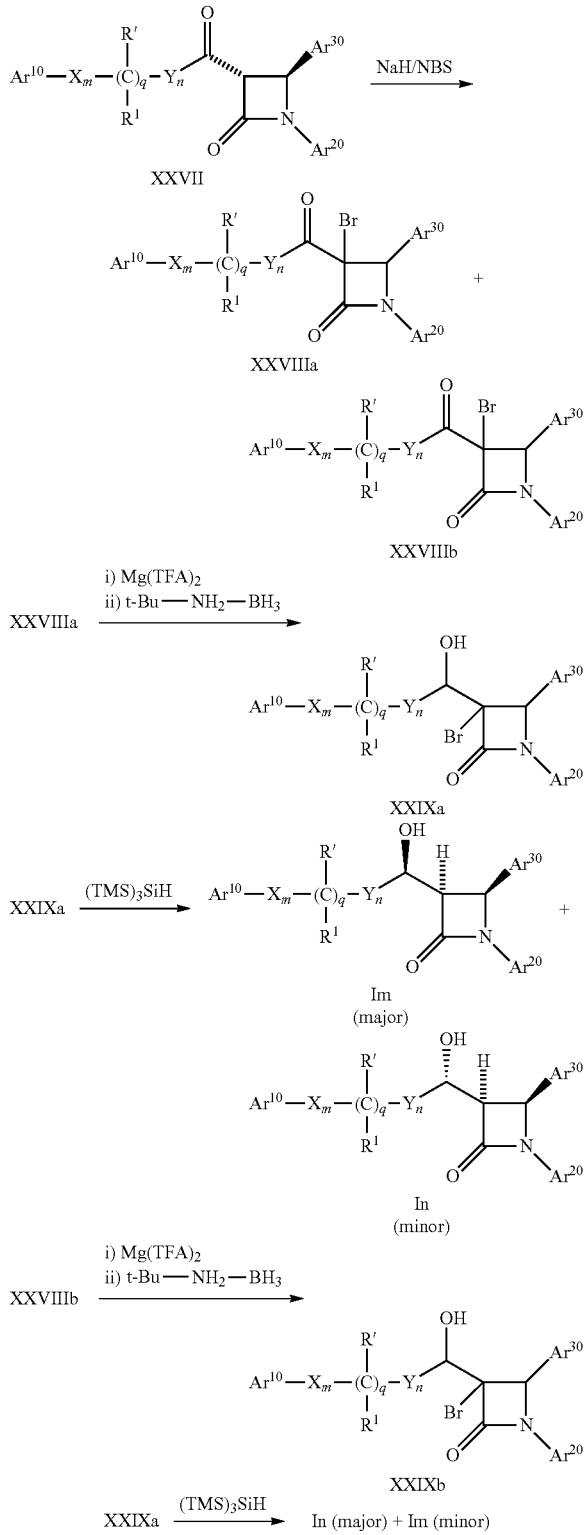

Alcohols of formula Im and In (i.e., compounds of formula I where r is 1, $R^2$ is —OH, $R^3$ is hydrogen and p is 0) can be selectively obtained front ketones of formula XXVII in three steps comprising bromination, reduction and debromination. Since the stereochemistry of the major isomers of alcohols XXIXa and XXIXb are different, one can selectively prepare either diastereomeric alcohol.

In the above process, a ketone of formula XXVII, which can be prepared by oxidation of the corresponding hydroxy compound by well known methods, is halogenated, for example by treatment in an inert solvent, e.g., THF, with NaH followed by N-bromosuccinimide, to obtain a mixture of 3-bromo-ketone compounds XXVIII (a and b). Compounds [15] XXVIIIa and XXVIIIb are then separately reduced to the corresponding alcohols, for example by treatment with magnesium trifluoroacetate ($Mg(TFA)_2$) and t-butylamine borane (t-Bu—$NH_2$—$BH_3$) in an inert solvent such as THF at a temperature of about −78° C. to 0° C. The resultant alcohols XXIX are dehalogenated by treatment with tris(trimethylsilyl)silane ($(TMS)_3SiH$) in a solvent such as toluene in the presence of a radical initiator such as 2,2'-azobisisobutyronitrile (AIBN) to obtain a mixture of isomers Im and In which can be separated into individual enantiomers by conventional means, e.g., HPLC. Again, protecting groups at $Ar^{10}$, $Ar^{20}$, $Ar^{30}$ and R' are removed as necessary.

Starting compounds III, V, VI, VII, VIII, XIV, XVII, XXI and XXV are all either commercially available or well known in the art and can be prepared via known methods.

Reactive groups not involved in the above processes can be protected during the reactions with conventional protecting groups which can be removed by standard procedures after the reaction. The following Table 1 shows some typical protecting groups:

TABLE I

| Group to be Protected | Group to be Protected and Protecting Group |
|---|---|
| —COOH | —COOalkyl, —COObenzyl, —COOphenyl |
| >NH | >NCOalkyl, >NCObenzyl, >NCOphenyl |
| | >$NCH_2OCH_2CH_2Si(CH_3)_3$, >$NC(O)OC(CH_3)_3$, |
| | >N-benzyl, >$NSi(CH_3)_3$, >N—Si($CH_3$)($CH_3$)—$C(CH_3)_3$ |
| —$NH_2$ | 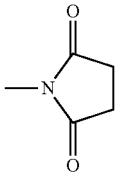 |
| —OH | —$OCH_3$, —$OCH_2OCH_3$, —O—Si($CH_3$)($CH_3$)—$C(CH)_3$ |
| | —$OSi(CH_3)_3$, or —$OCH_2$phenyl |

We have found that the compounds of this invention lower serum lipid levels, in particular serum cholesterol levels. Compounds of this invention have been found to inhibit the intestinal absorption of cholesterol and to significantly reduce the formation of liver cholesteryl esters in animal models. Thus, compounds of this invention are hypocholesterolemic agents by virtue of their ability to inhibit the intestinal absorption and/or esterification of cholesterol; they are, therefore, useful in the treatment and prevention of atherosclerosis in mammals, in particular in humans.

The in vivo activity of the compounds of formula I can be determined by the following procedure:

In Vivo Assay of [Hypoligidemic] *Hypolipidemic* Agents Using the Hyperlipidemic Hamster Hamsters are separated into groups of six and given a controlled cholesterol diet (Purina Chow #5001 containing 0.5% cholesterol) for seven days. Diet consumption is monitored to determine dietary cholesterol exposure in the face of test compounds. The animals are dosed with the test compound once daily beginning with the initiation of diet. Dosing is by oral gavage of 0.2 mL of corn oil alone (control group) or solution (or suspension) of test compound in corn oil. All animals moribund or in poor physical condition are euthanized. After seven days, the animals are anesthetized by intramuscular (IM) injection of ketamine and sacrificed by decapitation. Blood is collected into vacutainer tubes containing EDTA for plasma lipid analysis and the liver excised for tissue lipid analysis. Lipid analysis is conducted as per published procedures (Schnitzer-Polokoff, R., et al. Comp. Biochem. Physiol., 99A, 4 (1991), p. 665-670) and data is reported as percent reduction of lipid versus control.

The present invention also relates to a pharmaceutical composition comprising a compound of formula I and a pharmaceutically acceptable carrier. The compounds of formula I can be administered in any conventional dosage form, preferably an oral dosage form such as a capsule, tablet, powder, cachet, suspension or solution. The formulations and pharmaceutical compositions can be prepared using conventional pharmaceutically acceptable excipients and additives and conventional techniques. Such pharmaceutically acceptable excipients and additives include non-toxic compatible fillers, binders, disintegrants, buffers, preservatives, anti-oxidants, lubricants, flavorings, thickeners, coloring agents, emulsifiers and the like.

The daily hypocholesteremic dose of a compound of formula I is about 0.1 to about 30 mg/kg of body weight per day, preferably about 0.1 to about 15 mg/kg. For an average body weight of 70 kg, the dosage level is therefore from about 5 mg to about 1000 mg of drug per day, given in a single dose of 2-4 divided doses. The exact dose, however, is determined by the attending clinician and is dependent on the potency of the compound administered, the age, weight, condition and response of the patient.

For the combinations of this invention wherein the hydroxy substituted azetidinone is administered in combination with a cholesterol biosynthesis inhibitor, the typical daily dose of the cholesterol biosynthesis inhibitor is 0.1 to 80 mg/kg of mammalian weight per day administered in single or divided dosages, usually once or twice a day; for example, for HMG CoA reductase inhibitors, about 10 to about 40 mg per dose is given 1 to 2 times a day, giving a total daily dose of about 10 to 80 mg per day, and for the other cholesterol biosynthesis inhibitors, about 1 to 1000 mg per dose is given 1 to 2 times a day, giving a total daily dose of about 1 mg to about 200 mg per day. The exact dose of any component of the combination to be administered is determined by the attending clinician and is dependent on the potency of the compound administered, the age, weight, condition and response of the patient.

Where the components of a combination are administered separately, the number of doses of each component given per day may not necessarily be the same, e.g. where one component may have a greater duration of activity, and will therefore need to be administered less frequently.

Since the present invention relates to the reduction of plasma cholesterol levels by treatment with a combination of active ingredients wherein said active ingredients may be administered separately, the invention also relates to combining separate pharmaceutical compositions in kit form. That is, a kit is contemplated wherein two separate units are combined: a cholesterol biosynthesis inhibitor pharmaceutical composition and a hydroxy substituted azetidinone cholesterol absorption inhibitor pharmaceutical composition. The kit will preferably include directions for the administration of the separate components. The kit form is particularly advantageous when the separate components must be administered in different dosage forms (e.g. oral and parenteral) or are administered at different dosage intervals.

Following are examples of preparing compounds of formula I. The stereochemistry listed is relative stereochemistry unless otherwise noted. The terms cis and trans refer to the relative orientations at the azetidinone 3- and 4-positions unless otherwise indicated. The term "J" refers to the proton NMR coupling constant in hertz (Hz) between the 3- and 4-substituted protons of the azetidinone. All NMR data is of $CDCl_3$ solution unless otherwise indicated.

A

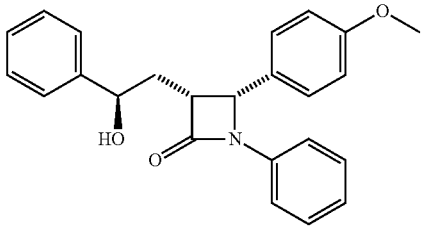

and

B

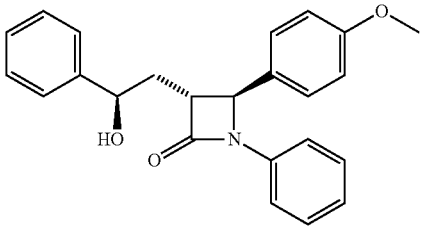

Freshly prepare a solution of lithium diisopropylamide (LDA) by dissolving diisopropylamine (1.19 g, 11.8 mmol) in anhydrous THF (20 ml) at −78° C. under argon. Add n-butyllithium (4.9 ml, 11.8 mmol, 2.4M in hexanes) and stir for 0.5 h at −78° C. To this cold solution add, 4phenylbutyrolactone (1.75 g, 10.8 mmol) in THF (4 ml) over 0.25 h, keeping the reaction temperature below −65° C. Stir at −78° C. for 0.25 h, then add 4-methoxybenzylidine anisidine (2.33 g, 11.0 mmol) in THF (8 ml) over 1 h at −78° C. Warm the reaction slowly to −50° C. over 1 h. Quench the reaction at low temperature with 1N HCl (12 ml). Partition the reaction mixture between ether and 1N HCl, wash the ether layer with water, combine the ether extracts, dry over $MgSO_4$ and concentrate in vacuo. Crystallize the crude reaction residue (3.0 g) from EtOAc-ether to obtain 1.54 g of compound A. Reconcentrate the filtrate and chromatograph on silica gel 60, eluting with 4:1 EtOAc-hexane, and isolate additional compound A (0.385 g) as well as compound B (0.420 g).

Compound A: mp 218°-220° C.; IR 1730 cm-1; CI (M−H) 374; J=5.9 Hz.

Compound B: mp 74°-76° C.; IR 1730 cm-1; CI (M+H) 374; J=2.3 Hz.

Using a similar procedure and appropriate starting materials, prepare compound 1C:

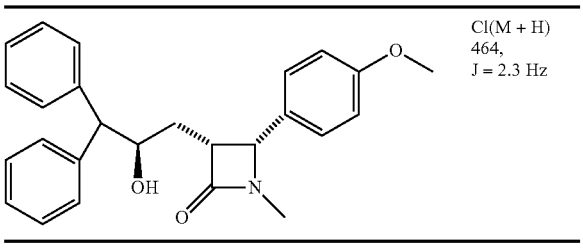

EXAMPLE 2

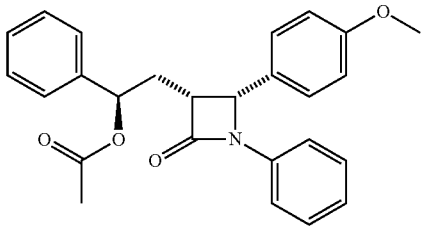

To a solution of compound A from Example 1 (0.5 g, 1.3 mmol) in anhydrous pyridine (2.7 ml), add acetic anhydride (0.63 ml, 6.7 mmol). Stir for 16 h, dilute with $CH_2Cl_2$ and wash 3× with 1N HCl 1× with NaCl (sat'd) and 1× with water. Concentrate the organic layer to dryness and crystallize the residue from EtOAc to obtain the title compound (0.46 g), mp 167°-169° C.; IR 1745 cm-1; EI (M+) 415; J=5.9 Hz.

EXAMPLE 3

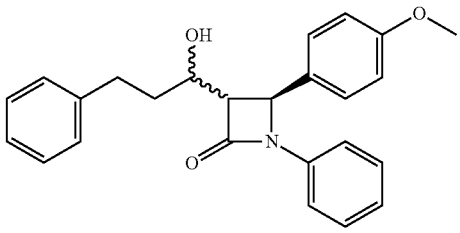

Freshly prepare a solution of lithium isopropylcyclohexylamide (LICA) by adding n-butyllithium (2.84 mL of a 1.6M solution) to 5 a solution of isopropylcyclohexylamine (0.75 mL) in THF (100 mL) at −78° C. Dissolve N-phenyl-4-(4-methoxyphenyl)-2-azetidinone (1.0 g) in THF (8 mL) and slowly add to the LICA solution at −78° C. After stirring for 20 min, add hydrocinnamaldehyde (0.54 g) and stir the reaction mixture at −78° C. for 4 h. Quench the reaction with 10% $KHSO_4$ and extract the product with EtOAc. Separate the organic layer, wash with water and NaCl (sat'd). Concentrate the extract and purify the resultant residue on a silica gel 60 column, eluting with EtOAc:hexane (15:85) to obtain 1.15 g of product as a mixture of diastereomers. Separate the diastereomers by HPLC on a silica gel column to give three diastereomers 3A, 3B and 3C:

| | | |
|---|---|---|
| 3A | 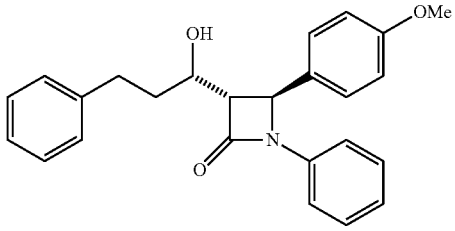 | 1H in $CDCl_3$: 7.32-7.18(m, 11H); 708-6.99 (m, 1H); 6.89(d, J = 9 Hz, 2H); 4.80(d, J = 2.4 Hz, 1H); 4.10-4.00(m, 1H); 3.79(s. 3H); 3.20-3.16(m, 1H); 2.90-2.67(m, 2H); 2.15-1.85(m, 3H) |
| 3B | 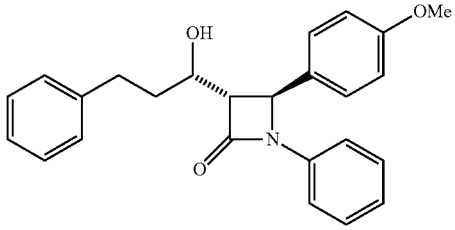 | 1H in $CDCl_3$: 7.35-7.10(m, 11H); 7,08-6.99 (m, 1H); 6.89(d, J = 9 Hz, 2H); 5.09(d, J = 2.4 Hz, 1H); 4.26-4.14(m, 1H); 3.79(s, 3H); 3.21-3.14(m, 1H); 2.89-2.57(m, 2H); 2.40-1.85(m, 3H) |
| 3C | 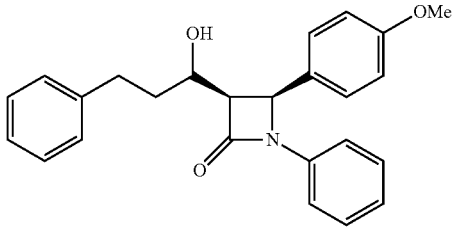 | 1H in $CDCl_3$: 7.30-7.00(m, 10H); 6.99 (d, J = 8 Hz, 2H); 6.83(d, J = 9 Hz, 2H); 5.12(d, J = 5.5 Hz, 1H); 3.82(s, 3H); 3.75-3.63(m, 1H); 3.52(dd, J = 9.5 Hz, 1H); 2.71-2.57(m, 1H); 2.49-2.33(m, 1H); 1.68-1.50(m, 1H); 1.47-1.31)m, 1H) |
The 3A, 3B and 3C, diastereomers were further separated according to the following reaction scheme, wherein partial structures are shown:
-continued
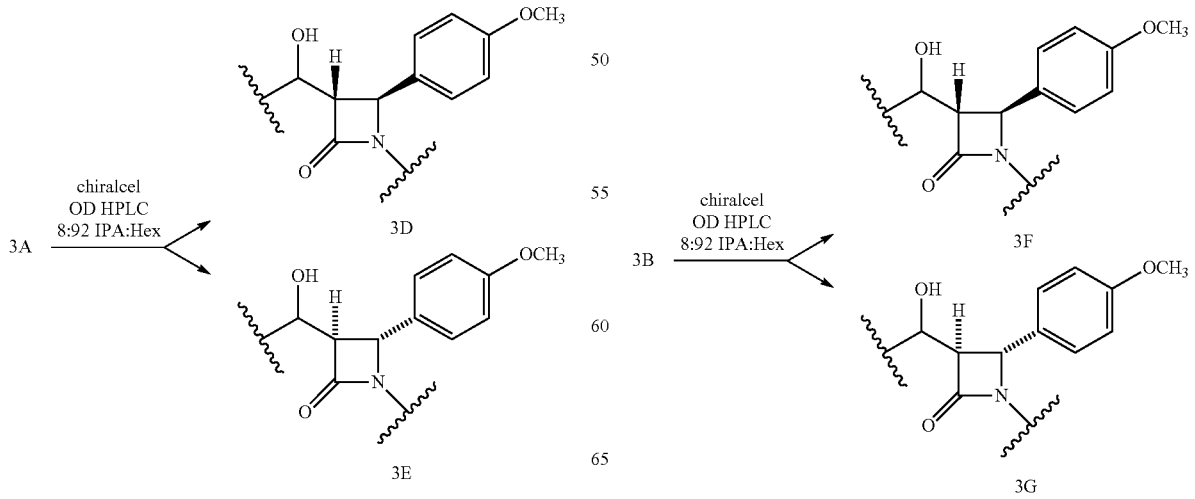

-continued

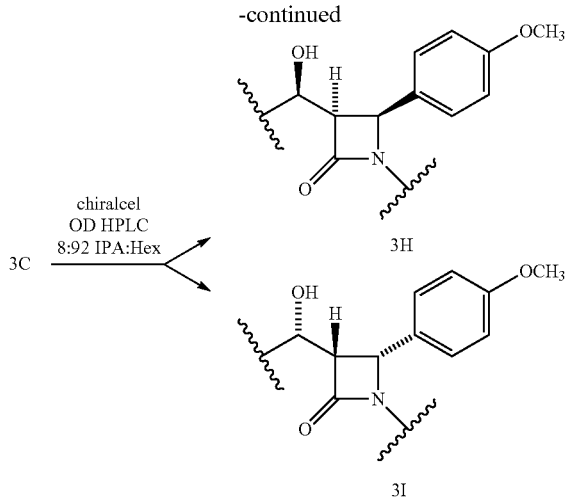

(The following CD spectra data [θ] are all obtained in $CH_3OH$.)

3D) $[\theta]_{227nM}$=+2.0×10$^4$ cm$^2$/dM; $[\theta]_{241nM}$=−4.6×10$^4$ cm$^2$/dM. Elemental analysis calc for $C_{25}H_{25}NO_3$−0.25 $H_2O$: C 76.6; H 6.56 N 3.57. found: C 76.66; H 6.49; N 3.64.

3E) $[\theta]_{227nM}$=−1.95×10$^4$ cm$^2$/dM; $[\theta]_{241nM}$=+4.45×10$^4$ cm$^2$/dM. Elemental analysis calc for $C_{25}H_{25}NO_3$.0.5 $H_2O$: C 75.73; H 6.61; N 3.53. found: C 75.66; H 6.41; N 3.60.

3F) $[\theta]_{226nM}$=+1.97×10$^4$ cm$^2$/dM; $[\theta]_{240nM}$=−5.22×10$^4$ cm$^2$/dM. Elemental analysis calc for $C_{25}H_{25}NO_3$: C 77.48; H 6.5-1; N 3.62. found: C 77.44; H 6.53; N 3.70.

3G) $[\theta]_{226nM}$=−1.78×10$^4$ cm$^2$/dM; $[\theta]_{241nM}$=+4.78×10$^4$ cm$^2$/dM (CIMS 388 M$^+$H).

3H) $[\theta]_{226nM}$=+2.24×10$^4$ cm$^2$/dM; $[\theta]_{241nM}$=−5.4×10$^4$ cm$^2$/dM. $[\alpha]_D^{25}$=−54.4° (2.5 mg/ml $CH_3OH$) Elemental analysis calc for $C_{25}H_{25}NO_3$: C 77.48; H 6.51; N 3.62. found: C 77.11; H 6.50; N 3.72.

3I) $[\theta]_{226nM}$=−2.05×10$^4$ cm$^2$/dM; $[\theta]_{241nM}$=+5.2×10$^4$ cm$^2$/dM. (CIMS 388 M$^+$H).

3J)

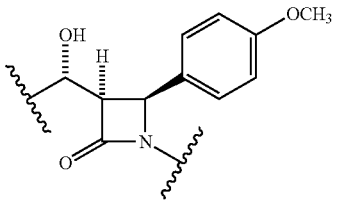

Add DEAD (0.11 ml) to a solution of compound 3H (132 mg), $PPh_3$ (0.18 g) and $HCO_2H$ (39 ml) in THF (5 ml). Stir at room [temperatq] *temperature* overnight, then partition the reaction mixture between $Et_2O$ and $H_2O$. Wash (brine) and dry ($MgSO_4$) the organic layer and concentrate to dryness. Flash chromatograph the residue using EtOAc:Hex (1:4) to obtain the formate ester. Dissolve this in $CH_3OH$ and add 4 drops of conc. HCl. After 4 h, concentrate in vacuo and flash chromatograph the residue using EtOAc:Hex (1:3) to obtain 3J. $[\theta]_{224nM}$=+2.54×10$^3$ cm$^2$/dM;

$[\theta]_{239nM}$=+5.70×10$^4$ cm$^2$/dM; $[\alpha]_D^{20}$=−157.6° (2.5 mg/ml $CH_3OH$)

3K)

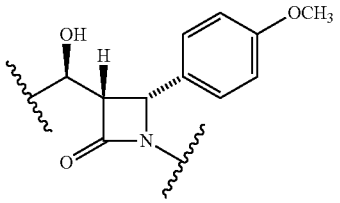

Using the procedure described for 3J, treat compound 3I to obtain 3K. $[\theta]_{222nM}$=−3.4×10$^3$ cm$^2$/dM; $[\alpha]_{240nM}$=−5.6×10$^4$ cm$^2$/dM. $[\alpha]_D^{20}$=+167.2° (2.5 mg/ml $CH_3OH$)

Using the procedure described above for preparing compounds 3A and 3B, treat N-phenyl-4-(4-methoxyphenyl)-2-azetidinone with LICA followed by 2-naphthaldehyde to obtain the diastereomers 3L and 3M:

3L

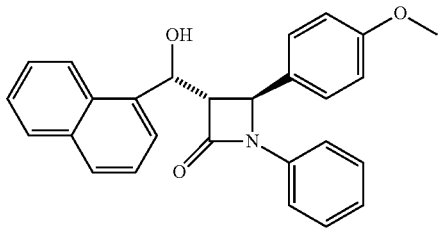

mp 137-138° C.

3M

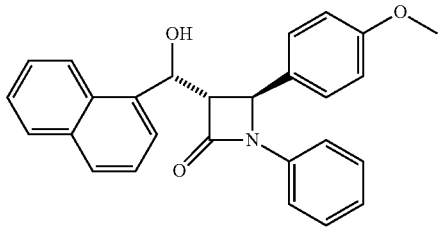

mp 150-151° C.

EXAMPLE 4

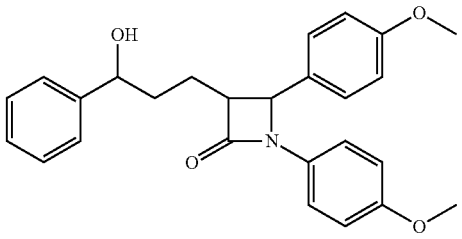

Method 1:

Step 1) To a refluxing solution of of 4-methoxyberizylidene anisidine (10.0 g, 41.5 mmol) and tributylamine (20.8 ml. 87 mmol) in toluene (100 ml), add 5-bromovaleroyl chloride (8.5 g, 43, mmol) in toluene (20 ml) dropwise over 2 h. Stir the reaction mixture at 80° C. for 12 h, cool to room temperature, wash 3× with 1 N HCl, 1× with water and dry the organic layer over $MgSO_4$. Purify by silica gel chromatography, eluting with ethyl acetate:hexane (4:1) to obtain 5.1 g of (3R, 4S)-1,4-bis(4-methoxyphenyl)-3-(3-bromoproyl)-2-azetidinone (relative stereochemistry), mp 70°-73° C., E1 (M$^+$) 404; J=2.3 Hz.

Step 2) To a solution of the product of step 1 (5.1 g, 12.6 mmol) in $(CH_3)_2SO$ (20 ml), add $(CH_3)_3N(O)$ (2.39 g, 31.9 mmol). Heat the mixture at 60° C. for 3 h, cool to room temperature, dilute with EtOAc, and wash 3× with water. Combine the aqueous fractions and extract with EtOAc. Combine the organic fractions and concentrate. Purify the crude product by silica gel chromatography, eluting with EtOAc:hexane (1:1) to obtain 1.4 g (3R, 4S)-1,4-bis-(4-methoxyphenyl)-2-oxo-3-azetidine-propanol (relative stereochemistry), an oil; EI ($M^+$) 339; J=2.3 Hz.

Step 3) To a solution of the product of step 2 ([0.7134]*0.734* g, 2.2 mmol) in THF (4 ml) at 0° C., add phenylmagnesium bromide (2.4 ml, 2.4 mmol, 1.0 M in THF) over 0.25 h. After 1 h at 0° C., add water (5 ml), separate the layers, wash the organic layer 1 × with 1N HCl, dry with $MgSO_4$ and concentrate to an oil. Purify by silica gel chromatography, eluting with EtOAc:hexane (2:1) to obtain 0.372 g of the title compound (mix of diastereomers) as an oil. CI ($M^+H$) 418.

Separation of diastereomers: Apply the diastereomeric mixture from step 3 to a Chiralcel OD (Chiral Technologies Corp, Pa.) chromatography column, eluting with hexane: ethanol (9:1) to obtain enantiomerically pure (>98%) diastereomers as follows:

4A

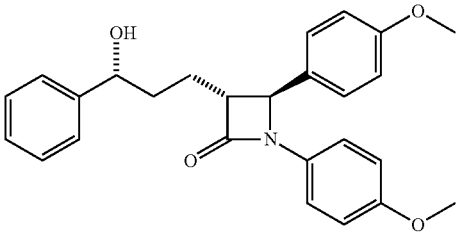

Oil:$[\alpha]_D^{22}$ = +8.3°, conc. = 3 mg/ml in MeOH; Cl(M + H)418J = 2.1 Hz.

4B

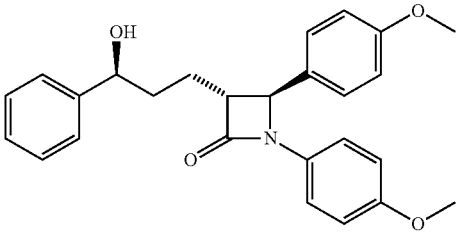

Oil:$[\alpha]_D^{22}$ = +33.1°, conc. = 3 mg/ml in MeOH; Cl(M + H)418J = 2.1 Hz.

4C

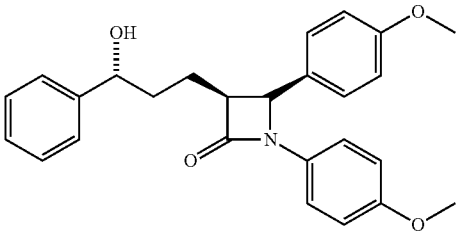

Oil:$[\alpha]_D^{22}$ = -8.0°, conc. = 3 mg/ml in MeOH; Cl(M + H)418J = 2.1 Hz.

-continued

4D

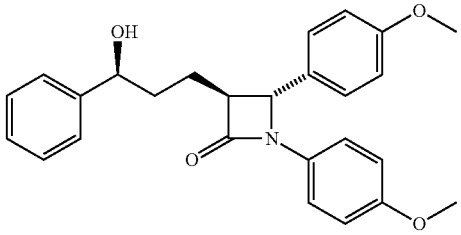

Oil:$[\alpha]_D^{22}$ = -29.5°, conc. = 3 mg/ml in MeOH; Cl(M + H)418J = 2.1 Hz.

Method 2:

Step 1) To a solution of 1,4-(S)-bis(4-methoxyphenyl)-3-(3(R)-phenylpropyl)-2-azetidinone (5.04 g, 0.013 mole) in $CCl_4$ (20 ml) at 80° C., add NBS (2.76 g, 0.0155 mole) and benzoyl peroxide (0.24 g, 1.0 mmole) in three equal portions over 1 h. Follow the reaction by TLC (4:1 hexane:EtOAc). Cool the reaction to 22° C., add $NaHSO_4$, separate the layers and wash the organic layer 3× with water. Concentrate the organic layer to obtain the crude product.

CI ($M^+H$) 480; $^1H$ in $CDCl_3$ δ PhC<u>H</u>(OH)=5.05 ppm.

Step 2) Dissolve the crude product of Step 1 in $CH_2Cl_2$ (30 ml) and add 40% n-BuNOC(O)$CF_3$ in water (30 ml). Reflux the biphasic reaction for 24 h, cool, separate the layers and wash the organic layer 6× with water. Concentrate the organic layer to dryness and immediately redissolve the residue in ethanol saturated with $NH_3$ (10 ml). After 1 h, concentrate the reaction mixture and partially purify by silica gel chromatography. Further purify by HPLC to obtain a 1:1 mixture of compounds 4A and 4B. The mixture can be further purified on a Chiracel OD column to obtain 4A and 4B separately as characterized above.

Using the procedure described in Example 4, Method 2, with 4(S)-(4-acetoxyphenyl)-3(R)-(3-phenylpropyl)-1 -(4-methoxy-phenyl)-2-azetidinone as the starting material, prepare the following compounds:

4E

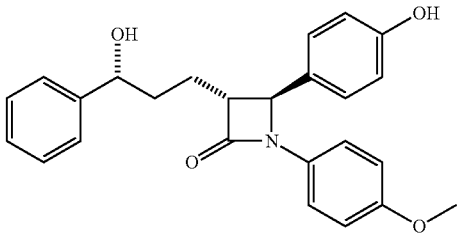

mp 87-90° C.
HRMS calc'd for $C_{25}H_{25}NO_4$ = 403.1797, found 403.1785;
$^1H$ in $CDCl_3$ δPhCH(OH) = 4.82 ppm.

-continued

4F

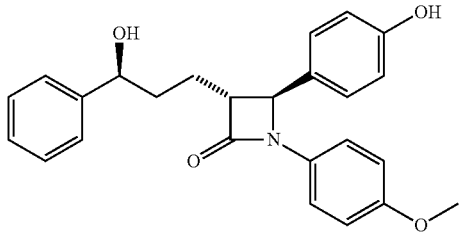

HRMS calc'd for $C_{25}H_{25}NO_4$ = [403.1787, found 403.1785]; 403.1797, found 403.1787; $^1H$ in $CDCl_3$ δPhCH(OH) = 4.78

EXAMPLE 5

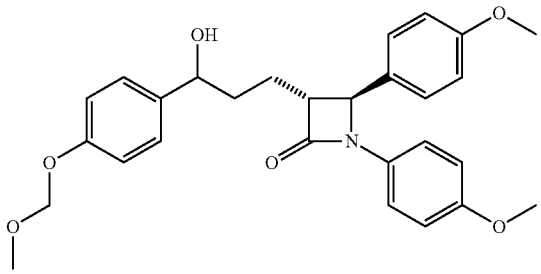

To a solution of the product of step 2 of Example 4 (0.230 g, 0.68 mmol) in THF (2 ml), add the reagent derived from treatment of 4-methoxymethylphenyl bromide (0.159 g, 0.736 mmol) in THF (4 ml) at −78° C. with sec-butyllithium (0.6 ml, 0.78 mol, 1.3M in hexanes), followed by $CeCl_3$ (0.186 g, (0.75 mmol). After 4 h, extract the product and purify by chromatography in a manner similar to that described in step 3 of Example 4 to obtain 0.05 g of the title compound (mix of diastereomers) as an oil. CI ($M^+H$) 478.

EXAMPLE 6

6A

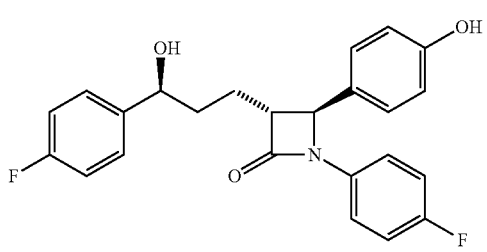

and

6B

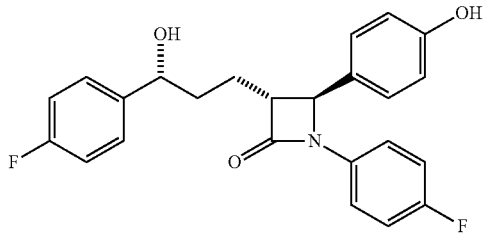

Step 1): To a solution of (S)-4-phenyl-2-oxazolidinone (41 g, 0.25 mol) in $CH_2Cl_2$ (20 ml), add 4-dimethylaminopyridine (2.5 g, 0.02 mol) and triethylamine (84.7 ml, 0.61 mol) and cool the reaction to 0° C. Add methyl-4-(chloroformyl) butyrate (50 [9] g, 0.3 mol) as a solution in $CH_2Cl_2$ (375 ml) dropwise over 1 h, and allow the reaction to warm to 22° C. After 17 h, add water and $H_2SO_4$ (2N, 100 ml), separate the layers, and wash the organic layer sequentially with NaOH (10%). NaCI (sat'd) and water. Dry the organic layer over $MgSO_4$ and concentrate to obtain a semicrystalline product.

Step 2): To a solution of $TiCl_4$ (18.2 ml, 0.165 mol) in $CH_2Cl_2$ (600 ml) at 0° C., add titanium isopropoxide (16.5 ml, 0.055 mol). After 15 min, add the product of Step 1 (49.0 9, 0.17 mol) as a solution in $CH_2Cl_2$ (100 ml). After 5 min., add diisopropylethylamine (DIPEA) (65.2 ml, 0.37 mol) and stir at 0° C. for 1 h, cool the reaction mixture to −20° C., and add 4-benzyloxybenzylidine(4-fluoro)aniline (114.3 g, 0.37 mol) as a solid. Stir the reaction vigorously for 4 h at −20° C., add acetic acid as a solution in $CH_2Cl_2$ dropwise over 15 min, allow the reaction to [warnr] *warm* to 0° C., and add $H_2SO_4$ (2N). Stir the reaction an additional 1 h, separate the layers, wash with water, separate and dry the organic layer. Crystallize the crude product from ethanol/water to obtain the pure intermediate.

Step 3): To a solution of the product of Step 2 (8.9 g, 14.9 mmol) in toluene (100 ml) at 50° C., add N,O-bis(trimethylsilyl)acetamide (BSA) (7.50 ml, 30.3 mmol). After 0.5 h, add solid TBAF (0.39 g, 1.5 mmol) and stir the reaction at 50° C. for an additional 3 h. Cool the reaction mixture to 22° C., add $CH_3OH$ (10 ml), wash the reaction mixture with HCl (1N), $NaHCO_3$ (1N) and NaCl (sat'd), and dry the organic layer over $MgSO_4$.

Step 4): To a solution of the product of Step 3 (0.94 g, 2.2 mmol) and $CH_3OH$ (3 ml), add water (1 ml) and $LiOH.H_2O$ (102 gm, 2.4 mmole). Stir the reaction at 22° C. for 1 h and add additional $LiOH.H_2O$ (54 mg, 1.3 mmole). After a total of 2 h, add HCl (1N) and EtOAc, separate the layers, dry the organic layer and concentrate in vacuo. To a solution of resultant product (0.91 g, 2.2 mmol) in $CH_2Cl_2$ at 22° C., add ClCOCOCl (0.29 ml, 3.3 mmol) and stir for 16 h. Remove the solvent in vacuo.

Step 5): To an efficiently stirred suspension of 4-fluorophenylzinc chloride (4.4 mmol) prepared from 4-fluorophenylmagnesium bromide 5 (1M in THF, 4.4 ml, 4.4 mmol) and $ZnCl_2$ (0.6 g, 4.4 mmol) at 4° C., add tetrakis(triphenylphosphine)palladium (0.25 g, 0.21 mmol) and the product of Step 4 (0.94 g, 2.2 mmol) as a solution in THF (2 ml). Stir the reaction for 1 h at 0° C. and then for 0.5 h at 22° C. Add HCl (1N, 5 ml) and extract with EtOAc. Concentrate the organic layer to an oil and purify by silica gel chromatography to obtain 1-(4-fluorophenyl)-4(S)-(4-hydroxyphenyl)-3(R)-(3-oxo-3-phenylpropyl)-2-azetidinone:

HRMS calc'd for $C_{24}H_{19}F_2NO_3$=408.1429, found 408.1411.

Step 6): To the product of Step 5 (0.95 g, 1.91 mmol) in THF (3 ml), add (R)-tetrahydro-1-methyl-3,3-diphenyl-1H, 3H-pyrrolo-[1,2-c][1,3,2]oxazaborole (120 mg, 0.43 mmol) and cool the mixture to −20° C. After 5 min, add borohydride-dimethylsulfide complex (2M in THF: 0.85 ml, 1.7 mmol) dropwise over 0.5 h. After a total of 1.5 h, add $CH_3OH$ followed by HCl (1 N) and extract the reaction mixture with EtOAc to obtain 1-(4-fluorophenyl)-3(R)-[3(S)-(4-fluorophenyl)-3-hydroxypropyl)]-4(S)-[4-(phenylmethoxy)phenyl]-2-azetidinone (compound 6A-1) as an oil. $^1H$ in $CDCl_3$ δ H3=4.68, J=2.3 Hz. CI ($M^+H$) 500.

Use of (S)-tetra-hydro-1-methyl-3,3-diphenyl-1H,3H-pyrrolo-[1,2-c][1,3,2] oxazaborole gives the corresponding 3(R)-hydroxypropyl azetidinone (compound 6B-1). $^1H$ in $CDCl_3$ δ H3=4.69, J=2.3 Hz. CI ($M^+H$) 500.

To a solution of compound 6A-1 (0.4 g, 0.8 mmol) in ethanol (2 ml), add 10% Pd/C (0.03 g) and stir the reaction under a pressure (60 psi) of $H_2$ gas for 16 h. Filter the reaction mixture and concentrate the solvent to obtain compound 6A. Mp 164°-166° C.; CI ($M^+H$) 410.

$[\alpha]_D^{25}$=−28.1° (c 3, $CH_3OH$). Elemental analysis calc'd for $C_{24}H_{21}F_2NO_3$; C 70.41; H 5.17; N 3.42; found C 70.25; H 5.19; N 3.54.

Similarly treat compound 6B-1 to obtain compound 6B. Mp 129.5°-132.5° C.; CI ($M^+H$) 410. Elemental analysis calc'd for $C_{24}H_{21}F_2NO_3$: C 70.41; H 5.17; N 3.42; found C 70.30; H 5.14; N 3.52.

Step 6') (Alternative): To a solution of the product of Step 5 (0.14 g, 0.3 mmol) in ethanol (2 ml), add 10% Pd/C (0.03 g) and stir the reaction under a pressure (60 psi) of $H_2$ gas for 16 h. Filter the reaction mixture and concentrate the solvent to afford a 1:1 mixture of compounds 6A and 6B.

Using appropriate starting materials and following the procedure of steps 1-6, prepare the following compounds:

6C

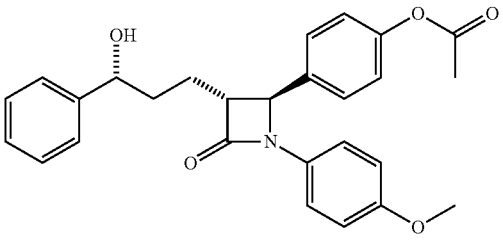

Cl(M + H)446;
HRMS calc'd for $C_{27}H_{27}NO_3$ = 445.1904, found 445.1890

6D

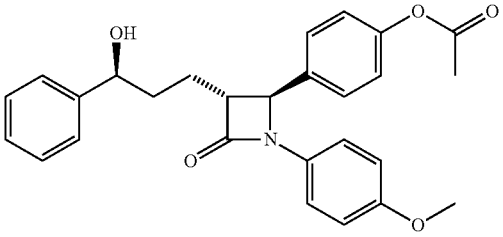

Cl(M + H)446;
HRMS calc'd for $C_{25}H_{25}NO_4$ = 445.1904, found 445.1911

EXAMPLE 7

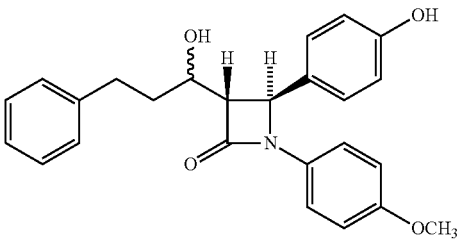

-continued

Step 1):

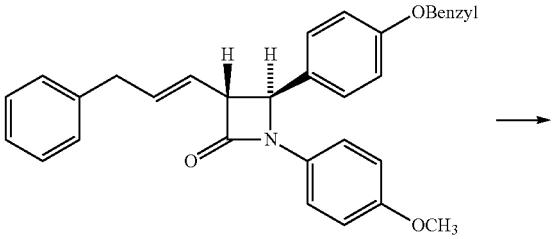

7a

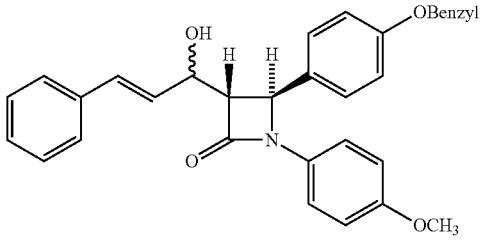

7b

To a solution of 7a (1.0 g, 2.1 mmol) in dioxane (10 ml), add $SeO_2$ (1.33 g, 11.98 mmol) and water [(25 ml, 14 mmol),] (*0.25 ml, 14 mmol*), and heat the reaction to 100° C. After 1 h, cool the reaction to room temperature and isolate by extraction the crude product as a diastereomeric mixture (1:2) of alcohol 7b-A and 7b-R. Purify by HPLC on a Dynamax silica column to separate diastereomers 7b-A and 7b-B.

Diastereomer 7b-A (R): oil; $J_{34}$=2.3 Hz, δ C H(OH)=4.86 (t); HRMS $C_{32}H_{29}NO_4$ calc.: 491.2097; found: 491.2074.

Diastereomer 7b-E (S): oil; $J_{34}$=2.3 Hz, δ C H(OH)=5.06 (t); HRMS $C_{32}H_{29}NO_4$ calc.: 491.2097; found: 491.2117.

Step 2): To a solution of diastereomer A from step 1 (58 mg, 0.12 mmol) in EtOAc (2 ml), add 10% Pd on carbon (20 mg) and stir at 22° C. under $H_2$ gas (14 psi) for 12 h. Filter and concentrate to obtain the title compound as a semisolid, m.p. 90°-92° C. $J_{34}$=2.3 Hz, δ CH(OH)=4.1 (m); HRMS $C_{25}H_{25}NO_4$ calc: 403.1783; found: 403.1792.

EXAMPLE 8

To a solution of the product of Example 4A (90 mg, 0.2 mmol) in $CH_2Cl_2$, add acetyl chloride (80 mg, 1.0 mmol) and pyridine (8 mg, 0.1 mmol) and stir at room temperature for 1 h. Add water, separate the layers and isolate the corresponding acetoxy compound, 8A. In a similar manner, treat the products of Examples 4B, 6B and 6A to obtain the following compounds 8B, 8° C. and 8D, respectively:

8A: 1,4(S)-bis(4-methoxyphenyl)-3(R)-(3(R)-acetoxy-3-phenylpropyl)-2-azetidinone. CI ($M^+H$) 460; HRMS $C_{28}H_{29}NO_5$ calc.: 459.2044; found: 459.2045.

8B: 1,4(S)-bis(4-methoxyphenyl)-3(R)-(3(S)-acetoxy-3-phenylpropyl)-2-azetidinone. CI ($M^+H$) 460; HRMS $C_{28}H_{29}NO_5$ calc.: 459.2044; found 459.2048.

8C: 4(S)-(4-acetyloxyphenyl)-3(R)-(3(R)-acetylox[i]y-3-(4-fluorophenyl)propyl)-1-(4-fluorophenyl)-2-azetidinone. FAB M:S 493.4; HRMS $C_{28}H_{25}F_2NO_5$ calc.: 493.1695; found: 493.1701.

8D: 4(S)-(4-acetyloxyphenyl)-3(R)-(3(S)-acetyloxy-3-(4-fluorophenyl)propyl)-1-(4-fluorophenyl)-2-azetidinone. FAB MS 493.4; HRMS $C_{28}H_{25}F_2NO_5$ calc.: 493.1695; found: 493.1694.

Using appropriate starting materials in the procedure of Example 6, prepare 1-(4-chlorophenyl)-3(R)-(hydroxy-3[.]-

(4-chlorophenylpropyl)-4(S)-(4-hydroxyphenyl)-2-azetidinone. Using the procedure of Example 8, prepare the following diacetates 8E and 8F:

8E

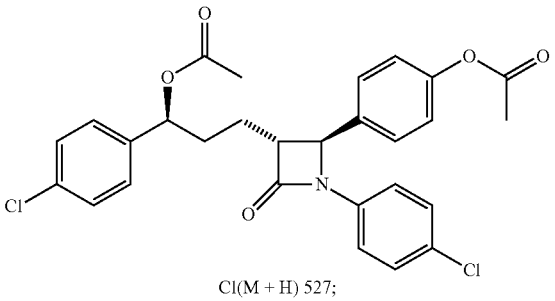

Cl(M + H) 527;
$^1$H $CDCl_3$δ H3' = 4.65

8F

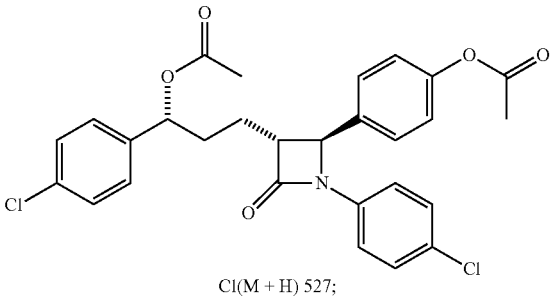

Cl(M + H) 527;
$^1$H $CDCl_3$δ H3' = 4.67

EXAMPLE 9

3H

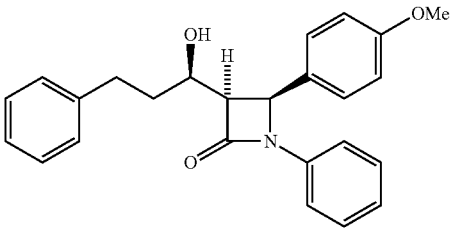

and

3K

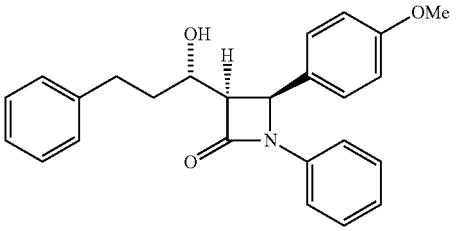

Step 1:

Add pyridinium chlorochromate (2.4 g, 11 mmoles) and $CH_3CO_2Na$ (approx. 20 mg) to a solution of 1-phenyl-3-(3-phenyl-1-hydroxypropyl)-4-(4-methoxyphenyl)-2-azetidinone (2.35 g, 6.1 mmoles) in $CH_2Cl_2$. Stir at room temperature for 18 h, then add silica gel (40 g) and concentrate to dryness. Flash chromatograph the residue using EtOAc:Hex (1:4) to obtain an oil. (1.98 g, yield=85%). $^1$H NMR 2.85-2.95 (m, 3H), 3.15 (m, H), 3.80 (s, 3H), 4.10 (d, 1H, J 2.6), 5.42 (1H, d, 6.85 (dd, 2H, J 2.8), 7.05 (m, 1H), 7.2-7.35 (m, 11H).

Step 2:

To a solution of the product of Step 1 (1.78 g, 4.62 mmoles) in THF at −10° C., add NaH (115 mg, 4.8 mmoles). After 15 min, add NBS (865 mg, 4.85 mmoles) and stir for 20 min., then add 1N HCl and partition between EtOAc and brine. Separate the organic layer, dry ($MgSO_4$) and concentrate to give an oil. Flash chromatograph the oil using EtOAc:Hex (1:10) to collect first 9a as a foamy solid (830 mg, y=39%, FAB MS 466/464, M+H), and then 9b as a colorless solid (1.1 g, y=51%, FAB MS 466/464, M+H).

Step 3a:

Add $Mg(OCOCF_3)_2.CF_3CO_2H$ (7.3 ml of 1M solution is $Et_2O$.) to a solution of 9a (0.68 g, 1.46 mmoles) in THF (5 ml) at −50° C. Stir the reaction 5 min., then add t-Bu—$NH_2$-$BH_3$ (254 mg, 2.92 mmole). After 15 min., allow the reaction to warm to 0° C. over 20 min., add 1N HCl and concentrate in vacuo. Partition the residue between EtOAc and brine. Concentrate the organic layers and dissolve the resultant oil in $CH_2Cl_2$:$CH_3OH$ (1:1) and add ethanolamine (approx 2 mmoles). After 15 min., concentrate the reaction mixture and partition the residue with EtOAc:1N HCl. Wash (brine) and dry ($MgSO_4$) the organic layer to obtain an oil. Purify this oil by flash chromatography using EtOAc:Hex (1:4) to obtain compound 9a-1, a colorless solid, as a 4:1 mix of diastereomers. 0.52 g, y=76%, SIMS 468/466 (M+H).

Step 3b:

Using compound 9b as the starting material, use a procedure similar to Step 3a with $CH_2Cl_2$ as solvent for the preparation of 9b-1 in 80% yield as a 13:1 mixture of diastereomers (SIMS 468/466 M+H).

Step 4a:

Add a solution of 9a-1 (0.27 g, 0.58 mmoles) and AIBN (18 mg, 0.12 mmole) in toluene (40 ml) dropwise over 40 min. to a solution of $(TMS)_3SiH$ (1.0 ml) in toluene at 80° C. or 1.5 h. Cool and concentrate the reaction mixture, dissolve the residue in $CH_3CN$ and wash 3× with hexane. Concentrate the $CH_3CN$ layer to give the title compound as a racemic mixture (0.25 g). Purify this oil by HPLC using a Chiralcel OD column to obtain 3H (major) and 3J (minor).

Step 4b:

Use the procedure of Step 4a, starting with compound 9b-1 to obtain an oil. Purify this by flash chromatography using EtOAc:Hex (1:3) to collect the racemic title compound (y=70%). Purify this oil by HPLC using a Chiralcel OD column to obtain 3J (major) and 3H (minor).

EXAMPLE 10

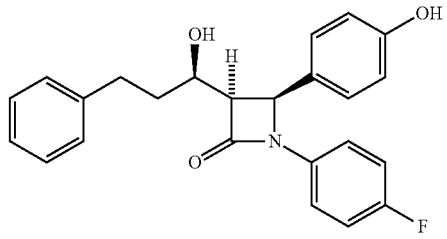

Step 1:

Follow the procedure of Example 3, using 1-(4-fluorophenyl-4-(4-t-butyldimethylsilyloxyphenyl)-2-azetidinone to obtain 1-(4-fluorophenyl-3-(3-phenyl-1-hydroxypropyl) 4-(4-t-butyldimethylsilyl-oxyphenyl)-2-azetidinone.

Step 2:

Treat a solution of the cis-azetidinone of Step 1 (0.25 g) in [CH3CN] $CH_3CN$ (21 ml) with 48% aqueous HF (2.5 ml). After 18 h, dilute the reaction mixture with cold $H_2O$ and extract with $Et_2O$. Wash (2× $H_2O$, dilute $NaHCO_3$ and brine), dry ($MgSO_4$) and concentrate the $Et_2O$ layer. Crystallize the residue from EtOAc:hexane (1:2) to obtain the title compound as colorless needles (123 mg, y=64%), mp 168°-171° C. Elemental analysis calc for $C_{24}H_{22}O_3FN$: C 73.64; H 5.66; N 3.58. found C 73.32; H 5.65; N 3.68.

The following formulations exemplify some of the dosage of this invention. In each the term "active compound" designates a compound of formula I.

EXAMPLE A

Tablets

| No. | Ingredient | mg/tablet | mg/tablet |
|---|---|---|---|
| 1 | Active Compound | 100 | 500 |
| 1 | Lactose USP | 122 | 113 |
| 3 | Corn Starch, Food Grade, as a 10% paste in Purified Water | 30 | 40 |
| 4 | Corn Starch, Food Grade | 45 | 40 |
| 5 | Magnesium Stearate | 3 | 7 |
| | Total | 300 | 700 |

Method of Manufacture

Mix Item Nos. 1 and 2 in suitable mixer for 10-15 minutes. Granulate the mixture with Item No. 3. Mill the damp granules through a coarse screen (e.g., ¼', 0.63 cm) if necessary. Dry the [cl] damp granules. Screen the dried granules if necessary and mix with Item No. 4 and mix for 10-15 minutes. Add Item No. 5 and mix for 1-3 minutes. Compress the mixture to appropriate size and weight on a suitable tablet machine.

EXAMPLE B

Capsules

| No. | Ingredient | mg/tablet | mg/tablet |
|---|---|---|---|
| 1 | Active Compound | 100 | 500 |
| 2 | Lactose USP | 106 | 123 |
| 3 | Corn Starch, Food Grade | 40 | 70 |
| 4 | Magnesium Stearate NF | 4 | 7 |
| | Total | 250 | 700 |

Method of Manufacture

Mix Item Nos. 1, 2 and 3 in a suitable blender for 10-15 minutes. Add Item No. 4 and mix for 1-3 minutes. Fill the mixture suitable two-piece hard gelatin capsules on a suitable encapsulating machine.

Representative formulations comprising a cholesterol biosynthesis inhibitor are well known in the art. It is contemplated that where the two active ingredients are administered as a single composition, the dosage forms disclosed above for substituted azetidinone compounds may readily be modified using the knowledge of one skilled in the art.

Using the test procedures described above, the following in vivo data were obtained for the exemplified compounds. Data is reported as percent change (i.e., percent reduction in cholesterol esters) versus control, therefore, negative numbers indicate a positive lipid-lowering effect.

% Reduction

| Ex. # | Serum Cholest. | Cholest. Esters | Dose mg/kg |
|---|---|---|---|
| 1A | −2.3 | 0 | 50 |
| 1B | −15 | −39 | 50 |
| 1C | 14 | 0 | 50 |
| 2 | 0 | 0 | 50 |
| 3A | −31 | −69 | 50 |
| 3C | −60 | −92 | 50 |
| 3D | −17 | −61 | 10 |
| 3E | 0 | 0 | 10 |
| 3F | −29 | −77 | 10 |
| 3G | −16 | −38 | 10 |
| 3H | −41 | −86 | 10 |
| 3I | 0 | −22 | 10 |
| 3J | 0 | 0 | 3 |
| 3K | 0 | 0 | 10 |
| 3L | −15 | −21 | 10 |
| 3M | 0 | −22 | 10 |
| 4A | 0 | −54 | 5 |
| 4B | −37 | −89 | 8 |
| 4C | −12.5 | 0 | 3 |
| 4D | 9 | 0 | 7 |
| 4E | 0 | −46 | 3 |
| 4F | −29 | −95 | 3 |
| 5 | 0 | −64 | 10 |
| 6A | −59 | −95 | 1 |
| 6A-1 | −43 | −93 | 1 |
| 6B | −40 | −92 | 3 |
| 6C | 0 | −48 | 3 |
| 6D | −46 | −95 | 10 |
| 8A | 0 | −44 | 3 |
| 8B | −50 | −95 | 3 |
| 8C | −14 | −37 | 1 |
| 8D | −49 | −98 | 1 |
| 8E | −22 | −66 | 3 |
| 8F | −43 | −94 | 1 |
| 10 | −26 | −77 | 3 |

We claim:

[[1. A compound represented by the formula

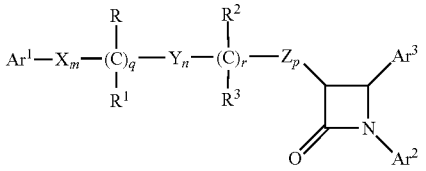

or a pharmaceutically acceptable salt thereof, wherein:

$Ar^1$ and $Ar^2$ are independently selected from the group consisting of aryl and $R^4$-substituted aryl;

$Ar^3$ is aryl or $R^5$-substituted aryl;

X, Y and Z are independently selected from the group consisting of —$CH_2$—, —CH(lower alkyl)- and —C(dilower alkyl)-;

R and $R^2$ are independently selected from the group consisting of —$OR^6$, —O(CO)$R^6$, —O(CO)$OR^9$ and —O(CO)$NR^6R^7$;

$R^1$ and $R^3$ are independently selected from the group consisting of hydrogen, lower alkyl and aryl;

q is 0 or 1; r is 0 or 1; m, n and p are independently 0, 1, 2, 3 or 4; provided that at least one of q and r is 1, and the sum of m, n, p, q and r is 2, 3, 4, 5 or 6; and provided that when p is 0 and r is 1, the sum of m, q and n is 1, 2, 3, 4 or 5;

$R^4$ is 1-5 substituents independently selected from consisting of lower alkyl, —$OR^6$, —$O(CO)R^6$, —$O(CO)OR^9$, —$O(CH_2)_{1-5}OR^6$, —$(CO)NR^6R^7$, —$NR^6R^7$, —$NR^6(CO)R^7$, —$NR^6(CO)OR^9$, —$NR^6(CO)NR^7R^8$, —$NR^6SO_2R^9$, —$COOR^6$, —$CONR^6R^7$, -$COR^6$, -$SO_2NR^6R^7$, $S(O)_{0-2}R^9$, —$O(CH_2)_{1-10}$—$COOR^6$, —$O(CH_2)_{1-10}CONR^6R^7$, -(lower alkylene)$COOR^6$, —CH═CH—$COOR^6$, —$CF_3$, —CN, —$NO_2$ and halogen;

$R^5$ is 1-5 substituents independently selected from the group consisting of —$OR^6$, —$O(CO)R^6$, —$O(CO)OR^9$, —$O(CH_2)_{1-5}OR^6$, —$(CO)NR^6R^7$, —$NR^6R^7$, —$NR^6(CO)R^7$, —$NR^6(CO)OR^9$, —$NR^6(CO)NR^7R^8$, —$NR^6SO_2R^9$, —$COOR^6$, —$CONR^6R^7$, —$COR^6$, —$SO_2NR^6R^7$, $S(O)_{0-2}R^9$, —$O(CH_2)_{1-10}$—$COOR^6$, —$O(CH_2)_{1-10}CONR^6R^7$, -(lower alkylene)$COOR^6$ and —CH═CH—$COOR^6$;

$R^6$, $R^7$ and $R^8$ are independently selected from the group consisting of hydrogen, lower alkyl, aryl and aryl-substituted lower alkyl; and $R^9$ is lower alkyl, aryl or aryl-substituted lower alkyl.]]

[[2. A compound of claim 1 wherein $Ar^1$ is phenyl or $R^4$-substituted phenyl, $Ar^2$ is phenyl or $R^4$-substituted phenyl and $Ar^3$ is $R^5$-substituted phenyl.]]

3. A compound [[of claim 2]] represented by the formula

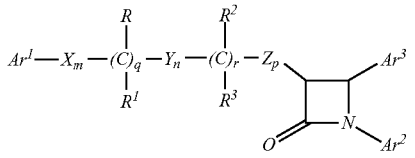

or a pharmaceutically acceptable salt thereof, wherein;

$Ar^1$ is $R^4$-substituted phenyl wherein $R^4$ is halogen; $Ar^2$ is $R^4$-substituted phenyl) wherein $R^4$ is halogen or —$OR^6$, wherein $R^6$ is lower alkyl or hydrogen; and $Ar^3$ is $R^5$-substituted phenyl, wherein $R^5$ is —$OR^6$, wherein [[R6]] $R^6$ is lower alkyl or hydrogen;

X, Y and Z are independently selected from the group consisting of —$CH_2$—, —CH(lower alkyl)— and —C(dilower alkyl)—;

R and $R^2$ are independently selected from the group consisting of —$OR^6$, —$O(CO)R^6$, —$O(CO)OR^9$ and —$O(CO)NR^6R^7$;

$R^1$ and $R^3$ are independently selected from the group consisting of hydrogen, lower alkyl and aryl;

q is 0 or 1; r is 0 or 1; m, n and p are independently 0, 1, 2, 3 or 4; provided that at least one of q and r is 1, and the sum of m, n, p, q and r is 2, 3, 4, 5 or 6; and provided that when p is 0 and r is 1, the sum of m, q and n is 1, 2, 3, 4 or 5;

$R^6$ and $R^7$ are independently selected from the group consisting of hydrogen, lower alkyl, aryl and aryl-substituted lower alkyl; and

$R^9$ is lower alkyl, aryl or aryl-substituted lower alkyl.

[[4. A compound of claim 1 wherein X, Y and Z are each —$CH_2$—; $R^1$ and $R^3$ are each hydrogen; R and $R^2$ are each —$OR^6$, wherein $R^6$ is hydrogen; and the sum of m, n, p, q and r is 2, 3 or 4.]]

[[5. A compound of claim 1 wherein m, n and r are each zero, q is 1 and p is 2.]]

[[6. A compound of claim 1 wherein p, q and n are each zero, r is 1 and m is 2 or 3.]]

7. A compound selected from the group consisting of

[[rel 3(R)-(2(R)-hydroxy-2-phenylethyl)-4(R)-(4-methoxyphenyl)-1-phenyl-2-azetidinone;

rel 3(R)-(2(R)-hydroxy-2-phenylethyl)-4(S)-(4-methoxyphenyl)-1-phenyl-2-azetidinone;

3(S)-(1(S)-hydroxy-3-phenylpropyl)-4(S)-(4-methoxyphenyl)-1-phenyl-2-azetidinone;

3(S)-(1(R)-hydroxy-3-phenylpropyl)-4(S)-(4-methoxyphenyl)-1-phenyl-2-azetidinone;

3(R)-(1(R)-hydroxy-3-phenylpropyl)-4(S)-(4-methoxyphenyl)-1-phenyl-2-azetidinone;

rel-3(R)-[(S)-hydroxy-(2-naphthalenyl)methyl]-4(S)-(4-methoxyphenyl)-1-phenyl)-1-phenyl-2-azetidinone;

rel-3(R)-[(R)-hydroxy-(2-naphthalenyl)methyl]-4(S)-(4-methoxyphenyl)-1-phenyl-2-azetidinone;

3(R)-(3(R)-hydroxy-3-phenylpropyl)-1,4(S)-bis-(4-methoxyphenyl-2-azetidinone;

3(R)-(3(S)-hydroxy-3-phenylpropyl)-1,4(S)-bis-(4-methoxyphenyl-2-azetidinone;

4(S)-(4-hydroxyphenyl)-3(R)-(3(R)-hydroxy-3-phenylpropyl-1-(4-methoxyphenyl)-2-azetidinone;

4(S)-(4-hydroxyphenyl)-3(R)-(3(S)-hydroxy-3-phenylpropyl-1-(4-methoxyphenyl)-2-azetidinone;

rel 3(R)-[3(RS)-hydroxy-3-[4-methoxymethoxy)-phenyl]propyl]-1,4(S)-bis-(4-methoxyphenyl)-2-azetidinone;]]

1-(4-fluorophenyl)-3(R)-[3(S)-(4-fluorophenyl)-3-hydroxypropyl)]-4(S)-(4-hydroxyphenyl)-2-azetidinone; and

1-(4-fluorophenyl)-3(R)-[3(R)-(4-fluorophenyl)-3-hydroxypropyl)]-4(S)-(4-hydroxyphenyl)-2-azetidinone[[;

4(S)-[4-(acetyloxy)phenyl]-3(R)-(3(R)-hydroxy-3-phenylpropyl)-1-(4-methoxyphenyl)-2-azetidinone;

4(S)-[4-(acetyloxy)phenyl]-3(R)-(3(S)-hydroxy-3-phenylpropyl)-1-(4-methoxyphenyl)-2-azetidinone;

1-(4-fluorophenyl)-3(R)-[3(S)-(4-fluorophenyl)-3-hydroxypropyl)]-4(S)-[4(S)-(phenylmethoxy)phenyl]-2-azetidinone;

3(R)-[3(R)-acetyloxy)-3-phenylpropyl]-1,4(S)-bis-(4-methoxyphenyl)-2-azetidinone;

3(R)-[3(S)-acetyloxy)-3-phenylpropyl]-1,4(S)-bis-(4-methoxyphenyl)-2-azetidinone;

3(R)-[3(R)-(acetyloxy)-3-(4-fluorophenyl)propyl]-4(S)-[4-(acetyloxy)phenyl]-1-(4-fluorophenyl)-2-azetidinone;

3(R)-[3(S)-(acetyloxy)-3-(4-fluorophenyl)propyl]-4(S)-[4-(acetyloxy)phenyl]-1-(4-fluorophenyl)-2-azetidinone;

3(R)-[3(R)-(acetyloxy)-3-(4-chlorophenyl)propyl]-4(S)-[4-(acetyloxy)phenyl]-1-(4-chlorophenyl)-2-azetidinone;

3(R)-[3(S)-(acetyloxy)-3-(4-chlorophenyl)propyl]-4(S)-[4-(acetyloxy)phenyl]-1-(4-chlorophenyl)-2-azetidinone; and rel 1-(4-fluorophenyl)-4(S)-(4-hydroxyphenyl)-3(1R)-(1(R)-hydroxy-3-phenylpropyl)-2-azetidinone]].

8. A pharmaceutical composition for the treatment or prevention of [atherscleroses], *atherosclerosis* or for the reduction of plasma cholesterol levels, comprising an effective amount of a compound of claim [[1]] 7 in a pharmaceutically acceptable carrier.

9. A method of treating or preventing atherosclerosis or reducing plasma cholesterol levels comprising administering to a mammal in need of such treatment an effective amount of a compound of claim [[1]] 7.

*10. A compound comprising 1-(4-fluorophenyl)-3(R)-[3(S)-(4-fluorophenyl)-3-hydroxypropyl)]-4(S)-4-(hydroxyphenyl)-2-azetidinone or a pharmaceutically acceptable salt thereof.*

*11. A compound represented by the formula:*

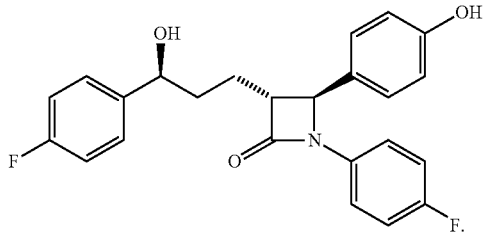

*12. A pharmaceutical composition for the treatment or prevention of atherosclerosis, or for the reduction of plasma cholesterol levels, comprising an effective amount of a compound according to claims 10 or 11 in a pharmaceutically acceptable carrier.*

*13. A method of treating or preventing atherosclerosis or reducing plasma cholesterol levels comprising administering to a mammal in need of such treatment an effective amount of a compound according to claims 10 or 11.*

* * * * *